(12) United States Patent
Gerard et al.

(10) Patent No.: US 6,964,861 B1
(45) Date of Patent: Nov. 15, 2005

(54) ENHANCED IN VITRO RECOMBINATIONAL CLONING OF USING RIBOSOMAL PROTEINS

(75) Inventors: Gary F. Gerard, Frederick, MD (US); Elizabeth Flynn, Columbia, MD (US); A-Li W. Hu, Kensington, MD (US)

(73) Assignee: Invitrogen Corporation, Carlsbad, CA (US)

(*) Notice: Subject to any disclaimer, the term of this patent is extended or adjusted under 35 U.S.C. 154(b) by 0 days.

(21) Appl. No.: 09/438,358

(22) Filed: Nov. 12, 1999

Related U.S. Application Data

(60) Provisional application No. 60/108,324, filed on Nov. 13, 1998.

(51) Int. Cl.[7] .................. C12P 19/34; C12N 15/64; C12N 15/00; C12Q 1/68; C07H 21/04
(52) U.S. Cl. .................. 435/91.1; 435/91.4; 435/91.42; 435/69.1; 435/320.1; 435/252.3; 435/6; 536/23.1; 536/24.2
(58) Field of Search .................. 435/91.1, 91.4, 435/91.42, 69.1, 320.1, 252.3, 325, 6; 536/23.1, 24.2

(56) References Cited

U.S. PATENT DOCUMENTS

| | | |
|---|---|---|
| 4,626,505 A | 12/1986 | Falco |
| 4,673,640 A | 6/1987 | Backman |
| 4,683,195 A | 7/1987 | Mullis et al. |
| 4,683,202 A | 7/1987 | Mullis |
| 4,743,546 A | 5/1988 | Backman et al. |
| 4,959,317 A | 9/1990 | Sauer |
| 4,965,188 A | 10/1990 | Mullis et al. |
| 5,093,257 A | 3/1992 | Gray |
| 5,102,797 A | 4/1992 | Tucker et al. |

(Continued)

FOREIGN PATENT DOCUMENTS

| | | |
|---|---|---|
| CA | 2141412 | 2/1994 |
| EP | 0 160 571 A2 | 11/1985 |
| EP | 0 220 009 A2 | 4/1987 |
| EP | 0 300 422 | 1/1989 |
| EP | 0 427 074 A2 | 5/1991 |
| EP | 0 542 466 A2 | 5/1993 |

(Continued)

OTHER PUBLICATIONS

Nash, Howard A. Methods in Enzymology. vol. 100, pp. 210–216, 1983.*

(Continued)

*Primary Examiner*—Gerry Leffers
(74) *Attorney, Agent, or Firm*—Sterne, Kessler, Goldstein & Fox PLLC

(57) ABSTRACT

The present invention relates generally to compositions and methods for enhancing recombinational cloning of nucleic acid molecules. In particular, the invention relates to compositions comprising one or more ribosomal proteins and one or more additional protein components required for recombinational cloning. More particularly, the invention relates to such compositions wherein the ribosomal proteins are one or more *E. coli* ribosomal proteins, still more particularly wherein the ribosomal proteins are selected from the group of *E. coli* ribosomal proteins consisting of S10, S14, S15, S16, S17, S18, S19, S20, S21, L20, L21, and L23 through L34, and most particularly S20, L27, and S15. The invention also relates to the use of these compositions in methods for recombinational cloning of nucleic acids, in vitro and in vivo, to provide chimeric DNA molecules that have particular characteristics and/or DNA segments. The invention also relates to isolated nucleic acid molecules produced by the methods of the invention, to vectors comprising such nucleic acid molecules, and to host cells comprising such nucleic acid molecules and vectors.

74 Claims, 21 Drawing Sheets

U.S. PATENT DOCUMENTS

| | | | |
|---|---|---|---|
| 5,159,062 A | 10/1992 | Knapp et al. | |
| 5,227,288 A | 7/1993 | Blattner | |
| 5,286,632 A | 2/1994 | Jones | 435/91.2 |
| 5,334,375 A | 8/1994 | Nabi et al. | |
| 5,334,575 A | 8/1994 | Noonan et al. | |
| 5,348,886 A | 9/1994 | Lee et al. | |
| 5,354,668 A | 10/1994 | Auerbach | |
| 5,378,618 A | 1/1995 | Sternberg et al. | |
| 5,434,066 A | 7/1995 | Bebee et al. | |
| 5,470,727 A | 11/1995 | Mascarenhas et al. | |
| 5,527,695 A | 6/1996 | Hodges et al. | |
| 5,591,609 A | 1/1997 | Auerbach | |
| 5,605,793 A | 2/1997 | Stemmer | |
| 5,614,389 A | 3/1997 | Auerbach | |
| 5,635,381 A | 6/1997 | Hooykaas et al. | |
| 5,650,308 A | 7/1997 | Baum | 435/172.3 |
| 5,650,557 A | 7/1997 | Hannah et al. | |
| 5,658,772 A | 8/1997 | Odell et al. | |
| 5,677,170 A | 10/1997 | Devine et al. | |
| 5,677,177 A | 10/1997 | Wahl et al. | |
| 5,710,248 A | 1/1998 | Grose | |
| 5,723,765 A | 3/1998 | Oliver et al. | |
| 5,728,551 A | 3/1998 | Devine et al. | |
| 5,733,733 A | 3/1998 | Auerbach | |
| 5,733,743 A | 3/1998 | Johnson et al. | |
| 5,744,336 A | 4/1998 | Hodges et al. | |
| 5,766,891 A | 6/1998 | Shuman | |
| 5,776,449 A | 7/1998 | Baum et al. | |
| 5,801,030 A | 9/1998 | McVey et al. | |
| 5,814,300 A | 9/1998 | Scott et al. | |
| 5,830,707 A | 11/1998 | Bushman | |
| 5,837,242 A | 11/1998 | Holliger et al. | |
| 5,837,458 A | 11/1998 | Minshull et al. | |
| 5,843,772 A | 12/1998 | Devine et al. | |
| 5,851,808 A | 12/1998 | Elledge et al. | |
| 5,858,657 A | 1/1999 | Winter et al. | |
| 5,871,907 A | 2/1999 | Winter et al. | |
| 5,874,259 A | 2/1999 | Szybalski | |
| 5,888,732 A * | 3/1999 | Hartley et al. | 435/6 |
| 5,916,804 A | 6/1999 | Bushman | |
| 5,919,676 A | 7/1999 | Graham et al. | |
| 5,928,914 A | 7/1999 | Leboulch et al. | |
| 5,929,307 A | 7/1999 | Hodges et al. | |
| 5,962,255 A | 10/1999 | Griffiths et al. | |
| 5,981,177 A | 11/1999 | Demirjian et al. | |
| 5,989,872 A | 11/1999 | Luo et al. | |
| 6,010,884 A | 1/2000 | Griffiths et al. | |
| 6,040,430 A | 3/2000 | Stewart | |
| 6,063,627 A | 5/2000 | McVey et al. | |
| 6,066,778 A | 5/2000 | Ginsburg et al. | |
| 6,080,576 A | 6/2000 | Zambrowicz et al. | |
| 6,143,557 A | 11/2000 | Hartley et al. | 435/320.1 |
| 6,171,861 B1 | 1/2001 | Hartley et al. | 435/455 |
| 6,225,121 B1 | 5/2001 | Savakis et al. | |
| 6,262,341 B1 | 7/2001 | Baszczynski et al. | |
| 6,270,969 B1 | 8/2001 | Hartley et al. | |
| 6,271,436 B1 | 8/2001 | Piedrahita et al. | |
| 6,277,608 B1 | 8/2001 | Hartley et al. | |
| 6,361,972 B1 | 3/2002 | Harrington et al. | |
| 6,365,377 B1 | 4/2002 | Patten et al. | |
| 6,410,266 B1 | 6/2002 | Harrington et al. | |
| 6,410,317 B1 | 6/2002 | Farmer | |
| 6,436,707 B1 | 8/2002 | Zambrowicz et al. | |
| 2002/0007051 A1 | 1/2002 | Cheo et al. | |
| 2002/0068290 A1 | 6/2002 | Yarovinsky | |
| 2002/0094574 A1 | 7/2002 | Hartley et al. | |
| 2002/0172997 A1 | 11/2002 | Hartley et al. | |
| 2002/0192819 A1 | 12/2002 | Hartley et al. | |
| 2003/0027337 A1 | 2/2003 | Droge et al. | |
| 2003/0054552 A1 | 3/2003 | Hartley et al. | |
| 2003/0064515 A1 | 4/2003 | Hartley et al. | |
| 2003/0068799 A1 | 4/2003 | Hartley et al. | |
| 2003/0077804 A1 | 4/2003 | Byrd et al. | |
| 2003/0124555 A1 | 7/2003 | Brasch et al. | |
| 2003/0157662 A1 | 8/2003 | Gerard et al. | |
| 2003/0157716 A1 | 8/2003 | Hartley et al. | |
| 2003/0175970 A1 | 9/2003 | Hartley et al. | |
| 2003/0186233 A1 | 10/2003 | Chesnut et al. | |

FOREIGN PATENT DOCUMENTS

| | | |
|---|---|---|
| EP | 1 035 208 | 9/2000 |
| WO | WO 90/11375 A1 | 10/1990 |
| WO | WO 91/02801 | 3/1991 |
| WO | WO 91/09957 A1 | 7/1991 |
| WO | WO 91/16427 | 10/1991 |
| WO | WO 92/15694 A1 | 9/1992 |
| WO | WO 92/20791 | 11/1992 |
| WO | WO 92/22650 A1 | 12/1992 |
| WO | WO 93/15191 | 8/1993 |
| WO | WO 93/19172 | 9/1993 |
| WO | WO 94/03624 A1 | 2/1994 |
| WO | WO 94/09127 | 4/1994 |
| WO | WO 94/17176 | 8/1994 |
| WO | WO 94/18333 A1 | 8/1994 |
| WO | WO 95/00555 | 1/1995 |
| WO | WO 96/04393 A2 | 2/1996 |
| WO | WO 96/30498 A1 | 10/1996 |
| WO | WO 96/40722 A1 | 12/1996 |
| WO | WO 96/40724 A1 | 12/1996 |
| WO | WO 97/06265 | 2/1997 |
| WO | WO 97/09436 | 3/1997 |
| WO | WO 97/25446 | 7/1997 |
| WO | WO 97/32481 | 9/1997 |
| WO | WO 98/10086 | 3/1998 |
| WO | WO 98/53056 | 11/1998 |
| WO | WO 99/10488 | 3/1999 |
| WO | WO 99/21977 | 5/1999 |
| WO | WO 99/25851 | 5/1999 |
| WO | WO 99/55851 | 11/1999 |
| WO | WO 00/12687 A1 | 3/2000 |
| WO | WO 00/60091 | 10/2000 |
| WO | WO 01/05961 | 1/2001 |
| WO | WO 01/07572 A2 | 2/2001 |
| WO | WO 01/07572 A3 | 2/2001 |
| WO | WO 01/11058 | 2/2001 |
| WO | WO 01/62892 A2 | 8/2001 |
| WO | WO 02/05294 A1 | 1/2002 |

OTHER PUBLICATIONS

Abremski, et al. Journal of Biological Chemistry. vol. 259, No. 3, pp. 1509–1514, 1984.*

Abremski, et al. Journal of Biological Chemistry. vol. 257, No. 16, pp. 9658–9662, 1982.*

Hehl, R., et al., "Structural analysis of Tam3, a transposable element from *Antirrhinum majus,* reveals homologies to the Ac element from maize," *Plant Molec. Biol.* 16:369–371 (1991).

Qin, M., et al., "Cre recombinase–mediated site–specific recombination between plant chromosomes," *Proc. Natl. Acad. Sci. USA* 91:1706–1710 (1994).

Sauer, B., et al., "Construction of Isogenic Cell Lines Expressing Human and Rat Angiotensin II AT1 Receptors by Cre–Mediated Site–Specific Recombination," *Methods: A Companion to Methods in Enzymology* 4:143–149 (1992).

Nagy, A., "Cre Recombinase: The Universal Reagent for Genome Tailoring," *Genesis* 26:99–109 (2000).

Dale, E.C., and Ow, D.W., "Mutations in the Cre/lox recombination site enhance the stability of recombination products: Applications for gene targeting in plants," *J. Cell. Biochem. 16(Suppl. F)*:206, abstract No. Y 108 (1992).

Davies, J., and Riechmann, L., "An antibody VH domain with a lox–Cre site integrated into its coding region: bacterial recombination within a single polypeptide chain," *FEBS Letts. 377*:92–96 (1995).

Krafte, D.S., et al., "Stable Expression and Functional Characterization of a Human Cardiac Na$^+$ Channel Gene in Mammalian Cells," *J. Mol. Cell. Cardiol. 27*:823–830 (1995).

Lee, G., and Saito, I., "Role of nucleotide sequences of loxP spacer region in Cre–mediated recombination," *Gene 216*:55–65 (Aug. 1998).

Simpson, J.C., et al., "Systematic subcellular localization of novel proteins identified by large–scale cDNA sequencing," *EMBO Rep. 1*:287–292 (Sep. 2000).

Venkatesh, T.V., and Radding, C.M., "Ribosomal Protein S1 and NusA Protein Complexed to Recombination Protein β of Phase λ," *J. Bacteriol. 175*:1844–1846 (1993).

Dialog File 351 (Derwent World Patents Index), English language abstract for WIPO/PCT Publication No. WO 98/53056 (Doc. No. AN4), Derwent WPI Accession No. 1999–000502/199901.

Dialog File 351 (Derwent World Patents Index), English language abstract for PCT Publication No. WO 98/53056 (Doc. No. AN4), Derwent WPI Accession No. 1999–347485/199929.

Kuempel, P., et al., "Use of a transposon (Tndif) to obtain suppressing and nonsuppressing insertions of the dif resolvase site of *Escherichia coli*," *Genes Dev. 10*:1162–1171, Cold Spring Harbor Laboratory Press (Jul. 1, 1996).

Lee, M.H., et al., "Site–specific integration of mycobacteriophage L5: Integration–proficient vectors for *Mycobacterium smegmatis, Mycobacterium tuberculosis* and bacille Calmette–Guérin," *Proc. Natl. Acad. Sci. USA 88*:3111–3115, National Academy of Sciences (1991).

Shuman, S., "Novel Approach to Molecular Cloning and Polynucleotide Synthesis Using Vaccina DNA Topoisomerase," *J. Biol. Chem. 269*:32678–32684, The American Society for Biochemistry and Molecular Biology, Inc. (1994).

Zechiedrich, E.L., et al., "Topoisomerase IV, not gyrase, decatenates products of site–specific recombination in *Escherichia coli*," *Genes Dev. 11*:2580–2592, Cold Spring Harbor Laboratory Press (1997).

Institut Pasteur Website, Introduction: http://www.pasteur.fr/recherche/unites/pmtg/integ/intro.html (accessed Jun. 19, 2003).

Institut Pasteur Website, Figure 1: http://www.pasteur.fr/recherche/unites.pmtg/integ/fig1.html (accessed Jun. 19, 2003).

Institut Pasteur Website, Figure 2: http://www.pasteur.fr/recherche/unites.pmtg/integ/fig2.html (accessed Jun. 19, 2003).

Institut Pasteur Website, Figure 3: http://www.pasteur.fr/recherche/unites.pmtg/integ/fig3.html (accessed Jun. 19, 2003).

Institut Pasteur Website, Main page: http://www.pasteur.fr/recherche/unites.pmtg (accessed Jun. 19, 2003).

Ball, C.A., and Johnson, R.C., "Efficient Excision of Phage λ from the *Escherichia coli* Chromosome Requires the Fls Protein," *J. Bacteriol. 173*:4027–4031, American Society of Microbiology (1991).

Lenski, R.E., et al., "Genetic Analysis of a Plasmid–Encoded, Host Genotype–Specific Enhancement of Bacterial Fitness," *J. Bacteriol. 176*:3140–3147, American Society for Microbiology (1994).

Stuurman, J., et al., "Single–site manipulation of tomato chromosomes in vitro and in vivo using Cre–lox site–specific recombination," *Plant Mol. Biol. 32*:901–913, Kluwer Academic Publishers (Nov. 1996).

Backman, K., et al., "Use of Synchronous Site–Specific Recombination In Vivo to Regulate Gene Expression," *Bio/Technology 2*:1045–1049 (1984).

Curcio, M.J., and Garfinkel, D.J., "Single–step selection for Ty 1 element retrotransposition," *Proc. Natl. Acad. Sci. USA 88*:936–940 (1991).

Albert, H., et al., "Site–specific integration of DNA into wild–type and mutant lox sites placed in the plant genome," *Plant J. 7*:649–659, Oxford Bios Scientific Publishers And Blackwell Scientific Publications In Association With The Society For Experimental Biology (1995).

Hall, R.M., and Collis, C.M., "Mobile gene cassettes and integrons: capture and spread of genes by site–specific recombination," *Mol. Microbiol. 15*:593–600, Blackwell Scientific Publications (Feb. 1995).

Jayaram, M., "The Int family of site–specific recombinases: Some thoughts on a general reaction mechanism," *J. Genet. 67*:29–36, Indian Academy of Sciences (1988).

Zahra, D.G., et al., "Selective in–vivo recombination to increase antibody library size—an improved phage display vector system," *Gene 227*:49–54, Elsevier Science Publishers B.V. (Feb. 1999).

Akagi, K., et al., "Cre–mediated somatic site–specific recombination in mice," *Nucl. Acids Res. 25*:1781–1788, Oxford University Press (May 1997).

Aladjem, M.I., et al., "Positive Selection of FLP–Mediated Unequal Sister Chromatid Exchange Products in Mammalian Cells," *Mol. Cell. Biol. 17*:857–861, American Society for Microbiology (Feb. 1997).

Angelastro, J.M., et al., "Identification of diverse nerve growth factor–regulated genes by serial analysis of gene expression (SAGE) profiling," *Proc. Natl. Acad. Sci. USA 97*:10424–10429, National Academy of Sciences (2000).

Angrand, P.O., et al., "Inducible expression based on regulated recombination: a single vector strategy for stable expression in cultured cells," *Nucl. Acids Res. 26*:3263–3269, Oxford University Press (Jul. 1998).

Astumian, J.H., et al., "Site–Specific Recombination between Cloned attP and attB Sites from the *Haemophilus influenzae* Bacteriophage HP1 Propagated in Recombination–Deficient *Escherichia coli*," *J. Bacteriol. 171*:1747–1750, American Society for Microbiology (1989).

Ayres, E.K., et al., "Precise Deletions in Large Bacterial Genomes by Vector–mediated Excision (VEX). The trfA Gene of Promiscuous Plasmid RK2 is Essential for Replication in Several Gram–negative Hosts," *J. Mol. Biol. 230*:174–185, Academic Press (1993).

Bai, C., et al., "SKP1 Connects Cell Cycle Regulators to the Ubiquitin Proteolysis Machinery through a Novel Motif, the F–Box," *Cell 86*:263–274, Cell Press (1996).

Barnes, G., and Rine, J., "Regulated expression of endonuclease EcoRI in *Saccharomyces cerevisiae:* Nuclear entry and biological consequences," *Proc. Natl. Acad. Sci. USA* 82: 1354–1358, National Academy of Sciences (1985).

Bauer, C.E. et al., "Extent of Sequence Homology Required for Bacteriophage Lambda Site–specific Recombination," *J. Mol. Biol. 181*:187–197, Academic Press Inc. (1985).

Bernard, P. et al., "The F Plasmid CcdB Protein Induces Efficient ATP–dependent DNA Cleavage by Gyrase," *J. Mol. Biol. 234*:534–541, Academic Press (1993).

Bernard, P., et al., "Positive–selection vectors using the F plasmid ccdB killer gene," *Gene 148*:71–74, Elsevier Science B.V. (1994).

Boshart, M., et al., "A Very Strong Enhancer is Located Upsteam of an Immediate Early Gene of Human Cytomegalovirus," *Cell 41*:521–530, The MIT Press (1985).

Bouhassira, E.E., et al., "Transcriptional Behavior of LCR Enhancer Elements Integrated at the Same Chromosomal Locus by Recombinase–Mediated Cassette Exchange," *Blood 90*:3332–3344, The American Society of Hematology (Nov. 1997).

Brent, R., and Ptashne, M., "A bacterial repressor protein or a yeast transcriptional terminator can block upstream activation of a yeast gene," *Nature 312*: 612–615, Macmillan Journals Ltd. (1984).

Burioni, R., et al., "An improved phage display vector for antibody repertoire cloning by construction of combinatorial libraries," *Res. Virol. 148*:161–164, Elsevier (Mar.–Apr. 1997).

Capone, J.P., et al., "Introduction of UAG, UAA, and UGA Nonsense Mutations at a Specific Site in the *Escherichia coli* Chloramphenicol Acetyltransferase Gene: Use in Measurement of Amber, Ochre, and Opal Suppression in Mammalian Cells," *Mol. Cell. Biol. 6*:3059–3067, American Society for Microbiology (1986).

Chanock, R.M., et al., "Human Monoclonal Antibody Fab Fragments Cloned from Combinatorial Libraries: Potential Usefulness in Prevention and/or Treatment of Major Human Viral Diseases," *Infect. Agents Dis. 2*:118–131, Raven Press (1993).

Cherepanov, P.P., and Wackernagel, W., "Gene disruption in *Escherichia coli*: $Tc^R$ and $Km^R$ cassetees with the option of Flp–catalyzed excision of the antibiotic–resistance determinant," *Gene 158*:9–14, Elsevier Science B.V. (1995).

Chong, S., et al., "Single–column purification of free recombinant proteins using a self–cleavable affinity tag derived from a protein splicing element," *Gene 192*:271–281. Elsevier Science B.V. (Jun. 1997).

Choulika, A.,et al., "Transfer of Single Gene–Containing Long Terminal Repeats into the Genome of Mammalian Cells by a Retroviral Vector Carrying the cre Gene and the loxP Site." *J. Virol. 70*:1792–1798, American Society for Microbiology (1996).

Chuang, C.–F., and Meyerowitz, E.M., "Specific and heritable genetic interference by double–stranded RNA in *Arabidopsis thaliana,*" *Proc. Natl. Acad. Sci. USA* 97:4985–4990, National Academy of Sciences (2000).

Cigan, A.M., et al., "Mutational Analysis of the HIS4 Translational Initiator Region in *Saccharomyces cerevisiae,*" *Mol. Cell. Biol. 8*:2964–2975, American Society for Microbiology (1988).

CLONTECH, "Creator™ Gene Cloning & Expression System," *CLONTECHniques 15*:7–11, CLONTECH (2000).

CLONTECH, "New Additions to the Creator™ Platform," *CLONTECHniques 16*:1–4, CLONTECH (2001).

CLONTECH, "New Creator™–Compatible Expression Systems," *CLONTECHniques 15*:2 pages, CLONTECH (2000).

CLONTECH, "Creator™ Acceptor Vector Construction Kit" *CLONTECHniques 16*:2 pages, CLONTECH (2001).

CLONTECH, "Creator™ SMART™ Library Construction Kit," *CLONTECHniques 16*:2 pages, CLONTECH (2001).

CLONTECH, "Creator™: The Universal Platform for Analysis of Gene Function," *Powerpoint Presentation,* pp. 1–9, CLONTECH (2001), available at http://www.clontech.com/products/families/creator/popups/s1page1.html.

CLONTECH, "Creator™ pDNR–Dual Cloning Kit," *CLONTECniques 16*:3 pages, CLONTECH (2001).

Collis, C.M. and Hall, R.M., "Expression of Antibiotic Resistance Genes in the Integrated Cassettes of Integrons," *Antimicrobial Agents and Chemotherapy 39*:155–162, American Association for Microbiology (1995).

Cormack, B., "Directed Mutagenesis Using the Polymerase Chain Reaction," in *Current Protocols in Molecular Biology,* Ausubel, F.M., et al., eds., John Wiley & Sons, Inc., New York, NY, pp. 8.5.1–8.5–10 (Jan. 1997).

Datson, N.A., et al., "MicroSAGE: a modified procedure for serial analysis of gene expression in limited amounts of tissue," *Nucl. Acids Res. 27*:1300–1307, Oxford University Press (Mar. 1999).

Davis, C.R., et al., "Analysis of the Mechanisms of Action of the *Saccharomyces cerevisiae* Dominant Lethal $cdc42^{G12V}$ and Dominant Negative $cdc42^{D118A}$ Mutations," *J. Biol. Chem. 273*:849–858, The American Society for Biochemistry and Molecular Biology (Jan. 1998).

Deng, M.–D., and Coleman, J.R., "Ethanol Synthesis by Genetic Engineering in Cyanobacteria," *Appl. Environ. Microbiol. 65*:523–528, American Society for Microbiology (Feb. 1999).

Derbyshire, V., and Belfort, M., "Lightning strikes twice: Intron–intein coincidence," *Proc. Natl. Acad. Sci. USA* 95:1356–1357, National Academy of Sciences (Feb. 1998).

Dijkema, R., et al., "Cloning and expression of the chromosomal immune interferon gene of the rat." *EMBO J.* 4:761–767, IRL Press Limited (1985).

Enquist, L.W., and Weisberg, R.A., "The Red Plaque Test: A Rapid Method for Identification of Excision Defective Variants of Bacteriophage Lambda," *Virology 72*: 147–153, Academic Press, Inc. (1976).

Esposito, D., and Scocca, J.J., "The integrase family of tyrosine recombinases: evolution of a conserved active site domain," *Nucl. Acids Res. 25*:3605–3614, Oxford University Press (Sep. 1997).

Feinbaum, R., "Vectors Derived from Plasmids," in *Current Protocols in Molecular Biology,* Ausubel, P. M., et al., eds., John Wiley & Sons, Inc., New York, NY, pp. 1.5.1–1.5.17 (Jan. 1998).

Flanagan, P.M., and Fennwald, M.A., "Analysis of Inhibitors of the Site–specific Recombination Reaction Mediated by Tn3 Resolvase," *J. Mol. Biol. 206*:295–304, Academic Press (1989).

Flores, A., et al., "A protein–protein interaction map of yeast RNA polymerase III," *Proc. Natl. Acad. Sci. USA* 96:7815–7820, National Academy of Sciences (Jul. 1999).

Francia, M.V., et al., "The IntI1 Integron Integrase Preferentially Binds Single–Stranded DNA of the attC Site," *J. Bacteriol. 181*:6844–6849, American Society for Microbiology (Nov. 1999).

Gateway™ Cloning Technology, Version 1, GIBCO BRL, Life Technologies Instruction Manual, [retrievable from <http://www.lifetech.com/gateway>], pp. 1–60 (Nov. 1999).

Gay, P., et al., "Positive Selection Procedure for Entrapment of Insertion Sequence Elements in Gram–Negative Bacteria," *J. Bacteriol. 164*:918–921, American Society for Microbiology (1985).

Gay, P., et al., "Cloning Structural Gene sacB, Which Codes for Exoenzyme Levansucrase of *Bacillus subtilis:* Expression of the Gene in *Escherichia coli,*" *J. Bacteriol. 153*:1424–1431, American Society for Microbiology (1983).

Gorman, C.M., et al. "The Rous sarcoma virus long terminal repeat is a strong promoter when introduced into a variety of eukaryotic cells by DNA–mediated transfection," *Proc. Natl. Acad. Sci. USA 79*:6777–6781, National Academy of Sciences (1982).

Grindley, N.D.F., and Kelley, W.S., "Effects of Different Alleles of the *E. coli* K12 polA Gene on the Replication of Non–transferring Plasmids," *Molec. Gen. Genet. 143*:311–318, Springer Verlag (1976).

Gronostajski, R.M., and Sadowski, P.D., "The FLP Protein of the 2–micron Plasmid of Yeast. Inter– and Intramolecular Reactions," *J. Biol. Chem. 260*:12328–12335, The American Society of Biological Chemists (1985).

Haffter, P., and Bickle, T.A., "Enhancer–independent mutants of the Cin recombinase have a relaxed topological specificity," *EMBO J. 7*:3991–3996, IRL Press (1988).

Hancock, R.E.W., and Scott, M.G., "The role of antimicrobial peptides in animal defenses," *Proc. Natl. Acad. Sci. USA 97*:8856–8861, National Academy of Sciences (2000).

Henikoff, S., "Unidirectional digestion with exonuclease III creates targeted breakpoints for DNA sequencing," *Gene 28*:351–359, Elsevier Science (1984).

Hochuli, E., et al., "Genetic Approach to Facilitate Purification of Recombinant Proteins with a Novel Metal Chelate Adsorbent," *Bio/Technology 6*:1321–1325, Nature Publishing Company (1988).

Hoess, R.H., and Abremski, K., "Interaction of the bacteriophage P1 recombinase Cre with the recombining site loxP," *Proc. Natl. Acad. Sci. USA 81*:1026–1029, National Academy of Sciences (1984).

Iida, S., et al., "A site–specific, conservative recombination system carried by bacteriophage P1. Mapping of the recombinase gene cin and the crossover sites cix for the inversion of the C segment." *EMBO J. 1*:1445–1453, IRL Press Limited (1982).

Iino, T., and Kutsukake, K., "Trans–acting Genes of Bacteriophages P1 and Mu Mediate Inversion of a Specific DNA Segment Involved in Flagellar Phase Variation of Salmonella," *Cold Spring Harbor Symposia on Quantitative Biology 45*: 11–16, Cold Spring Harbor Laboratory (1981).

Johnson, R.C., et al., "Isolation of the gene encoding the Hin recombinational enhancer binding protein," *Proc. Natl. Acad. Sci. USA 85*:3484–3488, National Academy of Sciences (1988).

Kaniga, K., et al., "A wide–host–range suicide vector for improving reverse genetics in Gram–negative bacteria: inactivation of the blaA gene of *Yersinia enterocolitica,*" *Gene 109*:137–141, Elsevier Science B.V. (1991).

Katz, L., et al., "Site–specific recombination in *Escherichia coli* between the att sites of plasmid pSE211 from *Saccharopolyspora erythraea,*" *Mol. Gen. Genet. 227*: 155–159, Springer–Verlag (1991).

Kealey, J.T., et al., "Production of polyketide natural product in nonpolyketide–producing prokaryotic and eukaryotic hosts," *Proc. Natl. Acad. Sci. USA 95*:505–509, National Academy of Sciences (Jan. 1998).

Kholodenko, B.N., et al., "Metabolis Design: How to Engineer a Living Cell to Desired Metabolite Concentrations and Fluxes," *Biotechnol. Bioengineer. 59*:239–247, John Wiley & Sons (Jul. 1998).

Kim, D.W., "Use of the human elongation factor 1α promoter as a versatile and efficient expression system," *Gene 91*:217–223, Elsevier Science B.V. (1990).

Klippel, A. et al., "Isolation and characterization of unusual gin mutants," *The EMBO Journal 7*: 3983–3989, IRL Press Inc. (1988).

Koch, C., et al., "*Escherichia coli* host factor for site–specific DNA inversion: Cloning and characterization of the fis gene," *Proc. Natl. Acad. Sci. USA 85*:4237–4241, National Academy of Sciences (1988).

Kolb, A.F., and Siddell, S.G., "Genomic targeting with an MBP–Cre fusion protein," *Gene 183*:53–60, Elsevier Science B.V. (1996).

Kouprina, N., et al., "Rescue of Targeted Regions of Mammalian Chromosomes by in Vivo Recombination in Yeast," *Genome Res. 8*:666–672, Cold Spring Harbor Laboratory Press (Jun. 1998).

Krautwald, S., and Baccarini, M., "Bacterially Expressed Murine CSF–1 Possesses Agonistic Activity in its Monomeric Form," *Biochem. Biophys. Res. Commun. 192*: 720–727, Academic Press (1993).

Langeveld, S.A. et al., "Expression of an *Escherichia coli* phr gene in the yeast *Saccharomyces cerevisiae,*" *Mol. Gen. Genet. 199*: 396–400, Springer–Verlag (1985).

Leslie, N.R., and Sherratt, D.J., "Site–specific recombination in the replication terminus region of *Escherichia coli:* functional replacement of dif," *EMBO J. 14*:1561–1570, Oxford University Press (1995).

Leung, L.L.K., "Application of Combinatorial Libraries and Protein Engineering to the Discovery of Novel Anti–Thrombotic Drugs," *Thromb. Haemost. 74*:373–376, F.K. Schattauer Verlagsgesellschaft mbH (1995).

Li, Z.–W., et al., "Generation of mice with a 200–kb amyloid precursor protein gene deletion by Cre recombinase–mediated site–specific recombination in embryonic stem cells," *Proc. Natl. Acad. Sci. USA 93*:6158–6162, National Academy of Sciences (1996).

Lu, F., and Churchward, G., "Conjugative transposition: Tn916 integrase contains two independent DNA binding domains that recognize different DNA sequences," *EMBO J. 13*:1541–1548, Oxford University Press (1994).

Madison, L.L., and Huisman, G.W., "Metabolic Engineering of Poly(3–Hydroxyalkanoates): From DNA to Plastic," *Microbiol. Mol. Biol. Rev. 63*:21–53, American Society for Microbiology (Mar. 1999).

Maemura, K., et al., "Generation of a Dominant–negative Mutant of Endothelial PAS Domain Protein 1 by Deletion of a Potent C–terminal Transactivation Domain," *J. Biol. Chem. 274*:31565–31570, The American Society for Biochemistry and Molecular Biology (Oct. 1999).

Mahillon, J., et al., "Subdivision of the *Escherichia coli* K–12 genome for sequencing: manipulation and DNA sequence of transposable elements introducing unique restriction sites," *Gene* 223:47–54, Elsevier Science B.V. (Nov. 1998).

Malynn, B.A., et al., "The scid Defect Affects the Final Step of the Immunoglobulin VDJ Recombinase Mechanism," *Cell* 54:453–460, Cell Press (1988).

Maniatis, T., et al., "Regulation of Inducible and Tissue–Specific Gene Expression," *Science* 236:1237–1245, American Association for the Advancement of Science (1987).

Manning, P.A., et al., "Gene capture in *Vibrio cholerae*," *Trends Microbiol.* 7:93–95, Elsevier Science (Mar. 1999).

Mendiola, M.V., and de la Cruz, F., "Specificity of insertion of IS91, an insertion sequence present in α–haemolysin plasmids of *Escherichia coli*," *Mol. Microbiol.* 3:979–984, Blackwell Scientific Publications (1989).

Mercier, J., et al., "Structural and Functional Characterization of tnpI, a Recombinase Locus in Tn21 and Related β–Lactamase Transposons," *J. Bacteriol.* 172:3745–3757, American Society for Microbiology (1990).

Metcalf, W.W., et al., "Conditionally Replicative and Conjugative Plasmids Carrying 1acZα for Cloning, Mutagenesis, and Allele Replacement in Bacteria," *Plasmid* 35:1–13, Academic Press (1996).

Mette, M.F., et al., "Transcriptional silencing and promoter methylation triggered by double–stranded RNA," *EMBO J.* 19:5194–5201, Oxford University Press (2000).

Meyer–Leon, L., et al., "Purification of the FLP site–specific recombinase by affinity chromatography and re–examination of basic properties of the system," *Nucl. Acids Res.* 15:6469–6488, IRL Press (1987).

Miller, H.I. et al., "int–h: an int Mutation of Phage λ That Enhances Site–Specific Recombination," *Cell* 20: 721–729, MIT (1980).

Mizushima, S., and Nagata, S., "pEF–BOS, a powerful mammalian expression vector," *Nucl. Acids Res.* 18:5322, Oxford University Press (1990).

Murayama, N., et al., "Evidence for Involvement of *Escherichia coli* Genes pmbA, csrA and a Previously Unrecognized Gene tldD, in the Control of DNA Gyrase by letD (ccdB) of Sex Factor F," *J. Mol. Biol.* 256:483–502, Academic Press Limited (1996).

Nash, H.A., and Robertson, C.A., "Purification and Properties of the *Escherichia coli* Protein Factor Required for λ Integrative Recombination," *J. Biol. Chem.* 256:9246–9253, American Society for Biochemistry and Molecular Biology (1981).

Odell, J.T., et al., "Seed–Specific Gene Activation Mediated by the Cre/lox Site–Specific Recombination System," *Plant Physiol.* 106:447–458, American Society of Plant Physiologists (1994).

O'Gara, J.P., et al., "Identification and Molecular Genetic Analysis of Multiple Loci Contributing to High–Level Tellurite Resistance in *Rhodobacter sphaeroides* 2.4.1," *Appl. Environ. Microbiol.* 63:4713–4720, American Society for Microbiology (Dec. 1997).

Okayama, H., and Berg, P., "Bacteriophage Lambda Vector for Transducing a cDNA Clone Library into Mammalian Cells," *Molecular and Cellular Biology* 5: 1136–1142, American Society for Microbiology (1985).

Osuna, R., et al., "Identification of two functional regions in Fis: the N–terminus is required to promote Hin–mediated DNA inversion by not λ excision," *EMBO J.* 10:1593–1603, Oxford University Press (1991).

Pal, S.K., et al., "P1 Plasmid Replication. Role of Initiator Titration in Copy Number Control," *J. Mol. Biol.* 192:275–285, Academic Press (1986).

Panke, S., et al., "Engineering of Quasi–Natural *Pseudomonas putida* Strains for Toluene Metabolism through an ortho–Cleavage Degradation Pathway," *Appl. Environ. Microbiol.* 64:748–751, American Society for Microbiology (Feb. 1998).

Patel, P.H., and Loeb, L.A., "DNA polymerase active site is highly mutable: Evolutionary consequences," *Proc. Natl. Acad. Sci. USA* 97:5095–5100, National Academy of Sciences (2000).

Perler, F.B., "InBase, the New England Biolabs Intein Database," *Nucl. Acids Res.* 27:346–347, Oxford University Press (Jan. 1999).

Persson, M.A.A., "Combinatorial Libraries," *Intern. Rev. Immunol.* 10:153–163, Harwood Academic Publishers GmbH (1993).

Phillips–Jones, M.K., et al., "Context Effects on Misreading and Suppression at UAG Codons in Human Cells," *Mol. Cell. Biol.* 15:6593–6600, American Society for Microbiology (1995).

Powell, J., "Enhanced concatemer cloning–a modification to the SAGE (Serial Analysis of Gene Expression) technique," *Nucl. Acids Res.* 26:3445–3446, Oxford University Press (Jul. 1998).

Prieto, M.A., et al., "Molecular Characterization of the 4–Hydroxyphenylacetate Catabolic Pathway of *Escherichia coli* W: Engineering a Mobile Aromatic Degradative Cluster," *J. Bacteriol.* 178:111–120, American Society for Microbiology (1996).

Qin, M., et al., "Site–specific cleavage of chromosomes in vitro through Cre–lox recombination," *Nucl. Acids Res.* 23:1923–1927, Oxford University Press (1995).

Ross, W., and Landy, A., "Patterns of λ Int Recognition in the Regions of Strand Exchange," *Cell* 33:261–272, The MIT Press (1983).

Sambrook, J., et al., Molecular Cloning: A Laboratory Manual, 2nd ed., Cold Spring Harbor Laboratory Press, New York, NY, pp. 16.6–16.8, (1989).

Sandhu, J.S., "Protein Engineering of Antibodies," *Crit. Rev. Biotechnol.* 12:437–462, CRC Press (1992).

Sato, T., et al., "The cisA Cistron of *Bacillus subtilis* Sporulation Gene spoIVC Encodes a Protein Homologous to a Site–Specific Recombinase," *J. Bacteriol.* 172:1092–1098, American Society for Microbiology (1990).

Sauer, B., and Henderson, N., "Site–specific DNA recombination in mammalian cells by the Cre recombinase of bacteriophage P1," *Proc. Natl. Acad. Sci. USA* 85: 5166–5170, National Academy of Sciences (1988).

Sauer, B., "Expression and Functioning in Yeast of a Bacterial Site Specific Recombination System," *J. Cel. Bio. Chem. Supp.* 10(b): 242 (I340), Alan R. Liss, Inc. (1986).

Schild, D., et al., "Cloning of three human multifunction de novo purine biosynthetic genes by functional complementation of yeast mutations," *Proc. Natl. Acad. Sci. USA* 87:2916–2920, National Academy of Sciences (1990).

Schnepf, E., et al., "*Bacillus thuringiensis* and Its Pesticidal Crystal Proteins," *Microbiol. Mol. Biol. Rev.* 62:775–806, American Society for Microbiology (Sep. 1998).

Scott, S.D., and Marples, B., "Comment on the use of the cre/loxP recombinase system for gene therapy vectors," *Gene Therapy* 7:1706, Macmillan Publishers Ltd. (2000).

Shim, J., et al., "Distinct and Redundant Functions of $\mu$1 Medium Chains of the AP-1 Clathrin–Associated Protein Complex in the Nematode *Caenorhabditis elegans,*" *Mol. Biol. Cell* 11:2743–2756, The American Society for Cell Biology (2000).

Skraly, F.A., et al., "Construction and Characterization of a 1,3–Propanediol Operon," *Appl. Environ. Microbiol.* 64:98–105, American Society for Microbiology (Jan. 1998).

Spinella, D.G., et al., "Tandem arrayed ligation of expressed sequence tags (TALEST): a new method for generating global gene expression profiles," *Nucl. Acids Res.* 27(e22):i–viii, Oxford University Press (Sep. 1999).

Stark, W.M., et al., "Site–Specific Recombination by Tn3 Resolvase: Topological Changes in the Forward and Reverse Reactions," *Cell* 58:779–790, Cell Press (1989).

Stassi, D.L., et al., "Ethyl–substituted erythromycin derivatives produced by directed metabolic engineering," *Proc. Natl. Acad. Sci. USA* 95:7305–7309, National Academy of Sciences (Jun. 1998).

Stellwagen, A.E., and Craig, N.L., "Mobile DNA elements: controlling transposition with ATP–dependent molecular switches," *Trends Biochem. Sci.* 23:486–490, Elsevier Science (Dec. 1998).

Stenzel, T.T., et al., "The Integration Host Factor of *Escherichia coli* Binds to Bent DNA at the Origin of Replication of the Plasmid pSC101," *Cell* 49:709–717, Cell Press (1987).

Stryer, L., "The DNA Template Contains Stop Signals for transcription," in *Biochemistry, 2nd ed.,* W.H. Freeman and Co., New York, NY, p. 610 (1981).

Sugiura, S., et al., "Minimal Essential Origin of Plasmid pSC101 Replication: Requirement of a Region Downstream of Iterons," *J. Bacteriol.* 175:5993–6001, American Society for Microbiology (1993).

Uetsuki, T., et al., "Isolation and Characterization of the Human Chromosomal Gene for Polypeptide Chain Elongation Factor–1α," *J. Biol. Chem.* 264:5791–5798, The American Society for Biochemistry and Molecular Biology (1989).

van den Berg, A., et al., "Serial analysis of gene expression: rapid RT–PCR analysis of unknown SAGE tags," *Nucl. Acids Res.* 27(e17):i–iii, Oxford University Press (Sep. 1999).

Vetter, D. et al., "Site–specific recombination of yeast 2–$\mu$m DNA in vitro," *Proc. Natl. Acad. Sci. USA* 80: 7284–7288, National Academy of Sciences (1983).

Voss, S.D., et al., "The role of enhancers in the regulation of cell–type–specific transcriptional control," *Trends Biochem. Sci.* 11:287–289, Elsevier Science (1986).

Voziyanov, Y., et al., "A general model for site–specific recombination by the integrase family recombinases," *Nucl. Acids Res.* 27:930–941, Oxford University Press (Feb. 1999).

Yoon, H., et al., "SSL1, a suppressor of a HIS4 5'–UTR stem–loop mutation, is essential for translation initiation and affects UV resistance in yeast," *Genes Dev.* 6:2463–2477, Cold Spring Harbor Laboratory Press (1992).

Abremski, K., and Gottesman, S., "Purification of the Bacteriophage λ xis Gene Product Required for λ Excisive Recombination," *J. Biol. Chem.* 257(16):9658–9662 (1982).

Abremski, K., and Hoess, R., "Bacteriophage P1 Site–specific Recombination—Purification and Properties of the Cre Recombinase Protein," *J. Biol. Chem.* 259:1509–1514 (1984).

Abremski, K., et al., "Bacteriophage P1 Cre–loxP Site–specific Recombination: Site–specific DNA Topoisomerase Activity of the Cre Recombination Protein," *J. Biol. Chem.* 261(1):391–396 (1986).

Abremski, K., et al., "Studies on the Properties of P1 Site–Specific Recombination: Evidence for Topologically Unlinked Products Following Recombination," *Cell* 32:1301–1311 (1993).

Adams, D. E., et al., "Cre–lox Recombination in *Escherichia coli* Cells: Mechanistic Differences from the in Vitro Reaction," *J. Mol. Biol.* 226:661–673 (1992).

Andrews, B.J., et al., "The FLP Recombinase of the 2$\mu$ Circle DNA of Yeast: Interaction with Its Target Sequences," *Cell* 40:795–803 (1985).

Andrews, B.J., et al., "Interaction of the FLP Recombinase of the *Saccharomyces cerevisiae* 2$\mu$m Plasmid with Mutated Target Sequences," *Mol. Cell. Biol.* 6:2482–2489 (1986).

Anton, M., and Graham, F.L., "Site–Specific Recombination Mediated by an Adenovirus Vector Expressing the Cre Recombinase Protein: a Molecular Switch for Control of Gene Expression," *J. Virol.* 69:4600–4606 (1995).

Araki, H., et al., "Site–specific Recombinase, R, Encoded by Yeast Plasmid pSR1," *J. Mol. Biol.* 225:25–37 (1992).

Argos, P., et al., "The integrase family of site–specific recombinases: regional similarities and global diversity," *EMBO J.* 5(2):433–440 (1986).

Atlung, T., et al., "A versatile method for integration of genes and gene fusions into the λ attachment site of *Escherichia coli,*" *Gene* 107:11–17 (1991).

Ausubel, F.M., et al., "Maps of Plasmids pBR322 and pUC19," in *Current Protocols in Molecular Biology,* John Wiley & Sons, Inc., Boston, MA, (1995).

Ausubel, F.M., et al., "Mutegenesis by the Polymerase Chain reaction," in: *Current Protocols in Molecular Biology,* Boston: John Wiley & Sons, Inc., pp. 8.5.1–8.5.9 (1995).

Babineau, D. et al., "The FLP Protein of the 2–micro Plasmid of Yeast," *J. Biol. Chem.* 260:12313–12391 (1985).

Balakrishnan, R., et al., "A gene cassette for adapting *Escherichia coli* strains as hosts for att–Int–mediated rearrangement and $p_L$ expression vectors," *Gene* 138:101–104 (Jan. 1994).

Bayley, C.C., et al., "Exchange of gene activity in transgenic plants catalyzed by the Cre–lox site specific recombination system," *Plant Mol. Biol.* 18:353–361 (1992).

Bethke, B., and Saur, B., "Segmental genomic replacement by Cre–mediated recombination: genotoxic stress activation of the p53 promoter in single–copy transformants," *Nucl. Acids Res.* 25:2828–2834 (Jul. 1997).

Bernard, P., and Couturier, N., "Cell Killing by the F plasmid Ccdb Protein Involves Poisoning of DNA–topoisomerase II Complexes," *J. Mol. Biol.* 226:735–745 (1992).

Bernard, P., "Positive Selection of Recombinant DNA by CcdB," *BioTechniques* 21:320–323 (1996).

Betz, U. A. K., et al., "Bypass of lethality with mosaic mice generated by Cre–loxP–mediated recombination," *Curr. Biol.* 6:1307–1316 (1996).

Bhandari, P and Gowrishankar, J., "An *Escherichia coli* host strain useful for efficient overproduction of cloned gene products with NaCl as the inducer," *J. Bacteriol* 179:4403–4406 (Jul. 1997).

Black, L.W., "In vitro packaging into phage T4 particles and specific recircularization of phage lambda DNAs," *Gene* 46:97–101 (1986).

Bloch, C.A., et al., "Purification of *Escherichia coli* Chromosomal Segments without Cloning," *Biochem. Biophys. Res. Comm.* 223:104–111 (1996).

Bochner, B. R., et al. "Positive Selection for Loss of Tetracycline Resistance," *J. Bacteriol.* 143:926–933 (1980).

Boyd, A. C., "Turbo cloning: a fast, efficient method for cloning PCR products and other blunt–ended DNA fragments into plasmids," *Nucl. Acids Res.* 21(4):817–821 (1993).

Broach, J. R., et al., "Recombination within the Yeast Plasmid 2µ Circle is Site–Specific," *Cell* 29:227–234 (1982).

Brunelli, J. P. and Pall, M. L., "A Series of Yeast/*Escherichia coli* λ Expression Vectors Designed for Directional Cloning of cDNAs and crelox–Mediated Plasmid Excision," *Yeast* 9:1309–1318 (1993).

Brunelli, J.P., and Pall, M.L., "Lambda/Plasmid Vector Construction by In Vivo cre/lox–Mediated Recombination," *BioTechniques* 16(6):1061–1064 (1994).

Bubeck, P., et al., "Rapid cloning by homologous recombination in vivo," *Nucl. Acids Res.* 21:3601–3602 (1993).

Buchholz, F., et al., "A simple assay to determine the functionality of Cre or FLP recombination targets in genomic manipulation constructs," *Nucl. Acids Res.* 24(15):3118–3119 (1996).

Buchholz, F., et al., "Different thermostabilities of FLP and Cre recombinases: implications for applied site–specific recombination," *Nucl. Acids Res.* 24(21):4256–4262 (1996).

Bushman, W., et al., "Control of Directionality in Lambda Site Specific Recombination," *Science* 230:906–911 (1985).

Campbell, A. M., "Chromosomal Insertion Sites for Phages and Plasmids," *J. Bacteriol.* 174(23):7495–7499 (1992).

Chapin, S.J. et al., "Differential expression of alternatively spliced forms of MAP4: a repertoire of structurally different microtubule–binding domains," *Biochem.* 34:2289–2301 (1995).

Chatterjee, P.K., and Coren, J.S., "Isolating large nested deletions in bacterial and P1 artificial chromosomes by in vivo P1 packaging of products of Cre–catalysed recombination between the endogenous and a transposed loxP site," *Nucl. Acids Res.* 25:2205–2212 (Jun. 1997).

Craig, N.L. and Nash, H.A., "The mechanism of phage lambda site–specific recombination: site–specific breakage of DNA by Int topoisomerase," *Cell* 35:795–803 (1983).

Cox, M.M., "The FLP protein of the yeast 2–µm plasmid: Expression of a eukeryotic genetic recombination system in *Escherichia coli*," *Proc. Natl. Acad. Sci. USA* 80:4223–4227 (1983).

Dale, E. C. and Ow, D. W., "Intra– and intermolecular site–specific recombination in plant cells mediated by bacteriophage P1 recombinase," *Gene* 91:79–85 (1990).

Dale, E. C. and Ow, D. W., "Gene transfer with subsequent removal of the selection gene from the host genome," *Proc. Natl. Acad. Sci. USA* 88:10558–10562 (1991).

Dang, D. T. and Perrimon, N., "Use of a Yeast Site–Specific Recombinase to Generate Embryonic Mosaics in *Drosophila*," *Develop. Genetics* 13:367–375 (1992).

Degryse, E., "In vivo intermolecular recombination in *Escherichia coli*: application to plasmid constructions," *Gene* 170:45–50 (1996).

Devine, S. E., and Boeke, J.D., "Efficient integration of artificial transposons into plasmid targets in vitro: a useful tool for DNA mapping, sequencing and genetic analysis," *Nucl. Acids Res.* 22(18):3765–3772 (1994).

Diederich, L., et al., "New Cloning Vectors for Integration into the λ Attachment Site attB of the *Escherichia coli* Chromosome," *Plasmid* 28:14–24 (1992).

Dymecki, S. M., "A modular set of Flp, FRT, and lacZ fusion vectors for manipulating genes by site–specific recombination," *Gene* 171:197–201 (1996).

Elledge, S. J., et al., "λYES: A multifunctional cDNA expression vector for the isolation of genes by complementation of yeast and *Escherichia coli* mutations," *Proc. Natl. Acad. Sci. USA* 88:1731–1735 (1991).

Feil, R., et al., "Regulation of Cre Recombinase Activity by Mutated Estrogen Receptor Ligand–Binding Domains," *Biochem. Biophys. Res. Comm.* 237:752–757 (Aug. 1997).

Ferguson, J., et al., "Construction and characterization of three yeast–*Escherichia coli* shuttle vectors designed for rapid subcloning of yeast genes on small DNA fragments," *Gene* 16:191–197 (1981).

Filutowicz, M., et al., "Purification of the *Escherichia coli* integration host factor (IHF) in one chromatographic step," *Gene* 147:149–150 (1994).

Fiering, S., et al., "An 'in–out' strategy using gene targeting and FLP recombinase for the functional dissection of complex DNA regulatory elements: Analysis of the β–globin locus control region," *Proc. Natl. Acad. Sci. USA* 90:8469–8473 (1993).

Francia, M.V., et al., "Gene integration in the *Escherichia coli* Chromosome Mediated by Tn21 Integrose (Int21)," *J. Bacteriol.* 178:894–898 (1996).

Fukushige, S. and Sauer, B., "Genomic targeting with a positive–selection lox integration vector allows highly reproducible gene expression in mammalian cells," *Proc. Natl. Acad. Sci. USA* 89:7905–7909 (1992).

Geoffroy, F., et al., "A new phage display system to construct multicombinatorial libraries of very large antibody repertoires," *Gene* 151:109–113 (1994).

Glasgow, A.C., et al., "DNA–binding Properties of the Hin Recombinase," *J. Biol. Chem.* 264:10072–10082 (1989).

Golic, K. G. and Lindquist, S., "The FLP Recombinase of Yeast Catalyzes Site–Specific Recombination in the Drosphila Genome," *Cell* 59:499–509 (1989).

Gu, H., et al., "Deletion of a DNA polymerase beta gene segment in T cells using cell type–specific gene targeting," *Science* 265:103–106 (1994).

Guo, F., et al., "Asymmetric DNA bending in the Cre–loxP site–specific recombination synapse," *Proc. Natl. Acad. Sci. USA* 96:7143–7148 (Jun. 1999).

Hardy, S., et al., "Construction of Adenovirus Vectors through Cre–lox Recombination," *J. Virol.* 71(3):1842–1849 (Mar. 1997).

Hasan, N., and Szybalski, W., "Control of cloned gene expression by promoter inversion in vivo: construction of improved vectors with a multiple cloning site and the $D_{ux}$ promoter," *Gene* 56:145–151 (1987).

Hasan, N., et al., "*Escherichia coli* genome targeting, I. Cre–lox–mediated in vitro generation of ori plasmids and their in vivo chromosomal integration and retrieval," *Gene* 150:51–56 (1994).

Hashimoto–Gotoh, T., et al., "Improved vector, pHSG664, for direct streptomycin–resistance selection: cDNA cloning with G:C–tailing procedure and subcloning of double–digested DNA fragments," *Gene 41*:125–128 (1986).

Hoekstra, M. F., et al., "Shuttle Mutagenesis: Bacterial Transposons for Genetic Manipulations in Yeast," *Meth. Enzymol. 194*:329–342 (1991).

Hoess, R.H., et al., "P1 site–specific recombination: Nucleotide sequence of the recombining sites," *Proc. Natl. Acad. Sci. USA 79*:3398–3402 (1982).

Hoess, R.H., et al., "Mechanism of Strand Cleavage and Exchange in the Cre–lox Site–specific Recombination System," *J. Mol. Biol. 181*:351–362 (1985).

Hoess, R., et al., "Formation of small circular DNA molecules via an in vitro site–specific recombination system," *Gene 40*:325–329 (1985).

Hoess, R. H., et al., "The role of the loxP spacer region in P1 site–specific recombination," *Nucl. Acids Res. 14(5)*:2287–2300 (1986).

Hoess, R. H., and Abremski, K., "The Cre–lox Recombination System," in: *Nucleic Acids and Molecular Biology*, vol. 4, ed. by Eckstein, F. and D. M. J. Lilley, Springer–Verlag, Berlin, pp. 99–109 (1990).

Holt, C.L., and May, G.S., "A novel phage λ replacement Cre–lox vector that has automatic subcloning capabilities," *Gene 133*:95–97 (1993).

Hoogenboom, H.R., et al., "Multi–subunit proteins on the surface of filamentous phage: methodologies for displaying antibody (Fab) heavy and light chains," *Nucl. Acids Res. 19*:4133–4137 (1991).

Jaffé, A., et al., "Effects of the ccd Function of the F Plasmid on Bacterial Growth," *J. Bacteriol. 163*:841–849 (1985).

Kanaar, R., et al., "Gin–Mediated Recombination of Catenated and Knotted DNA Substrates: Implications for the Mechanism of Interaction Between Cis–Acting Sites," *Cell 58*:147–159 (1989).

Kilby, N. J., et al., "Site–specific recombinases: tools for genome engineering," *Trends in Genetics 9*:413–421 (1993).

Kim, et al., "Lambda Int protein between higher complexes at two distant chromosomal loci attl and attr," *Science 256*:198–263 (1992).

Kozak, M., "Comparison of initiation of protein synthesis in procaryotes, eucaryotes, and organelles," *Microbiol. Rev. 47*:1–45 (1983).

Kozak, M., "An analysis of 5'–noncoding sequences from 699 vertebrate messenger RNAs," *Nucl. Acids Res. 15*:8125–8132 (1987).

Kozak, M., "Structural features in eukaryotic mRNAs that modulate the initiation of translation," *J. Biol. Chem. 266*:19867–19870 (1991).

Kühn, R., et al., "Inducible Gene Targeting in Mice," *Science 269*:1427–1429 (1995).

Lafontaine, D., and Tollervey, D., "One–step PCR mediated strategy for the construction of conditionally expressed and epitope tagged yeast proteins," *Nucl. Acids Res. 24*:2469–2472 (1996).

Lakso, M., et al., "Targeted oncogene activation by site–specific recombination in transgenic mice," *Proc. Natl. Acad. Sci. USA 89*:6232–6236 (1992).

Lander, E.S., "The New Genomics: Global Views of Biology," *Science 274*:536–539 (1996).

Landy, A., "Mechanistic and structural complexity in the site–specific recombination pathways of Int and FLP," *Curr. Opin. Genet. Develop. 3*:699–707 (1993).

Landy, A., "Dynamic, Structural, and Regulatory Aspects of λ Site–Specific Recombination," *Annu. Rev. Biochem. 58*:913–949 (1989).

Lebreton, B., et al., "Mutations That Improve the Binding of Yeast FLP Recombinase to Its Substrate," *Genetics 118*:393–400 (1988).

Lee, E. C., et al., "Genetic Analysis of *Escherichia coli* Integration Host Factor Interactions with Its Bacteriophage λ H' Recognition Site," *J. Bacteriol. 173*:609–617 (1991).

Leong, J.M., et al., "Generation of single base–pair deletions, insertions, and substitutions by a site–specific recombination system," *Proc. Natl. Acad. Sci. USA 82*:6990–6994 (1985).

Liu, Q., et al., "The univector plasmid–fusion system, a method for rapid construction o recombinant DNA without restriction enzymes," *Curr. Biol. 8*:1300–1309 (Dec. 1998).

Lorbach, E. et al., "Site–specific Recombination in Human Cells Catalyzed by Phage λ Integrase Mutants," *J. Mol. Biol. 296*:1175–1181 (Mar. 2000).

Luckow, V. A., et al., "Efficient Generation of Infectious Recombinant Baculoviruses by Site–Specific Transposon–Mediated Insertion of Foreign Genes into a Baculovirus Genome Propagated in *Escherichia coli*," *J. Virol. 67(8)*:4566–4579 (1993).

Maeser, S., and Kahmann, R., "The Gin recombinase of phage Nu can catalyse site–specific recombination in plant protoplasts," *Mol. Gen. Genet. 230*:170–176 (1991).

Mahillon, J., et al., "IS231 and other *Bacillus thuringiensis* transposable elements: a review," *Genetica 93*:13–26 (1994).

Matsuzaki, H., et al., "Chromosome Engineering in *Saccharomyces cerevisiae* by Using a Site–Specific Recombination System of a Yeast Plasmid," *J. Bacteriol. 172*:610–618 (1990).

McCarthy, J.E. and Brimacombe, R., "Prokaryotic translation: the interactive pathway leading to initiation," *Trends Genet 10*:402–407 (1994).

Medberry, S.L., et al., "Intra–chromosomal rearrangements generated by Cre–lox site–specific recombination," *Nucl. Acids Res. 23*:485–490 (1995).

Miki, T. et al., "Control ofS of Chromosomal DNA by Sex Factor F in *Escherichia coli*. Mutants of DNA Gyrase Subunit A Suppress letD (ccdB) Product Growth Inhibition," *J. Mol. Biol. 225*:39–52 (1992).

Mizuuchi, K., and Mizuuchi, K., "Integrative Recombination of Bacteriophage λ: In Vitro Study of the Intermolecular Reaction," *Cold Spring Harb. Symp. Quant. Biol. 43*:1111–1114 (1979).

Mizuuchi, M. and Mizuuchi, K., "The extent of DNA sequence required for a functional bacterial attachment site of phage lambda," *Nucl. Acids Res. 13*:1193–1208 (1985).

Mozo, T. and Hooykaas, P. J. J., "Design of a novel system for the construction of vectors for Agrobacterium–mediated plant transformation," *Mol. Gen. Genet 236*:1–7 (1992).

Mullins, L.J., et al., "Efficient Cre–lox linearisation of BACs: applications to physical mapping and generation of transgenic animals," *Nucl. Acids Res. 25(12)*:2539–2540 (Jun. 1997).

Nagaraja, R. and Weisberg, R. A., "Specificity Determinants in the Attachment Sites of Bacteriophages HKO22 and λ," *J. Bacteriol. 172*:6540–6550 (1990).

Nash, H.A., "Integrative Recombination of Bacteriophage Lambda DNA In Vitro," *Proc. Natl. Acad. Sci. USA 72*:1072–1076 (1975).

Nash, H.A., and Robertson, CA., "Purification and properties of the *Escherichia coli* protein factor required for lambda integrative recombination," *J. Biol. Chem.* 256:9246–9253 (1981).

Nash, H. A., "Purification and Properties of the Bacteriophage Lambda Int Protein," *Meth. Enzymol.* 100:210–216 (1983).

Nash, H. A., et al., "Role of homology in site–specific recombination of bacteriophage λ: Evidence against joining of cohesive ends," *Proc. Natl. Acad. Sci. USA* 84:4049–4053 (1987).

Nash, H. and C.A. Robertson, "Heteroduplex substrates for bacteriophage lambda site–specific recombination: cleavage and strand transfer products," *EMBO J.* 8:3523–3533 (1989).

Nash, H.A., "Bending and supercoiling of DNA at the attachment site of bacteriophage lambda," *Trends Biochem. Sci* 15:222–227 (1990).

Numrych, T. E., et al., "A comparison of the effects of single–base and triple–base changes in the integrase arm–type binding sites on the site–specific recombination of bacteriophage lambda," *Nucl. Acids Res.* 18:3953–3959 (1990).

Numrych, T.E., et al., "Characterization of the bacteriophage lambda excisionase (Xis) protein: the C–terminus is required for Xis–integrase cooperativity but not for DNA binding," *EMBO J.* 11(10):3797–3806 (1992).

Nunes–Düby, S.E., et al., "Half–att Site Substrates Reveal the Homology Independence and Minimal Protein Requirements for Productive Synapsis in λ Excisive Recombination," *Cell* 59:197–206 (1989).

Nunes–Düby, et al., "Similarities and differences among 105 members of the Int family of site–specific recombinases," *Nucl. Acids Res.* 26:391–406 (Jan. 1998).

Oberto, J., et al., "A segment of the phage HKO22 chromosome is a mosaic of other lambdoid chromosomes," *Nucl. Acids Res.* 22(3):354–356 (1994).

Oliner, J.D., et al., "In vivo cloning of PCR products in *E. coli*," *Nucl. Acids Res.* 21:5192–5197 (1993).

Orban, P. C., et al., "Tissue– and site–specific DNA recombination in transgenic mice," *Proc. Natl. Acad. Sci. USA* 89:6861–6865 (1992).

Osborne, B.I., et al., "A system for insertional mutagenesis and chromosomal rearrangement using the Ds transposon and Cre–lox," *Plant J.* 7:687–701 (1995).

Padgett, K. A. and Sorge, J. A., "Creating seamless junctions independent of restriction sites in PCR cloning," *Gene* 168:31–35 (1996).

Palazzolo, M. J., et al., "Phage lambda cDNA cloning vectors for subtractive hybridization, fusion–protein synthesis and Cre–loxP automatic plasmid subcloning," *Gene* 88:25–36 (1990).

Pan, G., et al., "Ligation of Synthetic Activated DNA Substrates by Site–specific Recombinases and Topoisomerase I," *J. Biol. Chem.* 268(5):3683–3689 (1993).

Parks, R.J., and Graham, F.L., "A Helper–Dependent System for Adenovirus Vector Production Helps Define a Lower Limit for Efficient DNA Packaging," *J. Virol.* 71(4):3293–3298 (Apr. 1997).

Peakman, T. C., et al., "Highly efficient generation of recombinant baculoviruses by enzymatically mediated site–specific in vitro recombination," *Nucl. Acids Res.* 20:495–500 (1992).

Peredelchuk, M.Y., and Bennett, G.N., "A method for construction of *E. coli* strains with multiple DNA insertions in the chromosome," *Gene* 187:231–238 (Mar. 1997).

Pichel, J. G., et al., "Timing of SV40 oncogene activation by site–specific recombination determines subsequent tumor progession during murine lens development," *Gene* 8:3333–3342 (1993).

Pierce, J. C., et al., "A positive selection vector for cloning high molecular weight DNA by the bacteriophage P1 system: Improved cloning efficacy," *Proc. Natl. Acad. Sci. USA* 89:2056–2060 (1992).

Podhajska, A. J., et al., "Control of cloned gene expression by promoter inversion in vivo: construction of the heat–pulse–activated att–nutL–p–att–N module," *Gene* 40:163–168 (1985).

Pósfai, G., et al., "In vivo excision and amplification of large segments of the *Escherichia coli* genome," *Nucl. Acids Res.* 22(12):2392–2398 (1994).

Prasad, P. V., et al., "Substrate Recognition by the 2$\mu$m Circle Site–Specific Recombinase: Effect of Mutations within the Symmetry Elements of the Minimal Substrate," *Mol. Cell. Biol.* 6:4329–4334 (1986).

Qian, X., et al., "Reactions between Half– and Full–FLP Recombination Target Sites: A Model System for Analyzing Early Steps in FLP Protein–Mediated Site–Specific Recombination," *J. Biol. Chem* 267(11):7794–7805 (1992).

Reed, R.R., "Transposon–Mediated Site–Specific Recombination: A Defined in Vitro System," *Cell* 25:713–719 (1981).

Reed, R.R. and N.D. Grindley, "Transposon–Mediated Site–Specific Recombination in Vitro: DNA Cleavage and Protein–DNA Linkage at the Recombination Site," *Cell.* 25:721–728 (1981).

Richet, E., et al., "The Interaction of Recombination Proteins with Supercoiled DNA: Defining the Role of Supercoiling in Lambda Integrative Recombination," *Cell* 46:1011–1021 (1986).

Richet, E., et al., "Synapsis of Attachment Sites during Lambda Integrative Recombination Involves Capture of a Naked DNA by a Protein–DNA Complex," *Cell* 52:9–17 (1988).

Sadowski, P., "Site–Specific Recombinases: Changing Partners and Doing the Twist," *J. Bacteriol.* 165(2):341–347 (1986).

Sadowski, PD, "The Flp recombinase of the 2–microns plasmid of *Saccharomyces cerevisiae*," *Prog. Nucl. Acid Res. Mol. Biol.* 51:53–91 (1995).

Sauer, B., et al., "Site–specific insertion of DNA into a pseudorables virus vector," *Proc. Natl. Acad. Sci. USA* 84:9108–9112 (1987).

Sauer, B., "Functional Expression of the cre–lox Site–Specific Recombination System in the Yeast *Saccharomyces cerevisiae*." *Mol. Cell. Biol.* 7:2087–2096 (1987).

Sauer, B. and Henderson, N., "The cyclization of linear DNA in *Escherichia coli* by site–specific recombination," *Gene* 70:331–341 (1988).

Sauer, B. and Henderson, N., "Cre–stimulated recombination at loxP–containing DNA sequences placed into the mammalian genome," *Nucl. Acids Res.* 17:147–161 (1989).

Sauer, B., "Manipulation of Transgenes by Site–Specific Recombination: Use of Cre Recombinase," *Meth. Enzymol.* 225:890–900 (1993).

Sauer, B., "Site–specific recombination: developments and applications," *Curr. Op. Biotechnol.* 5:521–527 (1994).

Sauer, B., "Multiplex Cre/lox recombination permits selective site–specific DNA targeting to both a natural and an engineered site in the yeast genome," *Nucl. Acids Res.* 24(23):4608–4613 (1996).

Sauer, B., "Inducible gene targeting in mice using the Cre/lox system," *Methods* 14:381–392 (Apr. 1998).

Schindelhauer, D., and Cooke, H.J., "Efficient combination of large DNA in vitro: in gel site specific recombination (IGSSR) of PAC fragments containing α satellite DNA and the human NPRT gene locus," *Nucl. Acids Res.* 25(11):2241–2243 (Jun. 1997).

Schlake, T., and Bode, J., "Use of Mutated FLP Recognition Target (FRT) Sites for the Exchange of Expression Cassettes at Defined Chromosomal Loci," *Biochemistry* 33:12746–12751 (1994).

Segall, A. M. and Nash, H. A., "Synaptic intermediates in bacteriophage lambda site–specific recombination: integrase can align pairs of attachment sites," *EMBO J.* 12:4567–4576 (1993).

Segall, A.M., and Nash, H.A., "Architectural flexibility in lambda site–specific recombination: three alternate conformations channel the attL site into three distinct pathways," *Genes to Cells* 1:453–463 (1996).

Senecoff, J.F., et al., "DNA Recognition by the FLP Recombinase of the Yeast 2 μ Plasmid—A Mutational Analysis of the FLP Binding Site," *J. Mol. Biol.* 201:405–421 (1988).

Sheffield, P. et al., "Overcoming expression and purification problems of RhoGOI using a family of "parallel" expression vectors," *Protein Expr. Purific.* 15:34–39 (Feb. 1999).

Shuman, S., "Recombination mediated by vaccinia virus DNA topoisomerase I in *Escherichia coli* is sequence specific," *Proc. Natl. Acad. Sci. USA* 88:10104–10108 (1991).

Sizemore, C., et al., "Quantitative analysis of Tn10 Tet repressor binding to a complete set of tet operator mutants," *Nucl. Acids Res.* 18(10):2875–2880 (1990).

Smith, A. J. H., et al., "A site–directed chromosomal translocation induced in embryonic stem cells by Cre–loxP recombination," *Nat. Gen.* 9:376–385 (1995).

Snaith, H.R., et al., "Multiple cloning sites carrying loxP and FRT recognition sites for the Cre and Flp site–specific recombinases," *Gene* 166:173–174 (1995).

Spengler, S.J., et al., "The Stereostructure of Knots and Catenanes Produced by Phage λ Integrative Recombination: Implications for Mechanism and DNA Structure," *Cell* 42:325–334 (1985).

Sternberg, N., et al., "Site–specific Recombination and Its Role in the Life Cycle of Bacteriophage P1," *Cold Spring Harbor Symp. Quant. Biol.* 45:297–309 (1981).

Sternberg, N., et al., "Bacteriophage P1 cre Gene and its Regulatory Region," *J. Mol. Biol.* 187:197–212 (1986).

Sternberg, N., "Bacteriophage P1 cloning system for the isolation, amplification, and recovery of DNA fragments as large as 100 kilobase pairs," *Proc. Natl. Acad. Sci. USA* 87:103–107 (1990).

Storck, T., et al., "Rapid construction in yeast of complex targeting vectors for gene manipulation in the mouse," *Nucl. Acids Res.* 24:4594–4596 (1996).

Strathmann, M., et al., "Transposon–facilitated DNA sequencing," *Proc. Natl. Acad. Sci. USA* 88:1247–1250 (1991).

Thompson, J.F., et al., "Mutations in an Integration Host Factor–Binding Site: Effect on Lambda Site–Specific Recombination and Regulatory Implications," *J. Bacteriol.* 168:1343–1351 (1986).

Thompson, J.F., et al., "Helical–repeat dependence of integrative recombination of bacteriophage λ: Role of the P1 and H1 protein binding sites," *Proc. Natl. Acad. Sci. USA* 85:6323–6327 (1988).

Thorpe, H.M., and Smith, H.C.H., "In vitro site–specific integration of bacteriophage DNA catalyzed by a recombinase of the resolvase/invertase family," *Proc. Natl. Acad. Sci. USA* 95:5505–5510 (May 1998).

Tsurushita, N., et al., "Phage display vectors for in vivo recombination of immunoglobul in heavy and light chain genes to make large combinatorial libraries," *Gene* 172:59–63 (1996).

Vanin, E.F., et al., "Development of High–Titer Retroviral Producer Cell Lines by Using Cre–Mediated Recombination," *J. Virol.* 71:7820–7826 (Oct. 1997).

Waterhouse, P., et al., "Combinatorial infection and in vivo recombination: a strategy for making large phage antibody repertoires," *Nucl. Acids Res.* 21(9):2265–2266 (1993).

Wang, G., et al., "pDUAL: A transposon–based cosmid cloning vector for generating nested deletions and DNA sequencing templates in vivo," *Proc. Natl. Acad. Sci. USA* 90:7874–7878 (1993).

Wasserman, S.A., et al., "The helical repeat of double–stranded DNA varies as a function of catenation and supercoiling," *Nature* 334:448–450 (1988).

Wierzbicki, A., et al., "A Mutational Analysis of the Bacteriophage P1 Recombinase Cre," *J. Mol. Biol.* 195:785–794 (1987).

Weisberg, R. A., and Landy, A., "Site–specific Recombination in Phage Lambda," in: "*Lambda II*," Hendrix, R. W. et al., eds., Cold Spring Harbor Laboratory Press, Cold Spring Harbor, N. Y., pp. 211–250 (1983).

Wild, J., et al., "A broad–host–range in vivo pop–out and amplification system for generating large quantities of 50– to 100–kb genomic fragments for direct DNA sequencing," *Gene* 179:181–188 (1996).

Wild, J., et al., "Targeting and retrofitting pre–existing libraries of transposon insertions with FRT and oriV elements for in–vivo generation of large quantities of any genomic fragment," *Gene* 223:55–66 (Nov. 1998).

Winoto, A.,et al., "Directional Control of Site–specific Recombination by Bacteriophage λ," *J. Mol. Biol.* 192:677–680 (1986).

Yang, W., and Mizuuchi, K., "Site–specific recombination in plane view," *Structure* 5:1401–1406 (Nov. 1997).

Yanisch–Perron, C., et al., "Improved M13 phage cloning vectors and host strains: nucleotide sequences of the M13mp18 and pUC19 vectors," *Gene* 33:103–119 (1985).

Yoon, Y.G., et al., "Cre/loxP–mediated in vivo excision of large segments from yeast genome and their amplification based on the 2μm plasmid–derived system," *Gene* 223:67–76 (Nov. 1998).

York, D., et al., "Simple and efficient generation in vitro of nested deletions and inversions: Tn5 intramolecular transposition," *Nucl. Acids Res.* 26:1927–1933 (Apr. 1998).

Zhang, Y. et al., "A new logic for DNA engineering using recombination in *Escherichia coli,*" *Nat. Genet.* 20:123–128 (Oct. 1998).

Zhu, et al., "Homology requirements for ligation and strand excahnge by the FLP recombinase," *J. Biol. Chem.* 270:11646–11653 (1995).

Bruckner, R.C. and Cox, M.M., "The histone–like H protein of *Escherichia coli* is ribosomal protein S3," *Nucl. Acids Res.* 17:3145–3161 (1989).

Gage, P.J., et al., "A Cell–Free Recombination System for Site–Specific Integration of Multigenic Shuttle Plasmids into Herpes Simplex Type 1 Genome," *J. Virol.* 66:5509–5515 (1992).

Götz, F., et al., "*Escherichia coli* 30S mutants lacking protein S20 are defective in translation initiation," *Biochim. Biophys. Acta 1050*:93–97 (1990).

Green, R. and Noller, H.F., "Ribosomes and Translation," *Ann. Rev. Biochem. 66*:679–716 (Jul. 1997).

Jeong, J.–H., et al., "Cloning and nucleotide sequencing of the genes, rp1U and rpmA, for ribosomal proteins L21 and L27 of *Escherichia coli*," *J. DNA sequencing and Mapping 4*:59–67 (1993).

Kitts, P.A. and Nash, H.A., "Bacteriophage Lambda Site–Specific Recombination Proceeds with a Defined Order of Strand Exchanges," *J. Mol. Biol. 204*:95–107 (1988).

Lake, J.A., "Evolving Ribosme Structure: Domains in Archaebacteria, Eubacteria, Eocytes and Eukaryotes," *Ann. Rev. Biochem. 54*:507–530 (1985).

Mackie, G.A., "Nucleotide Sequence of the Gene for Ribosomal Protein S20 and Its Flanking Regions," *J. Biol. Chem. 256*:8177–8182 (1981).

Nomura, M., et al., "Regulation of the Synthesis of Ribosomes and Ribosomal Components," *Ann. Rev. Biochem. 53*:75–117 (1984).

Segall, A.M., et al., "Architectural elements in nucleoprotein complexes: interchangeability of specific and non–specific DNA binding proteins," *EMBO J. 13*:4536–4548 (1994).

Wittman, H.G., "Components of Bacterial Ribosomes," *Ann. Rev. Biochem. 51*:155–183 (1982).

Wittmann, H.G., "Architecture of Prokaryotic Ribosomes," *Ann. Rev. Biochem. 52*:35–65 (1983).

* cited by examiner

ENHANCED IN VITRO RECOMBINATIONAL CLONING OF USING RIBOSOMAL PROTEINS

CROSS REFERENCE TO RELATED APPLICATIONS

The present application claims the benefit of U.S. Provisional Application No. 60/108,324, filed Nov. 13, 1998, the contents of which are incorporated by reference herein in their entirety.

BACKGROUND OF THE INVENTION

1. Field of the Invention

The present invention relates generally to recombinant DNA technology. The invention relates more specifically to compositions and methods for recombinational cloning of nucleic acid molecules using recombination systems. In particular, the invention relates to compositions comprising one or more ribosomal proteins, preferably one or more prokaryotic ribosomal proteins and particularly one or more *E. coli* ribosomal proteins, and one or more additional components required for recombinational cloning (such as one or more recombination proteins), and the use of these compositions in methods of recombinational cloning of nucleic acid molecules. The invention also relates to isolated nucleic acid molecules produced by the methods of the invention, to vectors comprising such nucleic acid molecules, and to host cells comprising such nucleic acid molecules and vectors.

2. Related Art

Site-specific Recombinases

Site-specific recombinases are proteins that are present in many organisms (e.g. viruses and bacteria) and have been characterized to have both endonuclease and ligase properties. These recombinases (along with associated proteins in some cases) recognize specific sequences of bases in DNA and exchange the DNA segments flanking those segments. The recombinases and associated proteins are collectively referred to as "recombination proteins" (see, e.g., Landy, A., *Current Opinion in Biotechnology* 3:699–707 (1993)).

Numerous recombination systems from various organisms have been described. See, e.g., Hoess et al., *Nucleic Acids Research* 14(6):2287 (1986); Abremski et al., *J. Biol. Chem.* 261(1):391 (1986); Campbell, *J. Bacteriol.* 174(23): 7495 (1992); Qian et al., *J. Biol. Chem.* 267(11):7794 (1992); Araki et al., *J. Mol. Biol.* 225(1):25 (1992); Maeser and Kahnmann *Mol. Gen. Genet.* 230:170–176) (1991); Esposito et al., *Nucl. Acids Res.* 25(18) :3605 (1997).

Many of these belong to the integrase family of recombinases (Argos et al. *EMBO J.* 5:433–440(1986)). Perhaps the best studied of these are the Integrase/att system from bacteriophage λ (Landy, A. *Current Opinions in Genetics and Devel.* 3:699–707 (1993)), the Cre/loxP system from bacteriophage P1 (Hoess and Abremski (1990) In *Nucleic Acids and Molecular Biology*,vol. 4. Eds.: Eckstein and Lilley, Berlin-Heidelberg: Springer-Verlag; pp. 90–109), and the FLP/FRT system from the *Saccharomyces cerevisiae* 2µ circle plasmid (Broach et al. *Cell* 29:227–234 (1982)).

Backman (U.S. Pat. No. 4,673,640) discloses the in vivo use of λ recombinase to recombine a protein producing DNA segment by enzymatic site-specific recombination using wild-type recombination sites attB and attP.

Hasan and Szybalski (*Gene* 56:145–151 (1987)) discloses the use of λ Int recombinase in vivo for intramolecular recombination between wild type attP and attB sites which flank a promoter. Because the orientations of these sites are inverted relative to each other, this causes an irreversible flipping of the promoter region relative to the gene of interest.

Palazzolo et al. *Gene* 88:25–36 (1990), discloses phage lambda vectors having bacteriophage λ arms that contain restriction sites positioned outside a cloned DNA sequence and between wild-type loxP sites. Infection of *E. coli* cells that express the Cre recombinase with these phage vectors results in recombination between the loxP sites and the in vivo excision of the plasmid replicon, including the cloned cDNA.

Pósfai et al. (*Nucl. Acids Res.* 22:2392–2398 (1994)) discloses a method for inserting into genomic DNA partial expression vectors having a selectable marker, flanked by two wild-type FRT recognition sequences. FLP site-specific recombinase as present in the cells is used to integrate the vectors into the genome at predetermined sites. Under conditions where the replicon is functional, this cloned genomic DNA can be amplified.

Bebee et al. (U.S. Pat. No. 5,434,066) discloses the use of site-specific recombinases such as Cre for DNA containing two loxP sites is used for in vivo recombination between the sites.

Boyd (*Nucl. Acids Res.* 21:817–821 (1993)) discloses a method to facilitate the cloning of blunt-ended DNA using conditions that encourage intermolecular ligation to a dephosphorylated vector that contains a wild-type loxP site acted upon by a Cre site-specific recombinase present in *E. coli* host cells.

Waterhouse et al. (PCT No. 93/19172 and *Nucleic Acids Res.* 21 (9):2265 (1993)) disclose an in vivo method where light and heavy chains of a particular antibody were cloned in different phage vectors between loxP and loxP 511 sites and used to transfect new *E. coli* cells. Cre, acting in the host cells on the two parental molecules (one plasmid, one phage), produced four products in equilibrium: two different cointegrates (produced by recombination at either loxP or loxP 511 sites), and two daughter molecules, one of which was the desired product.

In contrast to the other related art, Schlake & Bode (*Biochemistry* 33:12746–12751 (1994)) discloses an in vivo method to exchange expression cassettes at defined chromosomal locations, each flanked by a wild type and a spacer-mutated FRT recombination site. A double-reciprocal crossover was mediated in cultured mammalian cells by using this FLP/FRT system for site-specific recombination.

Transposases

The family of enzymes, the transposases, has also been used to transfer genetic information between replicons. Transposons are structurally variable, being described as simple or compound, but typically encode the recombinase gene flanked by DNA sequences organized in inverted orientations. Integration of transposons can be random or highly specific. Representatives such as Tn7, which are highly site-specific, have been applied to the in vivo movement of DNA segments between replicons (Lucklow et al., *J. Virol.* 67:4566–4579 (1993)).

Devine and Boeke *Nucl. Acids Res.* 22:3765–3772 (1994), discloses the construction of artificial transposons for the insertion of DNA segments, in vitro, into recipient DNA molecules. The system makes use of the integrase of yeast TY1 virus-like particles. The DNA segment of interest is cloned, using standard methods, between the ends of the transposon-like element TY1. In the presence of the TY1 integrase, the resulting element integrates randomly into a second target DNA molecule.

DNA Cloning

The cloning of DNA segments currently occurs as a daily routine in many research labs and as a prerequisite step in many genetic analyses. The purpose of these clonings is various, however, two general purposes can be considered: (1) the initial cloning of DNA from large DNA or RNA segments (chromosomes, YACs, PCR fragments, mRNA, etc.), done in a relative handful of known vectors such as pUC, pgem, pBlueScript, and (2) the subcloning of these DNA segments into specialized vectors for functional analysis. A great deal of time and effort is expended in the transfer of DNA segments from the initial cloning vectors to the more specialized vectors. This transfer is called subcloning.

The basic methods for cloning have been known for many years and have changed little during that time. A typical cloning protocol is as follows:

(1) digest the DNA of interest with one or two restriction enzymes;
(2) gel purify the DNA segment of interest when known;
(3) prepare the vector by cutting with appropriate restriction enzymes, treating with alkaline phosphatase, gel purify etc., as appropriate;
(4) ligate the DNA segment to the vector, with appropriate controls to eliminate background of uncut and self-ligated vector;
(5) introduce the resulting vector into an *E. coli* host cell;
(6) pick selected colonies and grow small cultures overnight;
(7) make DNA minipreps; and
(8) analyze the isolated plasmid on agarose gels (often after diagnostic restriction enzyme digestions) or by PCR.

The specialized vectors used for subcloning DNA segments are functionally diverse. These include but are not limited to: vectors for expressing genes in various organisms; for regulating gene expression; for providing tags to aid in protein purification or to allow tracking of proteins in cells; for modifying the cloned DNA segment (e.g., generating deletions); for the synthesis of probes (e.g., riboprobes); for the preparation of templates for DNA sequencing; for the identification of protein coding regions; for the fusion of various protein-coding regions; to provide large amounts of the DNA of interest, etc. It is common that a particular investigation will involve subcloning the DNA segment of interest into several different specialized vectors.

As known in the art, simple subclonings can be done in one day (e.g., the DNA segment is not large and the restriction sites are compatible with those of the subcloning vector). However, many other subclonings can take several weeks, especially those involving unknown sequences, long fragments, toxic genes, unsuitable placement of restriction sites, high backgrounds, impure enzymes, etc. Subcloning DNA fragments is thus often viewed as a chore to be done as few times as possible. Several methods for facilitating the cloning of DNA segments have been described, e.g., as in the following references.

Ferguson, J., et al. *Gene* 16:191 (1981), discloses a family of vectors for subcloning fragments of yeast DNA. The vectors encode kanamycin resistance. Clones of longer yeast DNA segments can be partially digested and ligated into the subcloning vectors. If the original cloning vector conveys resistance to ampicillin, no purification is necessary prior to transformation, since the selection will be for kanamycin.

Hashimoto-Gotob, T., et al. *Gene* 41:125 (1986), discloses a subcloning vector with unique cloning sites within a streptomycin sensitivity gene; in a streptomycin-resistant host, only plasmids with inserts or deletions in the dominant sensitivity gene will survive streptomycin selection.

Accordingly, traditional subcloning methods, using restriction enzymes and ligase, are time consuming and relatively unreliable. Considerable labor is expended, and if two or more days later the desired subclone can not be found among the candidate plasmids, the entire process must then be repeated with alternative conditions attempted. Although site specific recombinases have been used to recombine DNA in vivo, the successful use of such enzymes in vitro was expected to suffer from several problems. For example, the site specificities and efficiencies were expected to differ in vitro; topologically-linked products were expected; and the topology of the DNA substrates and recombination proteins was expected to differ significantly in vitro (see, e.g., Adams et al, *J. Mol. Biol.* 226:661–73 (1992)). Reactions that could go on for many hours in vivo were expected to occur in significantly less time in vitro before the enzymes became inactive. Multiple DNA recombination products were expected in the biological host used, resulting in unsatisfactory reliability, specificity or efficiency of subcloning. Thus, in vitro recombination reactions were not expected to be sufficiently efficient to yield the desired levels of product.

Ribosomal Proteins

Characterization

*E. coli* ribosomes have some 53 different proteins, 21 associated with the 30S subunit (designated S1 through S21) and 32 associated with the 50S subunit (designated L1 through L34). Generally, the lower the number the higher the molecular weight. With the exception of S1 through S4 and L1 through L4, they contain less than 200 amino acids (molecular weights are less than 20 KDa). The primary amino acid sequence of each protein is known. The three-dimensional structures of S5, S6, S8, S17, L1, L7, L9, L14, and L30 are known. Most of these proteins have a relatively high proportion of the two basic amino acids arginine (arg or R) and lysine (lys or K). This intuitively makes sense if most of the ribosomal proteins are assumed to be RNA binding proteins. Much of what is known about ribosomal proteins has been summarized in a series of articles in *Annual Reviews of Biochemistry:* 51:155 (1982); 52:35 (1983); 53:75 (1984); 54:507 (1985); 66:679 (1997).

Enhancement of Yeast Recombination Systems

The yeast FLP/FRT recombination system requires only the FRT DNA binding site and FLP recombinase to carry out recombination. In contrast, the minimum requirements for carrying out recombination in the λ integrase (Int) system include a recombinase (Int) and DNA sites (att), but also IHF protein. IHF is a member of the HU family of small DNA binding proteins. These are basic proteins of 100 amino acids or less that bind to DNA and condense its structure. HU will substitute for IHF in the λ recombination system. While IHF and HU do not stimulate the yeast FLP/FRT recombination system, the *E. coli* ribosomal proteins S3, S4, S5, and L2 do (Bruckner and Cox, *Nucl. Acids Res.* 17:3145–3161 (1989)). The *E. coli* ribosomal proteins that have been shown to stimulate the yeast FLP/FRT recombination system are large, all possessing, with one exception, more than 200 amino acids (Table 1); smaller *E. coli* ribosomal proteins have not been shown to stimulate the FLP/FRT (or any other) recombination system.

TABLE 1

E. coli RIBOSOMAL PROTEINS THAT STIMULATE YEAST FLP/FRT RECOMBINASE

| E. coli Ribosomal Protein | No. of Basic Residues (Percentage of Total) | Total No. of Residues | Molec. Weight |
| --- | --- | --- | --- |
| S3 | 39 (16.8%) | 232 | 25,852 |
| S4 | 39 (19.2%) | 203 | 23,137 |
| S5 | 22 (13.3%) | 166 | 17,515 |
| L2 | 48 (17.8%) | 269 | 29,416 |

SUMMARY OF THE INVENTION

The present invention provides compositions and methods for obtaining amplified, chimeric or recombinant nucleic acid molecules using recombinational cloning, in vitro or in vivo. These methods are highly specific, rapid, and less labor intensive than standard cloning or subcloning techniques. The improved specificity, speed and yields of the present invention facilitates DNA or RNA cloning or subcloning, regulation or exchange useful for any related purpose.

In one embodiment, the present invention relates to compositions for use in cloning or subcloning one or more desired nucleic acid molecules by recombinational cloning, comprising at least one ribosomal protein and at least one recombination protein. In a related aspect, the compositions may comprise more than one ribosomal protein and/or more than one recombination protein. Preferably, prokaryotic ribosomal proteins and prokaryotic recombination proteins are used, although eukaryotic ribosomal proteins and/or eukaryotic recombination proteins may also function in accordance with the invention. According to the invention, the ribosomal proteins used may be basic ribosomal proteins, and may be no larger than about 14 kilodaltons in size.

In certain preferred embodiments, the ribosomal protein may be a prokaryotic ribosomal protein, such as an *Escherichia coli* ribosomal protein, particularly an *E. coli* protein including but not limited to S10, S14, S15, S16, S17, S18, S19, S20, S21, L21, L23, L24, L25, L27, L28, L29, L30, L31, L32, L33 and L34, and most particularly S20, L27 and/or S15. In related embodiments, the recombination protein for use in the compositions is selected from the group consisting of Int, Cre, FLP, Xis, IHF and HU, and is preferably Int. These compositions of the invention may further comprise one or more nucleic acid molecules, including but not limited to one or more Insert Donor molecules, one or more Vector Donor molecules, one or more cointegrate molecules, one or more Product molecules and one or more Byproduct molecules.

The invention also relates generally to methods of cloning or subcloning one or more desired nucleic acid molecules by recombinational cloning. In one such aspect, the invention relates to such methods comprising:

(a) combining in vitro or in vivo
   (i) one or more Insert Donor molecules comprising one or more desired nucleic acid segments flanked by at least two recombination sites, wherein the recombination sites do not substantially recombine with each other;
   (ii) one or more Vector Donor molecules comprising at least two recombination sites, wherein the recombination sites do not substantially recombine with each other;
   (iii) at least one recombination protein; and
   (iv) at least one ribosomal protein;
(b) incubating the combination formed in step (a) under conditions sufficient to transfer one or more of the desired segments into one or more of the Vector Donor molecules, thereby producing one or more desired Product nucleic acid molecules;

and optionally:

(c) combining in vitro or in vivo
   (i) one or more of the Product molecules comprising the desired segments flanked by two or more recombination sites, wherein the recombination sites do not substantially recombine with each other;
   (ii) one or more different Vector Donor molecules comprising two or more recombination sites, wherein the recombination sites do not substantially recombine with each other;
   (iii) at least one recombination protein; and
   (iv) at least one ribosomal protein; and
(d) incubating the combination formed in step (c) under conditions sufficient to transfer one or more of the desired segments into one or more different Vector Donor molecules, thereby producing one or more different Product molecules.

The invention also relates to such methods which further comprise incubating the different Product molecules with one or more different Vector Donor molecules under conditions sufficient to transfer one or more of the desired segments into the different Vector Donor molecules.

In a related aspect, the invention relates to methods of cloning or subcloning one or more desired nucleic acid molecules by recombinational cloning comprising:

a) combining in vitro or in vivo
   i) one or more Insert Donor molecules comprising one or more nucleic acid segments flanked by two or more recombination sites, wherein the recombination sites do not substantially recombine with each other,
   ii) two or more different Vector Donor molecules comprising two or more recombination sites, wherein the recombination sites do not substantially recombine with each other,
   iii) at least one recombination protein; and
   iv) at least one ribosomal protein; and
b) incubating the combination formed in step (a) under conditions sufficient to transfer one or more of the desired segments into the different Vector Donor molecules, thereby producing two or more different Product molecules.

According to the invention, the one or more ribosomal proteins and the one or more recombination proteins for use in these methods are preferably those prokaryotic and/or eukaryotic ribosomal and recombination proteins described herein for use in the compositions of the invention.

In another related aspect, the invention relates to methods of cloning or subcloning one or more desired nucleic acid molecules by recombinational cloning comprising:

(a) combining in vitro or in vivo
   (i) one or more Insert Donor molecules comprising one or more desired nucleic acid segments flanked by at least two recombination sites, wherein the recombination sites do not substantially recombine with each other;
   (ii) one or more Vector Donor molecules comprising at least two recombination sites, wherein the recombination sites do not substantially recombine with each other; and
   (iii) one or more of the compositions of the invention;

(b) incubating the combination formed in step (a) under conditions sufficient to transfer one or more of the desired segments into one or more of the Vector Donor molecules, thereby producing one or more desired Product nucleic acid molecules;

and optionally:

(c) combining in vitro or in vivo
  (i) one or more of the Product molecules comprising the desired segments flanked by two or more recombination sites, wherein the recombination sites do not substantially recombine with each other;
  (ii) one or more different Vector Donor molecules comprising two or more recombination sites, wherein the recombination sites do not substantially recombine with each other; and
  (iii) one or more of the compositions of the invention; and (d) incubating the combination formed in step (c) under conditions sufficient to transfer one or more of the desired segments into one or more different Vector Donor molecules, thereby producing one or more different Product molecules.

In another related aspect, the invention relates to methods of cloning or subcloning one or more desired nucleic acid molecules by recombinational cloning comprising:

a) combining in vitro or in vivo
  i) one or more Insert Donor molecules comprising one or more nucleic acid segments flanked by two or more recombination sites, wherein the recombination sites do not substantially recombine with each other;
  ii) two or more different Vector donor molecules comprising two or more recombination sites, wherein the recombination sites do not substantially recombine with each other; and
  iii) one or more of the compositions of the invention; and b) incubating the combination formed in step (a) under conditions sufficient to transfer one or more of the desired segments into the different Vector Donor molecules, thereby producing two or more different Product molecules.

In another related aspect, the invention relates to methods for recombinational cloning of one or more desired nucleic acid molecules comprising (a) mixing one or more desired nucleic acid molecules with one or more vectors and with one or more of the compositions of the invention; and (b) incubating the mixture under conditions sufficient to transfer the one or more desired nucleic acid molecules into one or more of the vectors.

In another related aspect, the invention relates to methods for enhancement of recombinational cloning of nucleic acid molecules, comprising contacting one or more nucleic acid molecules with one or more ribosomal proteins and one or more recombination proteins, or with one or more compositions of the invention, under conditions favoring the recombinational cloning of the one or more nucleic acid molecules.

According to the invention, the Insert Donor molecules and nucleic acid molecules for use in the compositions and methods of the invention may be derived from genomic DNA or cDNA, or may be produced by chemical synthesis methods. In a related aspect, the Insert Donor molecules may comprise one or more vectors.

According to the invention, the Vector Donor molecules for use in the compositions and methods of the invention may comprise at least one Selectable marker, which may be an antibiotic resistance gene, a tRNA gene, an auxotrophic marker, a toxic gene, a phenotypic marker, an antisense oligonucleotide, a restriction endonuclease, a restriction endonuclease cleavage site, an enzyme cleavage site, a protein binding site, and a sequence complementary to a PCR primer sequence. In a related aspect, the Vector Donor molecules may comprise one or more eukaryotic vectors or one or more prokaryptic vectors. Eukaryotic vectors suitable for use in this aspect of the invention may comprise, for example, vectors which propagate and/or replicate in yeast cells, plant cells, fish cells, eukaryotic cells, mammalian cells, and/or insect cells, while suitable prokaryotic vectors may comprise, for example, vectors which propagate and/or replicate in bacteria of the genera *Escherichia* (most particularly *E. coli*), *Salmonella, Bacillus, Serratia, Streptomyces* or *Pseudomonas*.

The invention also relates generally to DNA molecules produced by the methods of the invention, particularly to such DNA molecules which are isolated DNA molecules. The invention also relates to vectors comprising such DNA molecules, and to host cells comprising such DNA molecules and/or vectors.

The invention also relates to kits for use in recombinational cloning of a nucleic acid molecule. In one such aspect, the kits of the invention may comprise one or more containers, particularly wherein the kit contains at least one ribosomal protein and at least one recombination protein. Such proteins may be contained in separate containers in the kit, or may be combined into a common container or containers. In a related aspect, the kits of the invention may comprise combinations of different ribosomal proteins and/or combinations of different recombination proteins. Ribosomal proteins and recombination proteins suitable for use in the kits of the invention include, but are not necessarily limited to, those described in detail herein.

Other preferred embodiments of the present invention will be apparent to one of ordinary skill in light of what is known in the art, the following drawings and description of the invention, and the claims.

DETAILED DESCRIPTION OF THE INVENTION

Overview

Figure 1:
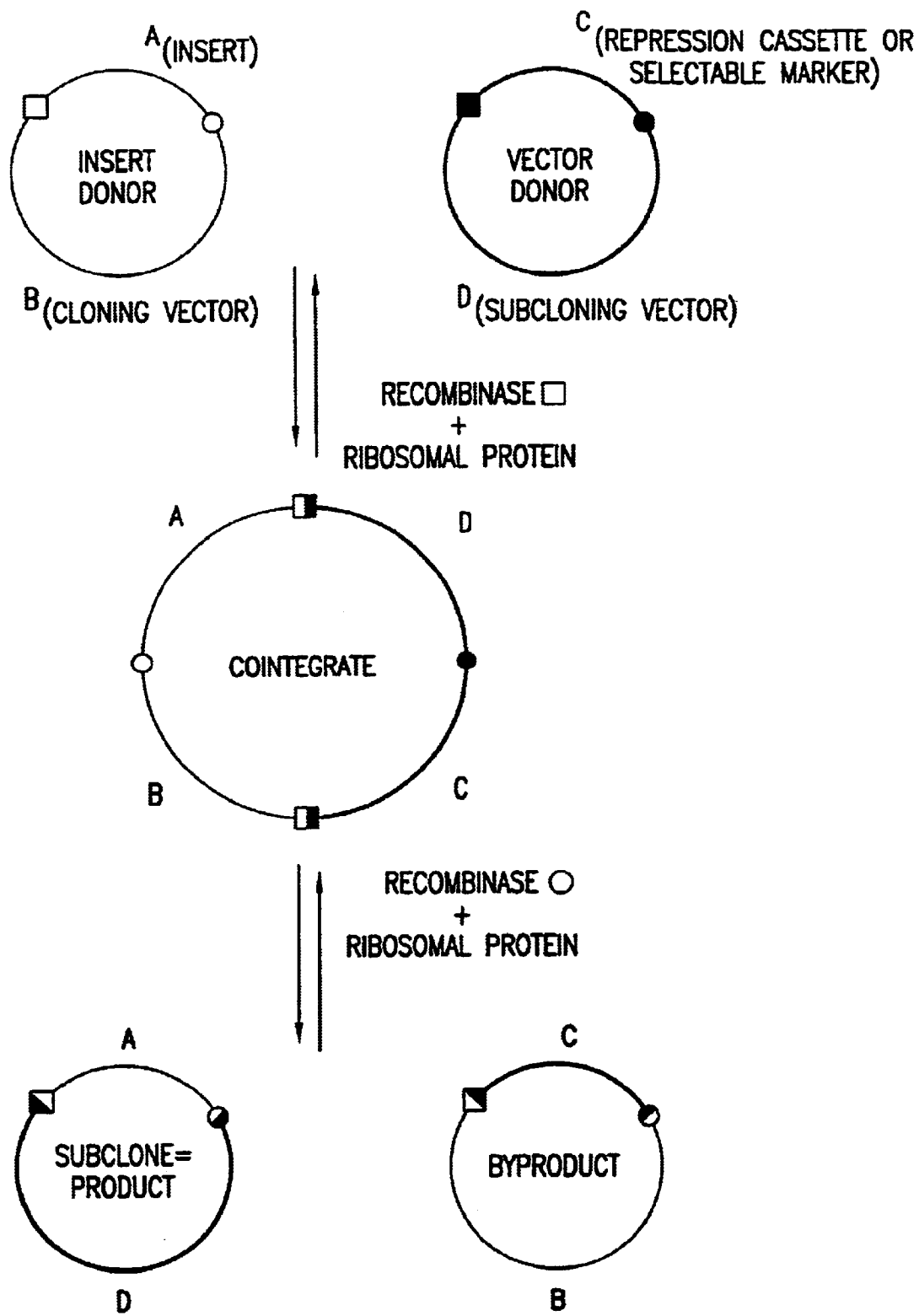
FIG. 1 depicts one general method of the present invention, wherein the starting (parent) DNA molecules can be circular or linear. The goal is to exchange the new subcloning vector D for the original cloning vector B. It is desirable in one embodiment to select for AD and against all the other molecules, including the Cointegrate. The square and circle are sites of recombination: e.g., loxP sites, att sites, etc. For example, segment D can contain expression signals, new drug markers, new origins of replication, or specialized functions for mapping or sequencing DNA.

It has been unexpectedly discovered by the present invention that one or more ribosomal proteins, which may be one or more prokaryotic or eukaryotic ribosomal proteins and particularly one or more *E. coli* ribosomal proteins, may be used to enhance, stimulate, or restore the in vitro and in vivo recombination activity of recombination systems, which may be prokaryotic or eukaryotic recombination systems, such as the λ Int recombination system. Thus, the invention provides compositions comprising such ribosomal proteins, and methods using such compositions, which are useful in performing reversible and/or repeatable cloning and subcloning reactions to manipulate nucleic acid molecules in order to form chimeric nucleic acids using recombination proteins (e.g., λ Int) and recombination sites. Recombinational cloning according to the present invention thus uses compositions comprising one or more ribosomal proteins, and one or more recombination proteins (which may be site-specific prokaryotic recombination proteins), in combination with recombinant nucleic acid molecules having at least one selected recombination site for moving or exchanging segments of nucleic acid molecules, in vitro and in vivo.

The methods of the invention use recombination reactions to generate chimeric DNA or RNA molecules that have the desired characteristic(s) and/or nucleic acid segment(s). The methods of the invention function such that a nucleic acid molecule of interest may be moved or transferred into any number of vector systems. In accordance with the invention, such transfer to various vector systems may be accomplished separately, sequentially or in mass (e.g. into any number of different vectors in one step). The improved specificity, speed and/or yields of the present invention facilitates DNA or RNA cloning, subcloning, regulation or exchange useful for any related purpose. Such purposes include in vitro recombination of DNA or RNA segments and in vitro or in vivo insertion or modification of transcribed, replicated, isolated or genomic DNA or RNA.

Definitions

In the description that follows, a number of terms used in recombinant DNA technology are utilized extensively. In order to provide a clear and consistent understanding of the specification and claims, including the scope to be given such terms, the following definitions are provided.

Adapter: is an oligonucleotide or nucleic acid fragment or segment (preferably DNA) which comprises one or more recombination sites (or portions of such recombination sites) which in accordance with the invention can be added to a circular or linear Insert Donor molecule as well as other nucleic acid molecules described herein. When using portions of recombination sites, the missing portion may be provided by the Insert Donor molecule. Such adapters may be added at any location within a circular or linear molecule, although the adapters are preferably added at or near one or both termini of a linear molecule. Preferably, adapters are positioned to be located on both sides (flanking) a particularly nucleic acid molecule of interest. In accordance with the invention, adapters may be added to nucleic acid molecules of interest by standard recombinant techniques (e.g. restriction digest and ligation). For example, adapters may be added to a circular molecule by first digesting the molecule with an appropriate restriction enzyme, adding the adapter at the cleavage site and reforming the circular molecule which contains the adapter(s) at the site of cleavage. Alternatively, adapters may be ligated directly to one or more and preferably both termini of a linear molecule thereby resulting in linear molecule(s) having adapters at one or both termini. In one aspect of the invention, adapters may be added to a population of linear molecules, (e.g. a cDNA library or genomic DNA which has been cleaved or digested) to form a population of linear molecules containing adapters at one and preferably both termini of all or substantial portion of said population.

Amplification: refers to any in vitro method for increasing a number of copies of a nucleotide sequence with the use of a polymerase. Nucleic acid amplification results in the incorporation of nucleotides into a DNA and/or RNA molecule or primer thereby forming a new molecule complementary to a template. The formed nucleic acid molecule and its template can be used as templates to synthesize additional nucleic acid molecules. As used herein, one amplification reaction may consist of many rounds of replication. DNA amplification reactions include, for example, polymerase chain reaction (PCR). One PCR reaction may consist of 5–100 "cycles" of denaturation and synthesis of a DNA molecule.

Byproduct: is a daughter molecule (a new clone produced after the second recombination event during the recombinational cloning process) lacking the segment which is desired to be cloned or subcloned.

Cointegrate: is at least one recombination intermediate nucleic acid molecule of the present invention that contains both parental (starting) molecules. It will usually be circular. In some embodiments it can be linear.

Host: is any prokaryotic or eukaryotic organism that can be a recipient of the recombinational cloning Product. A "host," as the term is used herein, includes prokaryotic or eukaryotic organisms that can be genetically engineered. For examples of such hosts, see Maniatis et al., *Molecular Cloning: A Laboratory Manual,* Cold Spring Harbor Laboratory, Cold Spring Harbor, N.Y. (1982).

Hybridization: The terms "hybridization" and "hybridizing" refers to base pairing of two complementary single-stranded nucleic acid molecules (RNA and/or DNA) to give a double stranded molecule. As used herein, two nucleic acid molecules may be hybridized, although the base pairing is not completely complementary. Accordingly, mismatched bases do not prevent hybridization of two nucleic acid molecules provided that appropriate conditions, well known in the art, are used.

Insert or Inserts: include the desired nucleic acid segment or a population of nucleic acid segments (segment A of FIG. 1) which may be manipulated by the methods of the present invention. Thus, the terms Insert(s) are meant to include a particular nucleic acid (preferably DNA) segment or a population of segments. Such Insert(s) can comprise one or more genes.

Insert Donor: is one of the two parental nucleic acid molecules (e.g. RNA or DNA) of the present invention which carries the Insert. The Insert Donor molecule comprises the Insert flanked on both sides with recombination sites. The Insert Donor can be linear or circular. In one embodiment of the invention, the Insert Donor is a circular DNA molecule and further comprises a cloning vector sequence outside of the recombination signals (see FIG. 1). When a population of Inserts or population of nucleic acid segments are used to make the Insert Donor, a population of Insert Donors result and may be used in accordance with the invention.

Library: refers to a collection of nucleic acid molecules (circular or linear). In one preferred embodiment, a library is representative of all or a significant portion of the DNA content of an organism (a "genomic" library), or a set of nucleic acid molecules representative of all or a significant portion of the expressed genes (a cDNA library) in a cell, tissue, organ or organism. A library may also comprise random sequences made by de novo synthesis, mutagenesis of one or more sequences and the like. Such libraries may or may not be contained in one or more vectors.

Nucleotide: refers to a base-sugar-phosphate combination. Nucleotides are monomeric units of a nucleic acid sequence (DNA and RNA). The term nucleotide includes ribonucleoside triphosphatase ATP, UTP, CTG, GTP and deoxyribonucleoside triphosphates such as dATP, dCTP, dITP, dUTT, dGTP, dTTP, or derivatives thereof. Such derivatives include, for example, [αS]dATP, 7-deaza-dGTP and 7-deaza-dATP. The term nucleotide as used herein also refers to dideoxyribonucleoside triphosphates (ddNTPs) and their derivatives. Illustrated examples of dideoxyribonucleoside triphosphates include, but are not limited to, ddATP, ddCTP, ddGTP, ddITP, and ddTTP. According to the present invention, a "nucleotide" may be unlabeled or detectably labeled by well known techniques. Detectable labels include, for example, radioactive isotopes, fluorescent labels, chemiluminescent labels, bioluminescent labels and enzyme labels.

Oligonucleotide: refers to a synthetic or natural molecule comprising a covalently linked sequence of nucleotides which are joined by a phosphodiester bond between the 3' position of the deoxyribose or ribose of one nucleotide and the 5' position of the deoxyribose or ribose of the adjacent nucleotide.

Primer: refers to a single stranded or double stranded oligonucleotide that is extended by covalent bonding of nucleotide monomers during amplification or polymerization of a nucleic acid molecule (e.g. a DNA molecule). In a preferred aspect, the primer comprises one or more recombination sites or portions of such recombination sites. Portions of recombination sites comprise at least 2 bases, at least 5 bases, at least 10 bases or at least 20 bases of the recombination sites of interest. When using portions of recombination sites, the missing portion of the recombination site may be provided by the newly synthesized nucleic acid molecule. Such recombination sites may be located within and/or at one or both termini of the primer. Preferably, additional sequences are added to the primer adjacent to the recombination site(s) to enhance or improve recombination and/or to stabilize the recombination site during recombination. Such stabilization sequences may be any sequences (preferably G/C rich sequences) of any length. Preferably, such sequences range in size from 1 to about 1000 bases, 1 to about 500 bases, and 1 to about 100 bases, 1 to about 60 bases, 1 to about 25, 1 to about 10, 2 to about 10 and preferably about 4 bases. Preferably, such sequences are greater than 1 base in length and preferably greater than 2 bases in length.

Product: is one the desired daughter molecules comprising the A and D sequences which is produced after the second recombination event during the recombinational cloning process (see FIG. 1). The Product contains the nucleic acid which was to be cloned or subcloned. In accordance with the invention, when a population of Insert Donors are used, the resulting population of Product molecules will contain all or a portion of the population of Inserts of the Insert Donors and preferably will contain a representative population of the original molecules of the Insert Donors.

Promoter: is a DNA sequence generally described as the 5'-region of a gene, located proximal to the start codon. The transcription of an adjacent DNA segment is initiated at the promoter region. A repressible promoter's rate of transcription decreases in response to a repressing agent. An inducible promoter's rate of transcription increases in response to an inducing agent. A constitutive promoter's rate of transcription is not specifically regulated, though it can vary under the influence of general metabolic conditions.

Recognition sequence: Recognition sequences are particular sequences which a protein, chemical compound, DNA, or RNA molecule (e.g., restriction endonuclease, a modification methylase, or a recombinase) recognizes and binds. In the present invention, a recognition sequence will usually refer to a recombination site. For example, the recognition sequence for Cre recombinase is loxP which is a 34 base pair sequence comprised of two 13 base pair inverted repeats (serving as the recombinase binding sites) flanking an 8 base pair core sequence. See FIG. 1 of Sauer, B., *Current Opinion in Biotechnology* 5:521–527 (1994). Other examples of recognition sequences are the attB, attP, attL, and attR sequences which are recognized by the recombinase enzyme λ Integrase. attB is an approximately 25 base pair sequence containing two 9 base pair core-type Int binding sites and a 7 base pair overlap region. attP is an approximately 240 base pair sequence containing core-type Int binding sites and arm-type Int binding sites as well as sites for auxiliary proteins integration host factor (IHF), FIS, and excisionase (Xis). See Landy, *Current Opinion in Biotechnology* 3:699–707 (1993). Such sites may also be engineered according to the present invention to enhance production of products in the methods of the invention. When such engineered sites lack the P1 or H1 domains to make the recombination reactions irreversible (e.g., attR or attP), such sites may be designated attR' or attP' to show that the domains of these sites have been modified in some way.

Recombinase: is a type of recombination protein which catalyzes the exchange of DNA segments at specific recombination sites.

Recombinational Cloning: is a method described herein, whereby segments of nucleic acid molecules or populations of such molecules are exchanged, inserted, replaced, substituted or modified, in vitro or in vivo.

Recombination proteins: include excisive or integrative proteins, enzymes, co-factors or associated proteins that are involved in recombination reactions involving one or more recombination sites. See, Landy (1994), infra.

Repression cassette: is a nucleic acid segment that contains a repressor of a Selectable marker present in the subcloning vector.

Ribosomal protein: is a polypeptide, protein, or a functional fragment, mutant, or derivative thereof, that is a constituent of a subunit of a ribosome. According to the invention, the ribosome may be a prokaryotic or eukaryotic ribosome, and is preferably a prokaryotic ribosome, particularly an *E. coli* ribosome, comprising a 30S and a 50S subunit. By a "functional" fragment, mutant, or derivative thereof is meant a fragment, mutant, or derivative of a native ribosomal protein that has substantially the same biological activity as the corresponding native ribosomal protein in stimulating a recombination system such as the λ Int recombination system.

Selectable marker: is a DNA segment that allows one to select for or against a molecule or a cell that contains it, often under particular conditions. These markers can encode an activity, such as, but not limited to, production of RNA, peptide, or protein, or can provide a binding site for RNA, peptides, proteins, inorganic and organic compounds or compositions and the like. Examples of Selectable markers include but are not limited to: (1) DNA segments that encode products which provide resistance against otherwise toxic compounds (e.g., antibiotics); (2) DNA segments that encode products which are otherwise lacking in the recipient cell (e.g., tRNA genes, auxotrophic markers); (3) DNA segments that encode products which suppress the activity of a gene product; (4) DNA segments that encode products which can be readily identified (e.g., phenotypic markers such as β-galactosidase, green fluorescent protein (GFP), and cell surface proteins); (5) DNA segments that bind products which are otherwise detrimental to cell survival and/or function; (6) DNA segments that otherwise inhibit the activity of any of the DNA segments described in Nos. 1–5 above (e.g., antisense oligonucleotides); (7) DNA segments that bind products that modify a substrate (e.g. restriction endonucleases); (8) DNA segments that can be used to isolate or identify a desired molecule (e.g. specific protein binding sites); (9,) DNA segments that encode a specific nucleotide sequence which can be otherwise non-functional (e.g., for PCR amplification of subpopulations of molecules); (10) DNA segments, which when absent, directly or indirectly confer resistance or sensitivity to particular compounds; and/or (11) DNA segments that encode products which are toxic in recipient cells.

Selection scheme: is any method which allows selection, enrichment, or identification of a desired Product or Product(s) from a mixture containing the Insert Donor, Vector Donor, any intermediates (e.g. a Cointegrate), and/or Byproducts. The selection schemes of one preferred embodiment have at least two components that are either linked or unlinked during recombinational cloning. One component is a Selectable marker. The other component controls the expression in vitro or in vivo of the Selectable marker, or survival of the cell harboring the plasmid carrying the Selectable marker. Generally, this controlling element will be a repressor or inducer of the Selectable marker, but other means for controlling expression of the Selectable marker can be used. Whether a repressor or activator is used will depend on whether the marker is for a positive or negative selection, and the exact arrangement of the various DNA segments, as will be readily apparent to those skilled in the art. A preferred requirement is that the selection scheme results in selection of or enrichment for only one or more desired Products. As defined herein, selecting for a DNA molecule includes (a) selecting or enriching for the presence of the desired DNA molecule, and (b) selecting or enriching against the presence of DNA molecules that are not the desired DNA molecule.

In one embodiment, the selection schemes (which can be carried out in reverse) will take one of three forms, which will be discussed in terms of FIG. 1. The first, exemplified herein with a Selectable marker and a repressor therefore, selects for molecules having segment D and lacking segment C. The second selects against molecules having segment C and for molecules having segment D. Possible embodiments of the second form would have a DNA segment carrying a gene toxic to cells into which the in vitro reaction products are to be introduced. A toxic gene can be a DNA that is expressed as a toxic gene product (a toxic protein or RNA), or can be toxic in and of itself. (In the latter case, the toxic gene is understood to carry its classical definition of "heritable trait".)

Examples of such toxic gene products are well known in the art, and include, but are not limited to, restriction endonucleases (e.g., DpnI), apoptosis-related genes (e.g. ASK1 or members of the bcl-2/ced-9 family), retroviral genes including those of the human immunodeficiency virus (HIV), defensins such as NP-1, inverted repeats or paired palindromic DNA sequences, bacteriophage lytic genes such as those from φX174 or bacteriophage T4; antibiotic sensitivity genes such as rpsL, antimicrobial sensitivity genes such as pheS, plasmid killer genes, eukaryotic transcriptional vector genes that produce a gene product toxic to bacteria, such as GATA-1, and genes that kill hosts in the absence of a suppressing function, e.g., kicB or ccdB. A toxic gene can alternatively be selectable in vitro, e.g., a restriction site.

Many genes coding for restriction endonucleases operably linked to inducible promoters are known, and may be used in the present invention. See, e.g. U.S. Pat. No. 4,960,707 (DpnI and DpnII); U.S. Pat. Nos. 5,000,333, 5,082,784 and 5,192,675 (KpnI); U.S. Pat. No. 5,147,800 (NgoAIII and NgoAI); U.S. Pat. No. 5,179,015 (FspI and HaeIII): U.S. Pat. No. 5,200,333 (HaeII and TaqI); U.S. Pat. No. 5,248,605 (HpaII); U.S. Pat. No. 5,312,746 (ClaI); U.S. Pat. Nos. 5,231,021 and 5,304,480 (XhoI and XhoII); U.S. Pat. No. 5,334,526 (AluI); U.S. Pat. No. 5,470,740 (NsiI); U.S. Pat. No. 5,534,428 (SstI/SacI); U.S. Pat. No. 5,202,248 (NcoI); U.S. Pat. No. 5,139,942 (NdeI); and U.S. Pat. No. 5,098,839 (PacI). See also Wilson, G. G., *Nucl. Acids Res.* 19:2539–2566 (1991); and Lunnen, K. D., et al., *Gene* 74:25–32 (1988).

In the second form, segment D carries a Selectable marker. The toxic gene would eliminate transformants harboring the Vector Donor, Cointegrate, and Byproduct molecules, while the Selectable marker can be used to select for cells containing the Product and against cells harboring only the Insert Donor.

The third form selects for cells that have both segments A and D in cis on the same molecule, but not for cells that have both segments in trans on different molecules. This could be embodied by a Selectable marker that is split into two inactive fragments, one each on segments A and D.

The fragments are so arranged relative to the recombination sites that when the segments are brought together by the recombination event, they reconstitute a functional Selectable marker. For example, the recombinational event can link a promoter with a structural gene, can link two fragments of a structural gene, or can link genes that encode a heterodimeric gene product needed for survival, or can link portions of a replicon.

Site-specific recombinase: is a type of recombinase which typically has at least the following four activities (or combinations thereof): (1) recognition of one or two specific nucleic acid sequences; (2) cleavage of said sequence or sequences; (3) topoisomerase activity involved in strand exchange; and (4) ligase activity to reseal the cleaved strands of nucleic acid. See Sauer, B., *Current Opinions in Biotechnology* 5:521–527 (1994). Conservative site-specific recombination is distinguished from homologous recombination and transposition by a high degree of specificity for both partners. The strand exchange mechanism involves the cleavage and rejoining of specific DNA sequences in the absence of DNA synthesis (Landy, A. (1989) *Ann. Rev. Biochem.* 58:913–949).

Subcloning vector: is a cloning vector comprising a circular or linear nucleic acid molecule which includes preferably an appropriate replicon. In the present invention, the subcloning vector (segment D in FIG. 1) can also contain functional and/or regulatory elements that are desired to be incorporated into the final product to act upon or with the cloned DNA Insert (segment A in FIG. 1). The subcloning vector can also contain a Selectable marker (preferably DNA).

Template: refers to double stranded or single stranded nucleic acid molecules which are to be amplified, synthesized or sequenced. In the case of double stranded molecules, denaturation of its strands to form a first and a second strand is preferably performed before these molecules will be amplified, synthesized or sequenced, or the double stranded molecule may be used directly as a template. For single stranded templates, a primer complementary to a portion of the template is hybridized under appropriate conditions and one or more polypeptides having polymerase activity (e.g. DNA polymerases and/or reverse transcriptases) may then synthesize a nucleic acid molecule complementary to all or a portion of said template. Alternatively, for double stranded templates, one or more promoters may be used in combination with one or more polymerases to make nucleic acid molecules complementary to all or a portion of the template. The newly synthesized molecules, according to the invention, may be equal or shorter in length than the original template. Additionally, a population of nucleic acid templates may be used during synthesis or amplification to produce a population of nucleic acid molecules typically representative of the original template population.

Vector: is a nucleic acid molecule (preferably DNA) that provides a useful biological or biochemical property to an Insert. Examples include plasmids, phages, autonomously replicating sequences (ARS), centromeres, and other sequences which are able to replicate or be replicated in vitro or in a host cell, or to convey a desired nucleic acid segment to a desired location within a host cell. A Vector can have one or more restriction endonuclease recognition sites at which the sequences can be cut in a determinable fashion without loss of an essential biological function of the vector, and into which a nucleic acid fragment can be spliced in order to bring about its replication and cloning. Vectors can further provide primer sites, e.g., for PCR, transcriptional and/or translational initiation and/or regulation sites, recombinational signals, replicons, Selectable markers, etc. Clearly, methods of inserting a desired nucleic acid fragment which do not require the use of homologous recombination, transpositions or restriction enzymes (such as, but not limited to, UDG cloning of PCR fragments (U.S. Pat. No. 5,334,575, entirely incorporated herein by reference), T:A cloning, and the like) can also be applied to clone a fragment into a cloning vector to be used according to the present invention. The cloning vector can further contain one or more selectable markers suitable for use in the identification of cells transformed with the cloning vector.

Vector Donor: is one of the two parental nucleic acid molecules (e.g. RNA or DNA) of the present invention which carries the DNA segments comprising the DNA vector which is to become part of the desired Product. The Vector Donor comprises a subcloning vector D (or it can be called the cloning vector if the Insert Donor does not already contain a cloning vector) and a segment C flanked by recombination sites (see FIG. 1). Segments C and/or D can contain elements that contribute to selection for the desired Product daughter molecule, as described above for selection schemes. The recombination signals can be the same or different, and can be acted upon by the same or different recombinases. In addition, the Vector Donor can be linear or circular.

Other terms used in the fields of recombinant DNA technology and molecular and cell biology as used herein will be generally understood by one of ordinary skill in the applicable arts.

Recombination Schemes

One general scheme for an in vitro or in vivo method of the invention is shown in FIG. 1, where the Insert Donor and the Vector Donor can be either circular or linear DNA, but is shown as circular. Vector D is exchanged for the original cloning vector B. The Insert Donor need not comprise a vector. The method of the invention allows the Inserts A to be transferred into any number of vectors. According to the invention, the Inserts may be transferred to a particular Vector or may be transferred to a number of vectors in one step. Additionally, the Inserts may be transferred to any number of vectors sequentially, for example, by using the Product DNA molecule as the Insert Donor in combination with a different Vector Donor. The nucleic acid molecule of interest may be transferred into a new vector thereby producing a new Product DNA molecule. The new Product DNA molecule may then be used as starting material to transfer the nucleic acid molecule of interest into a new vector. Such sequential transfers can be performed a number of times in any number of different vectors. Thus the invention allows for cloning or subcloning nucleic acid molecules and because of the ease and simplicity, these methods are particularly suited for high through-put applications. In accordance with the invention, it is desirable to select for the daughter molecule containing elements A and D and against other molecules, including one or more Cointegrate(s). The square and circle are different sets of recombination sites (e.g., lox sites or att sites). Segment A or D can contain at least one Selection Marker, expression signals, origins of replication, or specialized functions for detecting, selecting, expressing, mapping or sequencing DNA, where D is used in this example. This scheme can also be reversed according to the present invention, as described herein. The resulting product of the reverse reaction (e.g. the Insert Donor) may then be used in combination with one or a number of vectors to produce new product molecules in which the Inserts are contained by any number of vectors.

Examples of desired DNA segments that can be part of Element A or D include, but are not limited to, PCR products, large DNA segments, genomic clones or fragments, cDNA clones or fragments, functional elements, etc., and genes or partial genes, which encode useful nucleic acids or proteins. Moreover, the recombinational cloning of the present invention can be used to make ex vivo and in vivo gene transfer vehicles for protein expression (native or fusion proteins) and/or gene therapy.

In FIG. 1, the scheme provides the desired Product as containing A and Vector D, as follows. The Insert Donor (containing A and B) is first recombined at the square recombination sites by recombination proteins, with the Vector Donor (containing C and D), to form a Co-integrate having each of A-D-C-B. Next, recombination occurs at the circle recombination sites to form Product DNA (A and D) and Byproduct DNA C and B). However, if desired, two or more different Co-integrates can be formed to generate two or more Products.

Recombinational cloning using nucleic acid molecules comprising engineered recombination sites, and the materials and methods by which this technique may be accomplished, have been described in detail in U.S. application Ser. No. 08/486,139, filed Jun. 7, 1995 (now abandoned), Ser. No. 08/663,002, filed Jun. 7, 1996 (now U.S. Pat. No. 5,888,732), Ser. No. 09/005,476, filed Jan. 12, 1998, Ser. No. 60/065,930, filed Oct. 24, 1997, Ser. No. 09/177,387, filed Oct. 23, 1998, Ser. No. 60/122,389, filed Mar. 2, 1999, Ser. No. 60/122,392, filed Mar. 22, 1999, Ser. No. 60/126,049, filed Mar. 23, 1999, and Ser. No. 60/136,744, filed May 28, 1999. The disclosures of all of the above-referenced patent applications are incorporated herein by reference in their entireties for their relevant teachings.

Compositions

By the present invention, compositions are provided that may be used in recombinational cloning of nucleic acid molecules or segments thereof. Compositions of the invention may comprise mixtures of at least one ribosomal protein and at least one recombination protein, suitable for use in the recombinational cloning of nucleic acid molecules. The compositions of the invention may comprise two or more, three or more, four or more, five or more, etc., ribosomal proteins, recombination proteins, or combinations thereof. In related embodiments, the compositions may further comprise one or more additional components, such as one or more nucleic acid molecules (including, but not limited to, one or more Insert Donor molecules, one or more Vector Donor molecules, one or more cointegrate molecules, one or more Product molecules and one or more Byproduct molecules), one or more buffer salts, and/or other reagents which may be used in recombinational cloning of nucleic acid molecules. In related aspects, the ribosomal proteins, recombination proteins, and/or compositions of the invention may contain one or more stabilizing compounds (e.g., glycerol, serum albumin or gelatin) that are traditionally included in stock reagent solutions. Suitable amounts of such stabilizing compounds will be familiar to one of ordinary skill in the art, or may be easily determined using only routine experimentation. For example, glycerol may be used in the compositions of the invention at a concentration (vol/vol) of about 5%–75%, about 10%–65%, about 15%–60%, about 20%–55%, about 25%–50%, or about 50%. In an additional related aspect, the invention provides these compositions in ready-to-use concentrations, obviating the time-consuming dilution and pre-mixing steps necessary with previously available solutions.

Ribosomal Proteins

The one or more ribosomal proteins used in the present compositions may be basic ribosomal proteins. By a "basic" ribosomal protein is meant a ribosomal protein that comprises a relatively high percentage (i.e., ranging from about 15–50%) of basic amino acid residues, particularly arginine and lysine. The ribosomal proteins used in the compositions and methods of the invention preferably are no larger than about 14 kilodaltons (kD) in size, and more preferably are about 5 kD to about 14 kD, about 6 kD to about 13 kD, about 7 kD to about 12 kD, or about 8 kD to about 12 kD, in size. According to the invention, the one or more ribosomal proteins may be one or more prokaryotic ribosomal proteins (e.g., one or more bacterial ribosomal proteins) or one or more eukaryotic ribosomal proteins, e.g., one or more ribosomal proteins of animals (such as mammals (including humans), fish, birds, reptiles, amphibians, monotremes, and the like), fungi, plants, and the like. In certain compositions, the ribosomal proteins may be one or more prokaryotic ribosomal proteins, particularly one or more ribosomal proteins obtained from bacteria including, but not limited to, those of the genera *Escherichia, Serratia, Salmonella, Pseudomonas, Bacillus, Streptomyces, Staphylococcus, Streptococcus,* or other gram positive or gram negative bacteria.

In particularly preferred compositions of the invention, the ribosomal proteins may be one or more *Escherichia coli* ribosomal proteins. Particularly preferred such *E. coli* ribosomal proteins for use in the compositions and methods of the invention include, but are not limited to, S10, S14, S15, S16, S17, S18, S19, S20, S21, L21, L23, L24, L25, L27, L28, L29, L30, L31, L32, L33 and L34. Most preferred *E. coli* ribosomal proteins for use in the compositions and methods of the invention are S20, L27 and S15. Corresponding ribosomal proteins from other sources, including prokaryotic or eukaryotic sources, may be used in accordance with the invention. Such corresponding ribosomal proteins preferably correspond (in structure, size, biochemistry, and/or function) to the *E. coli* ribosomal proteins described herein.

Sources and methods for production and isolation of ribosomal proteins, particularly prokaryotic ribosomal proteins, are described in detail in Example 1 below. In addition, information on sources and isolation of prokaryotic and eukaryotic ribosomal proteins may be found in *Ann. Rev. Biochem.* 51:155 (1982); *Ann. Rev. Biochem.* 52:35 (1983); *Ann. Rev. Biochem.* 53:75 (1984); *Ann. Rev. Biochem.* 54:507 (1985); *Ann. Rev. Biochem.* 66:679 (1997); and Bruckner and Cox, *Nucl. Acids Res.* 17(8):3145–3161 (1989).

The amount of one or more ribosomal proteins which is optimal for use in the compositions and methods of the present invention to drive the recombination reaction can be determined using known assays. Specifically, a titration assay may be used to determine the appropriate amount of a purified ribosomal protein, or the appropriate amount of an extract. Such assays are described in detail in the Examples below. In certain embodiments, for example, the compositions may comprise an effective amount of the *E. coli* ribosomal proteins S20 or S15, for example at a concentration range of about 1 ng to about 2500 ng, about 2 ng to about 2000 ng, about 5 ng to about 1500 ng, about 10 ng to about 1500 ng, about 25 ng to about 1500 ng, about 50 ng to about 1500 ng, about 100 ng to about 1500 ng, about 250 ng to about 1500 ng, about 300 ng to about 1500 ng, about 500 ng to about 1500 ng, about 500 ng to about 1250 ng, or about 625 ng to about 1250 ng. In other embodiments, the compositions may comprise the *E. coli* ribosomal protein L27, at a concentration of, for example, about 1,000 ng to about 50,000 ng, about 2,000 ng to about 40,000 ng, about 5,000 ng to about 30,000 ng, about 10,000 ng to about 25,000 ng, about 10,000 ng to about 20,000 ng, or about 10,000 ng. Of course, other concentration ranges for S20, S15, or L27, or other suitable prokaryotic or eukaryotic ribosomal proteins that may be used in the present compositions, may be determined by one of ordinary skill without undue experimentation by carrying out a titration assay as noted above and as described in detail in the Examples below.

Recombination Proteins

In the compositions and methods of the present invention, the exchange of DNA segments is achieved by the use of recombination proteins, including recombinases and associated co-factors and proteins. The one or more recombination proteins for use in the compositions may be any recombination protein, including any prokaryotic or eukaryotic recombination protein, that is suitable for use in recombinational cloning of nucleic acid molecules. Examples of such recombination proteins include, but are not limited to:

Cre

A prokaryotic recombination protein from bacteriophage P1 (Abremski and Hoess, *J. Biol. Chem.* 259(3):1509–1514 (1984)) catalyzes the exchange (i.e., causes recombination) between 34 bp DNA sequences called loxP (locus of crossover) sites (See Hoess et al., *Nucl. Acids Res.* 14(5):2287 (1986)). Cre is available commercially (Novagen, Catalog No. 69247-1). Recombination mediated by Cre is freely reversible. From thermodynamic considerations it is not surprising that Cre-mediated integration (recombination between two molecules to form one molecule) is much less efficient than Cre-mediated excision (recombination between two loxP sites in the same molecule to form two daughter molecules). Cre works in simple buffers with either magnesium or spermidine as a cofactor, as is well known in the art. The DNA substrates can be either linear or supercoiled. A number of mutant loxP sites have been described (Hoess et al., supra). One of these, loxP 511, recombines with another loxP 511 site, but will not recombine with a loxP site.

Integrase

A prokaryotic recombination protein from bacteriophage lambda that mediates the integration of the lambda genome into the *E. coli* chromosome. The bacteriophage λ Int recombinational proteins promote recombination between its substrate all sites as part of the formation or induction of a lysogenic state. Reversibility of the recombination reactions results from two independent pathways for integrative and excisive recombination. Each pathway uses a unique, but overlapping, set of the 15 protein binding sites that comprise att site DNAs. Cooperative and competitive interactions involving four proteins (Int, Xis, IHF and FIS) determine the direction of recombination.

Integrative recombination involves the Int and IHF proteins and sites attP (240 bp) and attB (25 bp). Recombination results in the formation of two new sites: attL and attR. Excisive recombination requires Int, IHF, and Xis, and sites attL and attR to generate attP and attB. Under certain conditions, FIS stimulates excisive recombination. In addition to these normal reactions, it should be appreciated that attP and attB, when placed on the same molecule, can promote excisive recombination to generate two excision products, one with attL and one with attR. Similarly, intermolecular recombination between molecules containing attL and attR, in the presence of Int, IHF and Xis, can result in integrative recombination and the generation of attP and attB. Hence, by flanking DNA segments with appropriate combinations of engineered art sites, in the presence of the appropriate recombination proteins, one can direct excisive or integrative recombination, as reverse reactions of each other.

Each of the aft sites contains a 15 bp core sequence; individual sequence elements of functional significance lie within, outside, and across the boundaries of this common core (Landy, A., *Ann. Rev. Biochem.* 58:913 (1989)). Efficient recombination between the various att sites requires that the sequence of the central common region be identical between the recombining partners, however, the exact sequence is now found to be modifiable. Consequently, derivatives of the att site with changes within the core are now discovered to recombine as least as efficiently as the native core sequences.

Integrase acts to recombine the attP site on bacteriophage lambda (about 240 bp) with the attB site on the *E. coli* genome (about 25 bp) (Weisberg, R. A. and Landy, A. in Lambda II, p. 211 (1983), Cold Spring Harbor Laboratory)), to produce the integrated lambda genome flanked by attL (about 100 bp) and attR (about 160 bp) sites. In the absence of Xis (see below), this reaction is essentially irreversible. The integration reaction mediated by integrase and IHF works in vitro, with simple buffer containing spermidine. Integrase can be obtained as described by Nash, H. A., *Methods of Enzymology* 100:210–216 (1983). IHF can be obtained as described by Filutowicz, M., et al., *Gene* 147:149–150 (1994).

Numerous recombination systems from various organisms can also be used, based on the teaching and guidance provided herein. See, e.g., Hoess et al., *Nucleic Acids Research* 14(6):2287 (1986); Abremski et al., *J. Biol. Chem.* 261(1):391 (1986); Campbell, *J. Bacteriol.* 174(23):7495 (1992); Qian et al., *J. Biol. Chem.* 267(11):7794 (1992); Araki et al., *J. Mol. Biol.* 225(1):25 (1992)). Many of these belong to the integrase family of recombinases (Argos et al. *EMBO J.* 5:433–440 (1986)). Perhaps the best studied of these are the Integrase/att system from bacteriophage λ (Landy, A. (1993) *Current Opinions in Genetics and Devel.* 3:699–707), the Cre/loxP system from bacteriophage P1 (Hoess and Abremski (1990) In *Nucleic Acids and Molecular Biology,* vol. 4. Eds.: Eckstein and Lilley, Berlin-Heidelberg: Springer-Verlag; pp. 90–109), and the FLP/FRT system from the *Saccharomyces cerevisiae* 2μcircle plasmid (Broach et al. *Cell* 29:227–234 (1982)).

Members of the resolvase (Res) family of site-specific recombinases (e.g., γδ, Tn3 resolvase, Hin, Gin, and Cin) are also known, and may be used in accordance with the present invention. Members of this highly related family of recombinases are typically constrained to intramolecular reactions (e.g., inversions and excisions) and can require host-encoded factors. Mutants have been isolated that relieve some of the requirements for host factors (Maeser and Kahnmann (1991) *Mol. Gen. Genet.* 230:170–176), as well as some of the constraints of intramolecular recombination.

Other site-specific recombinases similar to λ Int and similar to P1 Cre can be substituted for Int and Cre. Such recombinases are known. In many cases the purification of such other recombinases has been described in the art. In cases when they are not known, cell extracts can be used or the enzymes can be partially purified using procedures described for Cre and Int.

While Cre and Int are described in detail for reasons of example, many related recombination systems and proteins exist and their application to the described invention is also provided according to the present invention. The integrase family of site-specific recombinases can be used to provide alternative recombination proteins and recombination sites for the present invention, as site-specific recombination proteins encoded by, for example bacteriophage lambda, phi 80, P22, P2, 186, P4 and P1. This group of recombination proteins, which may be used in the present compositions and methods, exhibits an unexpectedly large diversity of sequences. Despite this diversity, all of these recombinases can be aligned in their C-terminal halves. A 40-residue region near the C terminus is particularly well conserved in all the proteins and is homologous to a region near the C terminus of the yeast 2 mu plasmid FLP recombination protein. Three positions are perfectly conserved within this family: histidine, arginine and tyrosine are found at respective alignment positions 396, 399 and 433 within the well-conserved C-terminal region. These residues contribute to the active site of this family of recombinases, and suggest that tyrosine-433 forms a transient covalent linkage to DNA during strand cleavage and rejoining. See, e.g., Argos, P. et al., *EMBO J.* 5:433–40 (1986).

The recombinases of some transposons, such as those of conjugative transposons (e.g., Tn916) (Scott and Churchward. 1995. Ann Rev Microbiol 49:367; Taylor and Churchward, 1997. J Bacteriol 179:1837), may also be used in the compositions and methods of the invention. These transposon recombinases belong to the integrase family of recombinases and in some cases show strong preferences for specific integration sites (Ike et al 1992. J Bacteriol 174:1801; Trieu-Cuot et al, 1993. Mol. Microbiol 8:179).

Alternatively, IS231 and other *Bacillus thuringiensis* transposable elements could be used in accordance with the present invention as recombination proteins and recombination sites. *Bacillus thuringiensis* is an entomopathogenic bacterium whose toxicity is due to the presence in the sporangia of delta-endotoxin crystals active against agricultural pests and vectors of human and animal diseases. Most of the genes coding for these toxin proteins are plasmid-borne and are generally structurally associated with insertion sequences (IS231, IS232, IS240, ISBT1 and ISBT2) and transposons (Tn4430 and Tn5401). Several of these mobile elements have been shown to be active and participate in the crystal gene mobility, thereby contributing to the variation of bacterial toxicity.

Structural analysis of the iso-IS231 elements indicates that they are related to IS1151 from *Clostridium perfringens* and distantly related to IS4 and IS186 from *Escherichia coli*. Like the other IS4 family members, they contain a conserved transposase-integrase motif found in other IS families and retroviruses. Moreover, functional data gathered from IS231A in *Escherichia coli* indicate a non-replicative mode of transposition, with a preference for specific targets. Similar results were also obtained in *Bacillus subtilis* and *B. thuringiensis*. See, e.g., Mahillon, J. et al., *Genetica* 93:13–26 (1994); Campbell, *J. Bacteriol.* 7495–7499(1992).

An unrelated family of recombinases, the transposases, have also been used to transfer genetic information between replicons, and may therefore be used as recombination proteins in accordance with the invention. Transposons arc structurally variable, being described as simple or compound, but typically encode the recombinase gene flanked by DNA sequences organized in inverted orientations. Integration of transposons can be random or highly specific. Representatives such as Tn7, which are highly site-specific, have been applied to the efficient movement of DNA segments between replicons (Lucklow et al. 1993. J. Virol 67:4566–4579).

A related element, the integron, are also tmanslocatable-promoting movement of drug resistance cassettes from one replicon to another. Often these elements are defective transposon derivatives. Transposon Tn21 contains a class I integron called In2. The integrase (IntI1) from In2 is common to all integrons in this class and mediates recombination between two 59-bp elements or between a 59-bp element and an attI site that can lead to insertion into a recipient integron. The integrase also catalyzes excisive recombination. (Hall, 1997. Ciba Found Symp 207:192; Francia et al., 1997. J Bacteriol 179:4419).

Group II introns are mobile genetic elements encoding a catalytic RNA and protein. The protein component possesses reverse transcriptase, maturase and an endonuclease activity, while the RNA possesses endonuclease activity and determines the sequence of the target site into which the intron integrates. By modifying portions of the RNA sequence, the integration sites into which the element integrates can be defined. Foreign DNA sequences can be incorporated between the ends of the intron, allowing targeting to specific sites. This process, termed retrohoming, occurs via a DNA:RNA intermediate, which is copied into cDNA and ultimately into double stranded DNA (Matsuura et al., Genes and Dev 1997; Guo et al, EMBO J, 1997). Numerous intron-encoded homing endonucleases have been identified (Belfort and Roberts, 1997. NAR 25:3379). Such systems can be easily adopted for application to the subcloning methods described herein.

In addition, other suitable recombination proteins are described in detail in U.S. application Ser. No. 08/486,139, filed Jun. 7, 1995 (now abandoned), Ser. No. 08/663,002, filed Jun. 7, 1996 (now U.S. Pat. No. 5,888,732), Ser. Nos. 09/005,476, filed Jan. 12, 1998, 60/065,930, filed Oct. 24, 1997, 09/177,387, filed Oct. 23, 1998, 60/122,389, filed Mar. 2, 1999, 60/122,392, filed Mar. 22, 1999, 60/126,049, filed Mar. 23, 1999, and 60/136,744, filed May 28, 1999, the disclosures of all of which are incorporated herein by reference in their entireties for their relevant teachings. Hence, in preferred compositions of the invention, the recombination protein may be selected from the group consisting of Int, Cre, Res, Xis, FLP, IHF and HU, and may be a site-specific recombination protein. Particularly preferred for use in the present compositions is Int.

The amount of recombination protein which is optimal for use in the compositions and methods of the present invention to drive the recombination reaction can be determined using known assays. Specifically, a titration assay may be used to determine the appropriate amount of a purified recombination protein, or the appropriate amount of an extract. Such assays are described in detail in the Examples below. In certain preferred compositions of the invention, for example, the compositions may comprise an effective amount of λ Int, for example at a concentration range of about 1 ng to about 500 ng, about 2 ng to about 250 ng, about 5 ng to about 200 ng, about 10 ng to about 200 ng, about 25 ng to about 200 ng, about 50 ng to about 200 ng, or about 100 ng to about 200 ng. In addition, the compositions may comprise one or more additional recombination proteins; for example, a composition of the invention may comprise λ Int at the above-indicated concentration ranges, and HU protein and/or IHF protein at concentration ranges of about 1 ng to about 50 ng, about 2 ng to about 25 ng, about 5 ng to about 20 ng, about 5 ng to about 15 ng, or about 5 ng to about 10 ng. Of course, other concentration ranges for λ Int or other recombination proteins that may be used in the present compositions may be determined by one of ordinary skill, without undue experimentation, by carrying out a titration assay as noted above and as described in detail in the Examples below.

Recombinational Cloning Methods

The above-described compositions of the invention are suitable for use in recombination cloning methods that are provided by the present invention. Recombinational cloning using nucleic acid molecules comprising engineered recombination sites, and the materials and methods by which this technique may be accomplished, have been described in detail in U.S. application Ser. No. 08/486,139, filed Jun. 7, 1995 (now abandoned), Ser. No. 08/663,002, filed Jun. 7, 1996 (now U.S. Pat. No. 5,888,732), Ser. Nos. 09/005,476, filed Jan. 12, 1998, 60/065,930, filed Oct. 24, 1997, 09/177,387, filed Oct. 23, 1998, Ser. No. 60/122,389, filed Mar. 2, 1999, 60/122,392, filed Mar. 22, 1999, Ser. No. 60/126,049, filed Mar. 23, 1999, and Ser. No. 60/136,744, filed May 28, 1999. The disclosures of all of the above-referenced patent applications are incorporated herein by reference in their entireties for their relevant teachings.

In one such aspect, the invention relates to such methods comprising:

(a) combining in vitro or in vivo
   (i) one or more Insert Donor molecules comprising one or more desired nucleic acid segments flanked by at least two recombination sites, wherein the recombination sites do not substantially recombine with each other;
   (ii) one or more Vector Donor molecules comprising at least two recombination sites, wherein the recombination sites do not substantially recombine with each other;
   (iii) at least one recombination protein; and
   (iv) at least one ribosomal protein;
(b) incubating the combination formed in step (a) under conditions sufficient to transfer one or more of the desired segments into one or more of the Vector Donor molecules, thereby producing one or more desired Product nucleic acid molecules;

and optionally:

(c) combining in vitro or in vivo
   (i) one or more of the Product molecules comprising the desired segments flanked by two or more recombination sites, wherein the recombination sites do not substantially recombine with each other;
   (ii) one or more different Vector Donor molecules comprising two or more recombination sites, wherein the recombination sites do not substantially recombine with each other;
   (iii) at least one recombination protein; and
   (iv) at least one ribosomal protein; and
(d) incubating the combination formed in step (c) under conditions sufficient to transfer one or more of the desired segments into one or more different Vector Donor molecules, thereby producing one or more different Product molecules.

The invention also relates to such methods which further comprise incubating the different Product molecules with one or more different Vector Donor molecules under conditions sufficient to transfer one or more of the desired segments into the different Vector Donor molecules.

In a related aspect, the invention relates to methods of cloning or subcloning one or more desired nucleic acid molecules by recombinational cloning comprising:

a) combining in vitro or in vivo
   i) one or more Insert Donor molecules comprising one or more nucleic acid segments flanked by two or more recombination sites, wherein the recombination sites do not substantially recombine with each other;
ii) two or more different Vector Donor molecules comprising two or more recombination sites, wherein the recombination sites do not substantially recombine with each other;
iii) at least one recombination protein; and
iv) at least one ribosomal protein; and
b) incubating the combination formed in step (a) under conditions sufficient to transfer one or more of the desired segments into the different Vector Donor molecules, thereby producing two or more different Product molecules.

In another related aspect, the invention relates to methods for recombinational cloning of one or more desired nucleic acid molecules comprising
(a) mixing one or more desired nucleic acid molecules with one or more vectors and with one or more of the compositions of the invention; and
(b) incubating the mixture under conditions sufficient to transfer the one or more desired nucleic acid molecules into one or more of the vectors.

In another related aspect, the invention relates to methods for enhancement of recombinational cloning of nucleic acid molecules, comprising contacting one or more nucleic acid molecules with one or more ribosomal proteins and one or more recombination proteins, or with one or more compositions of the invention, under conditions favoring the recombinational cloning of the one or more nucleic acid molecules.

According to the invention, the one or more ribosomal proteins used in these methods may be one or more prokaryotic or eukaryotic ribosomal proteins, such as those described herein. Similarly, the one or more recombination proteins may be one or more prokaryotic or eukaryotic recombination proteins such as those described herein.

In another related aspect, the invention relates to methods of cloning or subcloning one or more desired nucleic acid molecules by recombinational cloning comprising:
(a) combining in vitro or in vivo
  (i) one or more Insert Donor molecules comprising one or more desired nucleic acid segments flanked by at least two recombination sites, wherein the recombination sites do not substantially recombine with each other;
  (ii) one or more Vector Donor molecules comprising at least two recombination sites, wherein the recombination sites do not substantially recombine with each other; and
  (iii) one or more of the compositions of the invention;
(b) incubating the combination formed in step (a) under conditions to sufficient to transfer one or more of the desired segments into one or more of the Vector Donor molecules, thereby producing one or more desired Product nucleic acid molecules;
and optionally:
(c) combining in vitro or in vivo
  (i) one or more of the Product molecules comprising the desired segments flanked by two or more recombination sites, wherein the recombination sites do not substantially recombine with each other;
  (ii) one or more different Vector Donor molecules comprising two or more recombination sites, wherein the recombination sites do not substantially recombine with each other; and
  (iii) one or more of the compositions of the invention; and
(d) incubating the combination formed in step (c) under conditions sufficient to transfer one or more of the desired segments into one or more different Vector Donor molecules, thereby producing one or more different Product molecules.

In another related aspect, the invention relates to methods of cloning or subcloning one or more desired nucleic acid molecules by recombinational cloning comprising:
a) combining in vitro or in vivo
  i) one or more Insert Donor molecules comprising one or more nucleic acid segments flanked by two or more recombination sites, wherein the recombination sites do not substantially recombine with each other;
  ii) two or more different Vector Donor molecules comprising two or more recombination sites, wherein the recombination sites do not substantially recombine with each other; and
  iii) one or more of the compositions of the invention; and
b) incubating the combination formed in step (a) under conditions sufficient to transfer one or more of the desired segments into the different Vector Donor molecules, thereby producing two or more different Product molecules.

According to the invention, the Insert Donor molecules for use in the compositions and methods of the invention may be derived from genomic DNA or cDNA, or may be produced by chemical synthesis methods. In a related aspect, the Insert Donor molecules may comprise one or more vectors.

The Vector Donor molecules for use in the compositions and methods of the invention may optionally comprise at least one Selectable marker, which allows for the selection of host cells comprising the Product molecules comprising the Selectable markers contributed by the Vector Donor molecules during the recombination reaction. According to this aspect of the invention, the Selectable Marker may be an antibiotic resistance gene, a tRNA gene, an auxotrophic marker, a toxic gene, a phenotypic marker, an antisense oligonucleotide, a restriction endonuclease, a restriction endonuclease cleavage site, an enzyme cleavage site, a protein binding site, and a sequence complementary to a PCR primer sequence. In a related aspect, the Vector Donor molecules may comprise one or more eukaryotic vectors or one or more prokaryotic vectors. Eukaryotic vectors suitable for use in this aspect of the invention may comprise, for example, vectors which propagate and/or replicate in yeast cells, plant cells, fish cells, eukaryotic cells, mammalian cells, and/or insect cells, while suitable prokaryotic vectors may comprise, for example, vectors which propagate and/or replicate in bacteria of the genera *Escherichia* (most particularly *E. coli*), *Salmonella, Bacillus, Streptomyces* or *Pseudomonas*.

The compositions and methods described herein are suitable for use in recombination cloning according to the present invention. However, wild-type recombination sites that are contained in the Insert Donor and/or Vector Donor DNA molecules may contain sequences that reduce the efficiency or specificity of recombination reactions or the function of the Product molecules as applied in methods of the present invention. For example, multiple stop codons in attB, attR, attP, attL and loxP recombination sites occur in multiple reading frames on both strands, so translation efficiencies are reduced, e.g., where the coding sequence must cross the recombination sites, (only one reading frame is available on each strand of loxP and attB sites) or impossible (in attP, attR or attL).

Accordingly, DNA molecules comprising one or more engineered recombination sites are preferably used in the methods of the present invention, to overcome these problems. For example, att sites can be engineered to have one or multiple mutations to enhance specificity or efficiency of the recombination reaction and the properties of Product DNAs (e.g., att1, att2, and att3 sites); to decrease reverse reaction (e.g., removing P1 and H1 from attR). The testing of these mutants determines which mutants yield sufficient recombinational activity to be suitable for recombination subcloning according to the present invention. Hence, in addition to the one or more ribosomal proteins and one or more recombination proteins described herein, the compositions of the invention may further comprise one or more nucleic acid molecules including, but not limited to, one or more Insert Donor molecules, one or more Vector Donor molecules, one or more cointegrate molecules, one or more Product molecules and one or more Byproduct molecules, any or all of which may contain engineered or mutant recombination sites.

Mutations can be introduced into recombination sites for enhancing site specific recombination. The production of DNA molecules comprising one or more mutated engineered recombination sites, which molecules may be used as Insert Donor or Vector Donor molecules in the recombinational cloning methods of the present invention, is described in detail in application Ser. No. 08/486,139, filed Jun. 7, 1995 (now abandoned), Ser. No. 08/663,002, filed Jun. 7, 1996 (now U.S. Pat. No. 5,888,732), Ser. Nos. 09/005,476, filed Jan. 12, 1998, 60/065,930, filed Oct. 24, 1997, 09/177,387, filed Oct. 23, 1998, 60/122,389, filed Mar. 2, 1999, 60/122,392, filed Mar. 22, 1999, 60/126,049, filed Mar. 23, 1999, and 60/136,744, filed May 28, 1999, the disclosures of all of which applications are incorporated herein by reference in their entireties. Particularly preferred for use in the compositions and methods of the present invention are nucleic acid molecules comprising at least one DNA segment having at least two engineered recombination sites flanking a Selectable marker and/or a desired DNA segment, wherein at least one of the recombination sites comprises a core region having at least one engineered mutation that enhances recombination in vitro in the formation of a Cointegrate DNA or a Product DNA.

In accordance with the invention, any vector may be used to construct the Vector Donors used in the methods of the invention. In particular, vectors known in the art and those commercially available (and variants or derivatives thereof) may in accordance with the invention be engineered to include one or more recombination sites for use in the methods of the invention. Such vectors may be obtained from, for example, Vector Laboratories Inc., InVitrogen, Promega, Novagen, NEB, Clontech, Boehringer Mannheim, Pharmacia, EpiCenter, OriGenes Technologies Inc., Stratagene, Perkin Elmer, Pharmingen, Life Technologies, Inc., and Research Genetics. Such vectors may then for example be used for cloning or subcloning nucleic acid molecules of interest. General classes of vectors of particular interest include prokaryotic and/or eukaryotic cloning vectors, expression vectors, fusion vectors, two-hybrid or reverse two-hybrid vectors, shuttle vectors for use in different hosts, mutagenesis vectors, transcription vectors, vectors for receiving large inserts and the like. Particularly preferred vectors (and mutants, derivatives, or variants thereof) that may be used to construct the Vector Donors used in the methods of the invention are described in detail in U.S. application Ser. No. 08/486,139, filed Jun. 7, 1995 (now abandoned), Ser. No. 08/663,002, filed Jun. 7, 1996 (now U.S. Pat. No. 5,888,732), Ser. Nos. 09/005,476, filed Jan. 12, 1998, 60/065,930, filed Oct. 24, 1997, 09/177,387, filed Oct. 23, 1998, 60/122,389, filed Mar. 2, 1999, 60/122,392, filed Mar. 22, 1999, 60/126,049, filed Mar. 23, 1999, and 60/136,744, filed May 28, 1999, the disclosures of all of which applications are incorporated herein by reference in their entireties.

DNA Molecules, Vectors and Host Cells

The invention also relates generally to DNA molecules produced by the methods of the invention, particularly to such DNA molecules which are isolated DNA molecules. Methods for the isolation of DNA molecules produced by the methods of the invention will be familiar to one of ordinary skill in the art, and are described generally in U.S. application Ser. No. 08/486,139, filed Jun. 7, 1995 (now abandoned), Ser. No. 08/663,002, filed Jun. 7, 1996 (now U.S. Pat. No. 5,888,732), Ser. Nos. 09/005,476, filed Jan. 12, 1998, 60/065,930, filed Oct. 24, 1997, 09/177,387, filed Oct. 23, 1998, 60/122,389, filed Mar. 2, 1999, 60/122,392, filed Mar. 22, 1999, 60/126,049, filed Mar. 23, 1999, and 60/136,744, filed May 28, 1999, the disclosures of which are incorporated herein by reference in their entireties. In addition, the isolated DNA molecules of the invention may be inserted into standard nucleotide vectors suitable for transfection or transformation of a variety of prokaryotic (bacterial) or eukaryotic (yeast, plant or animal including human and other mammalian) host cells. Vectors suitable for these purposes, and methods for insertion of DNA fragments therein, will be well-known to one of ordinary skill in the art. Thus, the present invention also relates to vectors comprising such DNA molecules, and to host cells comprising such DNA molecules and/or vectors.

Kits

The invention also relates to kits for use in recombinational cloning of a nucleic acid molecule. Kits according to the present invention may comprise a carrying means being compartmentalized to receive in close confinement therein one or more containers such as vials, tubes, bottles, ampules and the like. Each of such containers may comprise components or a mixture of components needed to perform recombinational cloning of nucleic acid molecules, particularly according to the methods of the present invention.

In one such aspect, the kits of the invention may comprise at least one ribosomal protein and at least one recombination protein. Ribosomal proteins and recombination proteins suitable for use in the kits of the invention include, but are not necessarily limited to, those prokaryotic and eukaryotic ribosomal and recombination proteins described in detail herein. Of course, it is also possible to combine one or more of these components into a single container, such that the kit will contain one or more containers wherein a first container contains at least one ribosomal protein and at least one recombination protein, or wherein a first container contains one or more of the above-described compositions of the invention. Additional kits of the invention may comprise one or more additional containers containing additional components which may be useful in carrying out recombinational cloning of nucleic acid molecules, including, for example, one or more polymerases (such as one or more thermostable DNA polymerases like Taq, Tne, Tma, and the like), one or more polypeptides having reverse transcriptase activity (such as RSV or ASLV reverse transcriptases, particularly those that are substantially reduced in RNase H activity), one or more restriction endonucleases, one or more buffers, one or more detergents, and the like.

Applications

There are a number of applications for the compositions, methods and kits of the present invention. These uses include, but are not limited to, changing vectors, operably linking genes to regulatory genetic sequences (e.g., promoters, enhancers, and the like), constructing genes for fusion proteins, changing copy number, changing replicons, cloning into phages, and cloning, e.g., PCR products (with an attB site at one end and a loxP site at the other end), genomic DNAs, and cDNAs. Such applications are described in detail, for example, in U.S. application Ser. No. 08/486,139, filed Jun. 7, 1995 (now abandoned), Ser. No. 08/663,002, filed Jun. 7, 1996 (now U.S. Pat. No. 5,888,732), Ser. Nos. 09/005,476, filed Jan. 12, 1998, 60/065,930, filed Oct. 24, 1997, 09/177,387, filed Oct. 23, 1998, 60/122,389, filed Mar. 2, 1999, 60/122,392, filed Mar. 22, 1999, 60/126,049, filed Mar. 23, 1999, and 60/136,744, filed May 28, 1999, which was filed on Oct. 23, 1998, the disclosures of all of which applications are incorporated herein by reference in their entireties.

It will be understood by one of ordinary skill in the relevant arts that other suitable modifications and adaptations to the methods and applications described herein are readily apparent and may be made without departing from the scope of the invention or any embodiment thereof. Having now described the present invention in detail, the same will be more clearly understood by reference to the following examples, which are included herewith for purposes of illustration only and are not intended to be limiting of the invention.

EXAMPLES

The present recombinational cloning methods accomplish the exchange of nucleic acid segments to render something useful to the user, such as a change of cloning vectors. These segments must be flanked on both sides by recombination signals that are in the proper orientation with respect to one another. In the examples below the two parental nucleic acid molecules (e.g., plasmids) are called the Insert Donor and the Vector Donor. The Insert Donor contains a segment that will become joined to a new vector contributed by the Vector Donor. The recombination intermediate(s) that contain(s) both starting molecules is called the Cointegrate(s). The second recombination event produces two daughter molecules, called the Product (the desired new clone) and the Byproduct.

Buffers

Various known buffers can be used in the reactions of the present invention. For restriction enzymes, it is advisable to use the buffers recommended by the manufacturer. Alternative buffers can be readily found in the literature or can be devised by those of ordinary skill in the art. One exemplary buffer for lambda integrase is comprised of 50 mM Tris-HCl, at pH 7.5–7.8, 70 mM KCl, 5 mM spermidine, 0.5 mM EDTA, and 0.25 mg/ml bovine serum albumin, and optionally, 10% glycerol. Suitable buffers for other site-specific recombinases which are similar to lambda Int are either known in the art or can be determined empirically by the ordinarily skilled artisan, particularly in light of the above-described buffers.

Example 1

Stimulation of Integrase by E. coli Ribosomal Proteins

Materials and Methods

DNAs for Recombination Assays

Figure 2:
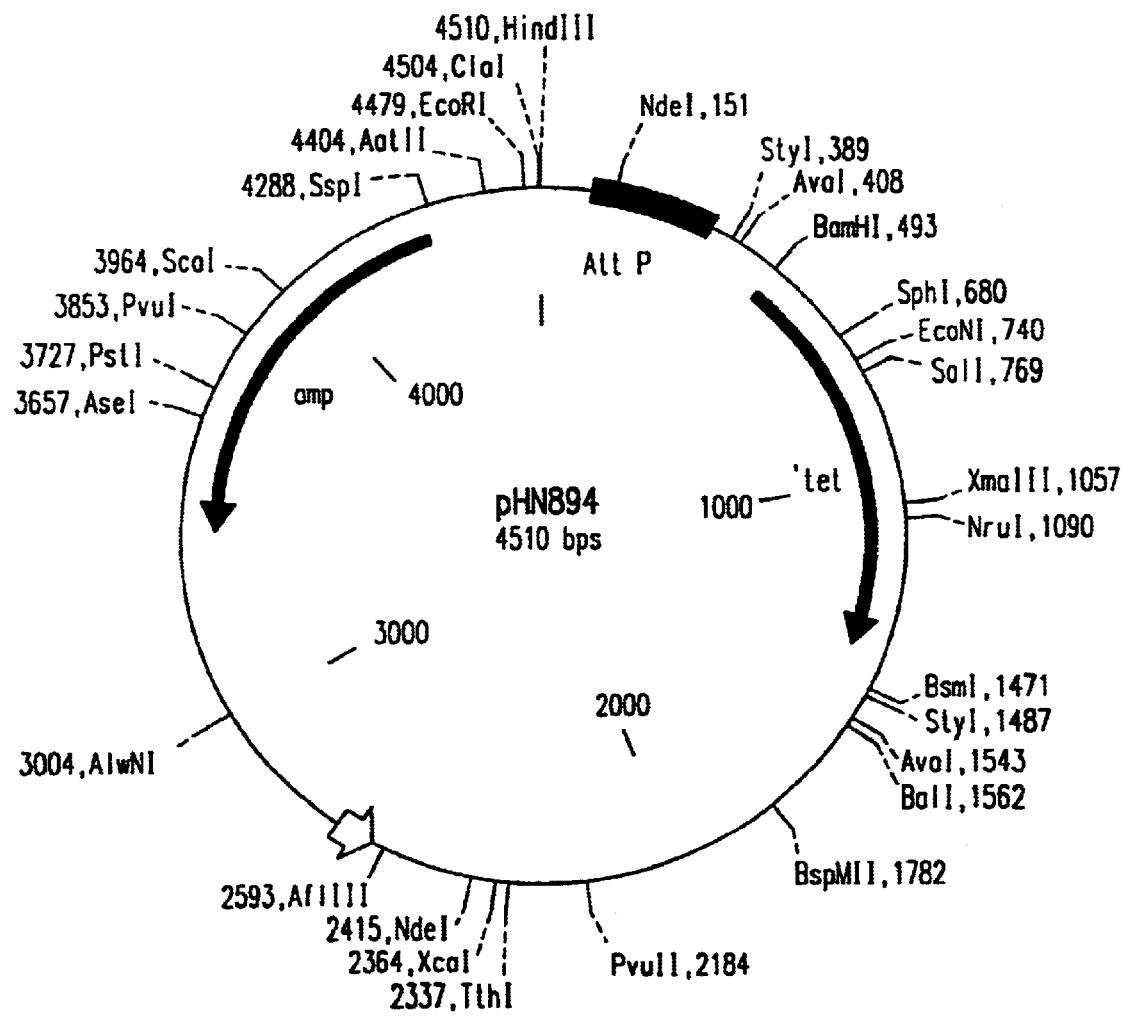
FIG. 2 depicts a restriction map for plasmid pHN894. AtP: attP attachment site; 'tet: truncated tetracycline resistance gene; amp: β-lactamase gene.
Figure 3:
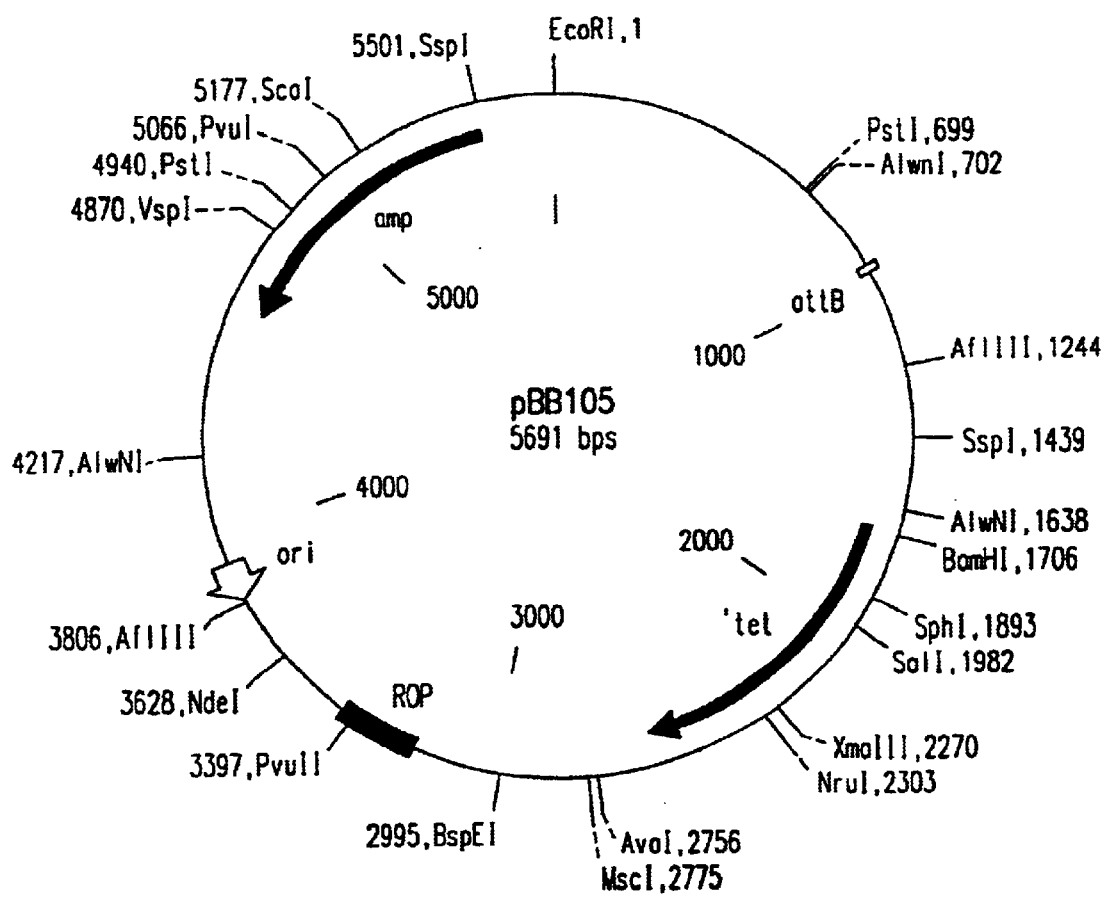
FIG. 3 depicts a restriction map for plasmid pBB105. attB: attB attachment site; 'tet: truncated tetracycline resistance gene; amp: β-lactamase gene; ori: colE1 origin of replication; ROP: replication control site.
Figure 4:
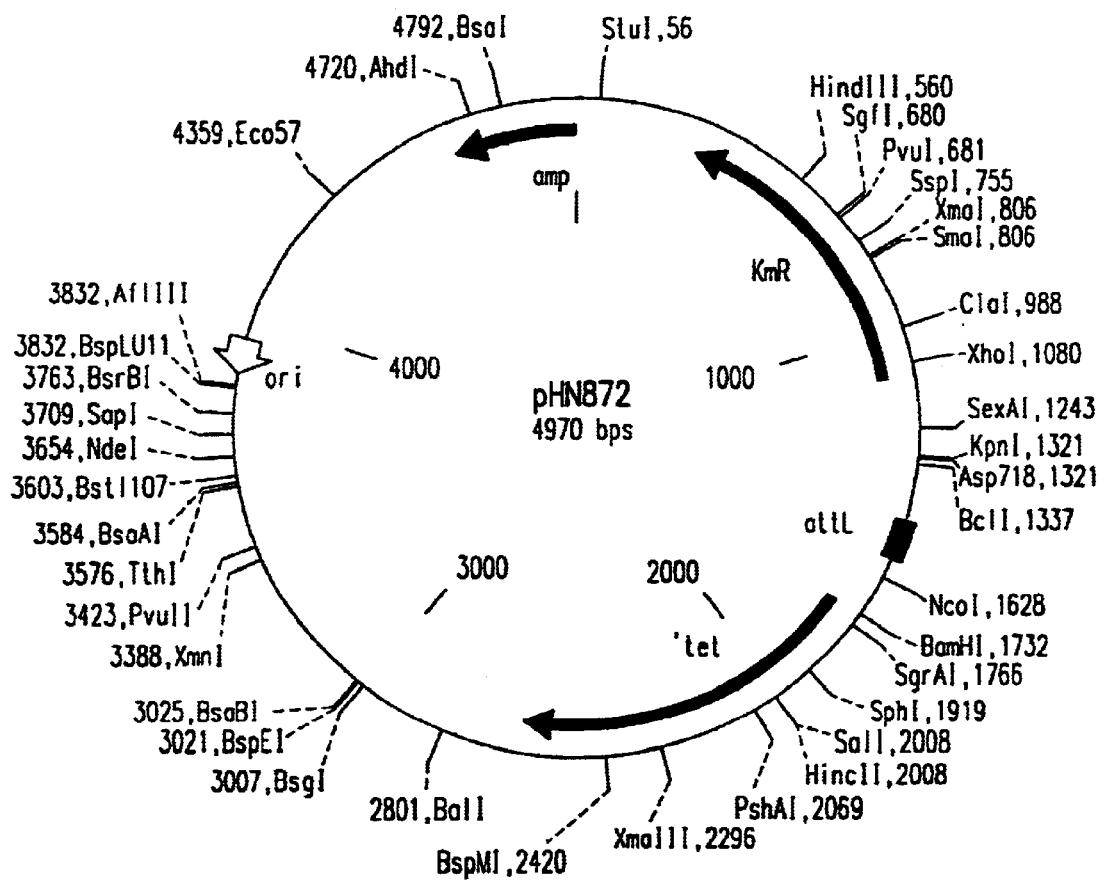
FIG. 4 depicts a restriction map for plasmid pHN872. attL: attL attachment site; 'tet: truncated tetracycline resistance gene; 'amp: truncated β-lactamase gene; ori: colE1 origin of replication; KmR: kanamycin resistance gene.
Figure 5:
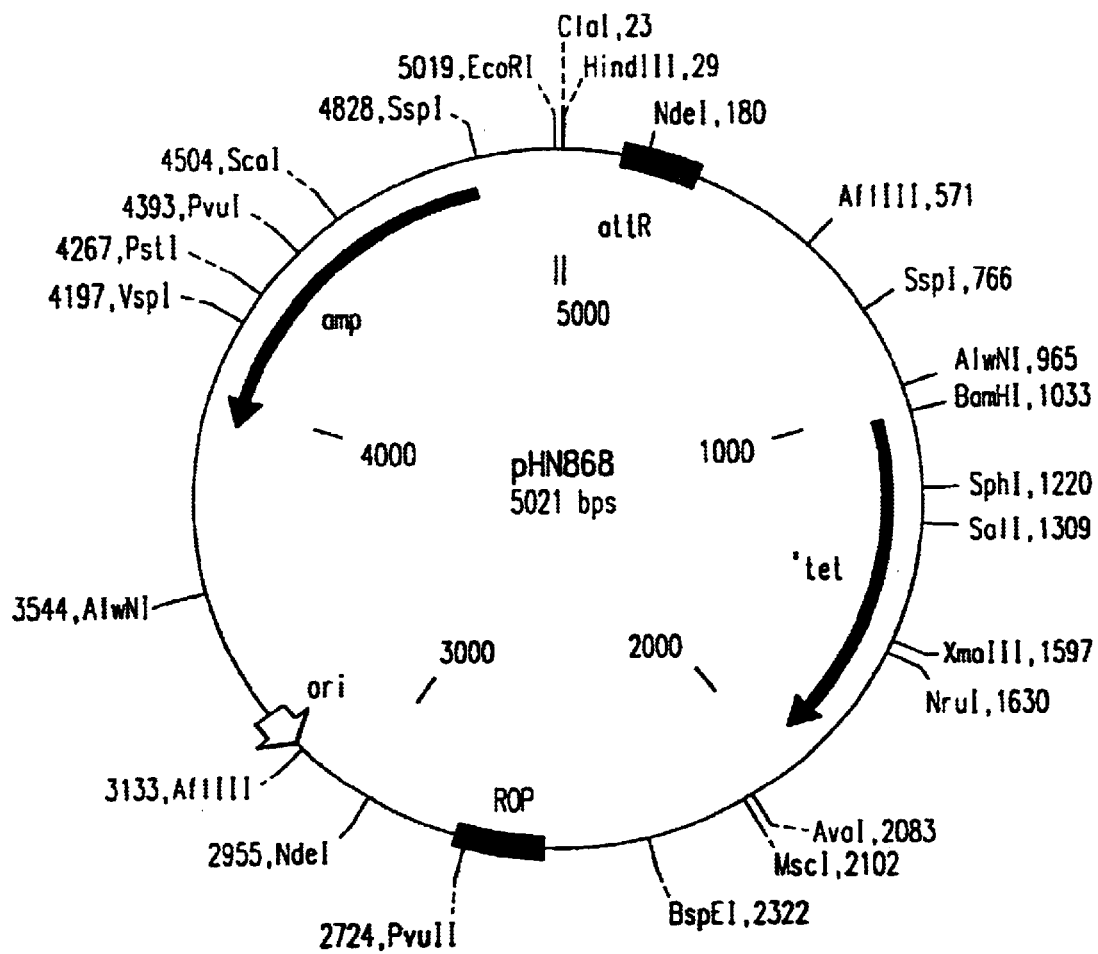
FIG. 5 depicts a restriction map for plasmid pHN868. attR: attR attachment site; 'tet: truncated tetracycline resistance gene; amp: β-lactamase gene; ori: colE1 origin of replication; ROP: replication control site.

Plasmid pHN894 (FIG. 2), bearing an attP site, and plasmid pBB105 (FIG. 3), bearing an attB site, are described (Kitts, P. A. and Nash, H. A. *J. Mol. Biol.* 204: 95–107 (1988); Nash, H. A. *Methods Enz.* 100: 210–216 (1983)). pBB105 was cut with EcoRI before use. Plasmid pHN872 (FIG. 4), bearing an attL site, and plasmid pHN868 (FIG. 5), bearing an attR site, are described (Kitts, P. A. and Nash, H. A. *J. Mol. Biol.* 204:95–107 (1988)). pHN872 was cut with SalI before use. These plasmids were propagated in *E. coli* strain DH10B. To grow cells for preparation of plasmid DNA, the growth medium contained in one liter: 12 g of tryptone, 24 g of yeast extract, 2.3 g of $KH_2PO_4$, 12.5 g of $K_2HPO_4$, 0.01% (v/v) PPG antifoam, and appropriate antibiotic. Cells from a glycerol seed were placed in 25 ml of medium containing 100 µg/ml ampicillin (pBB105, pHN894, pHN868) or 100 µg/ml kanamycin (pHN872) and grown overnight at 37° C. Fifteen ml of overnight culture was added to 1.5 L medium containing 10 µg/ml appropriate antibiotic and cells were grown to a $A_{600}$ of ~2.0. Chloramphenicol was then added to a final concentration of 170 µg/ml and growth was continued for 16 hr at 37° C. Cells were harvested by centrifugation and stored at –70° C. Plasmid DNAs were purified as follows. Frozen cells were thawed on ice and suspended in 7 ml/g cells of 25 mM Tris-HCl (pH 8.0), 10 mM EDTA, and 50 mM glucose (TEG)+100 µg/ml of RNaseA+1 mg/ml lysozyme. A solution of 1% (w/v) SDS-0.125 N NaOH at 14 ml/g cells was then added to lyse cells. After 10 minutes on ice, 7.5 M ammonium acetate at 10.5 ml/g cells was added. After 10 minutes on ice, the mixture was centrifuged at 28,000×g for 10 minutes and the supernatant was collected. DNA was precipitated by addition of 0.6 volumes of cold isopropanol, and DNA was pelleted by centrifugation at 28,000×g for 10 minutes. The DNA pellet was dissolved in 10 mM Tris-HCl (pH 7.5)-1 mM EDTA ($T_{10}E_1$)+RNase A (100 µg/ml)+ RNaseT1 (1,200 U/ml). After phenol extraction and ethanol precipitation of the DNA, it was dissolved in $T_{10}E_1$. The DNA was dialyzed against 100 volumes of 10 mM Tris-HCl (pH 7.5), 1 mM EDTA, and 450 mM NaCl ($T_{10}E_1N_{450}$) overnight. The dialyzed DNA was applied to a NACS-37 column (LTI) equilibrated in $T_{10}E_1N_{450}$. The column was washed with 10 column volumes of $T_{10}E_1N_{450}$ and eluted with a 15-column volume linear gradient from 0.45 M to 0.65 M NaCl in $T_{10}E_1$. Fractions were analyzed by agarose gel electrophoresis and those containing supercoiled DNA were pooled. The pooled DNA was dialyzed against $T_{10}E_1$ and stored at –20° C.

Figure 6:
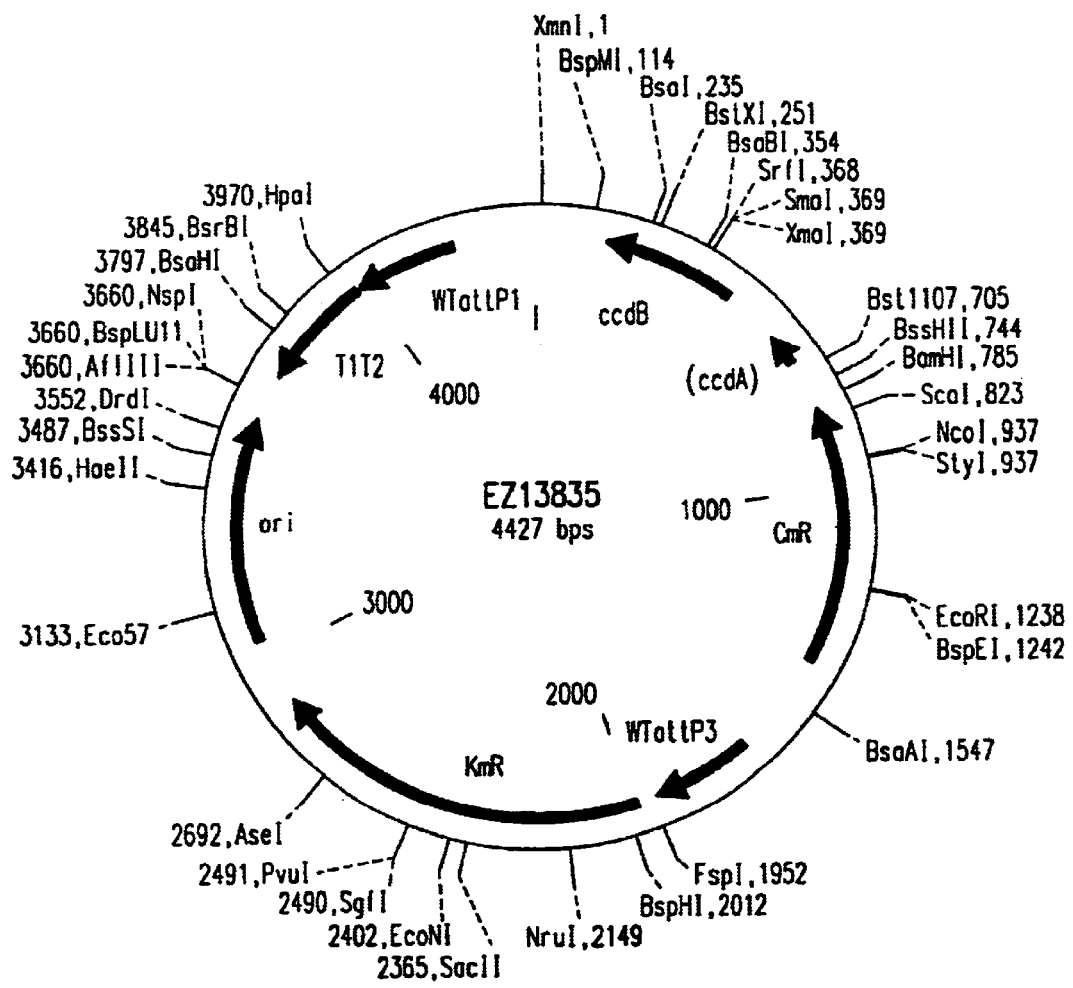
FIG. 6 depicts a restriction map for plasmid pEZ13835. WTattP1: modified attP attachment site; WTattP3: modified attP attachment site; T1T2: transcription terminators; KmR: kanamycin resistance gene; CmR: chloramphenicol resistance gene; ccdB: death gene; ori: colE1 origin of replication.
Figure 7:
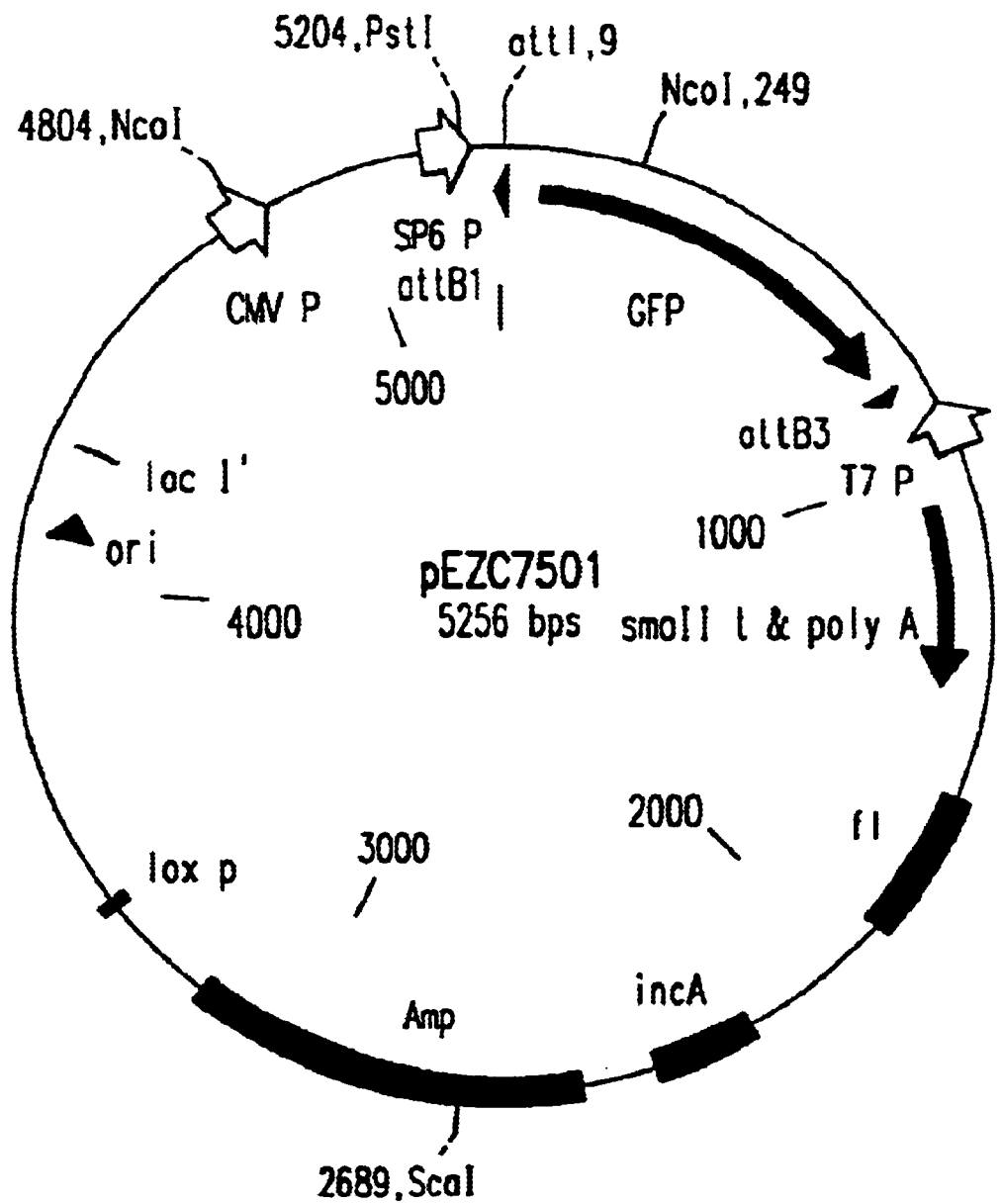
FIG. 7 depicts a restriction map for plasmid pEZC7501. attB1: modified attB attachment site; attB3: modified attB attachment site; GFP: truncated green flourescent protein gene; T7 P: T7 promoter; SP6 P: SP6 promoter; CMV P: CMV promoter; lacI': lac I promoter; lox p: cre recombination site; small t & poly A: SV40 small tumor antigen intron and poly A signal; fl: fl intergenic region; incA: phage P1 incompatibility locus; Amp: β-lactamase gene; ori: colE1 origin of replication.
Figure 8:
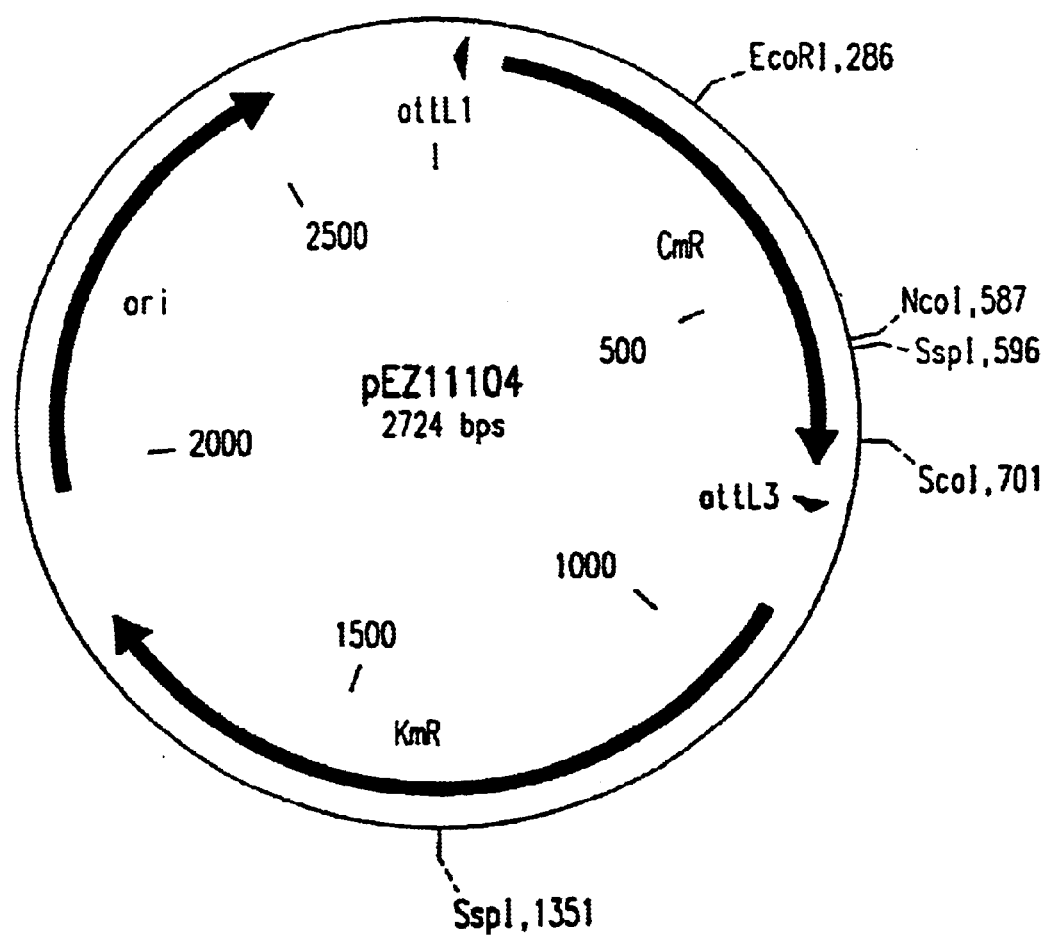
FIG. 8 depicts a restriction map for plasmid pEZ1104. attL1: modified attL attachment site; attL3: modified attL attachment site; CmR: chloramphenicol resistance gene; KmR: kanamycin resistance gene; ori: colE1 origin of replication.
Figure 9:
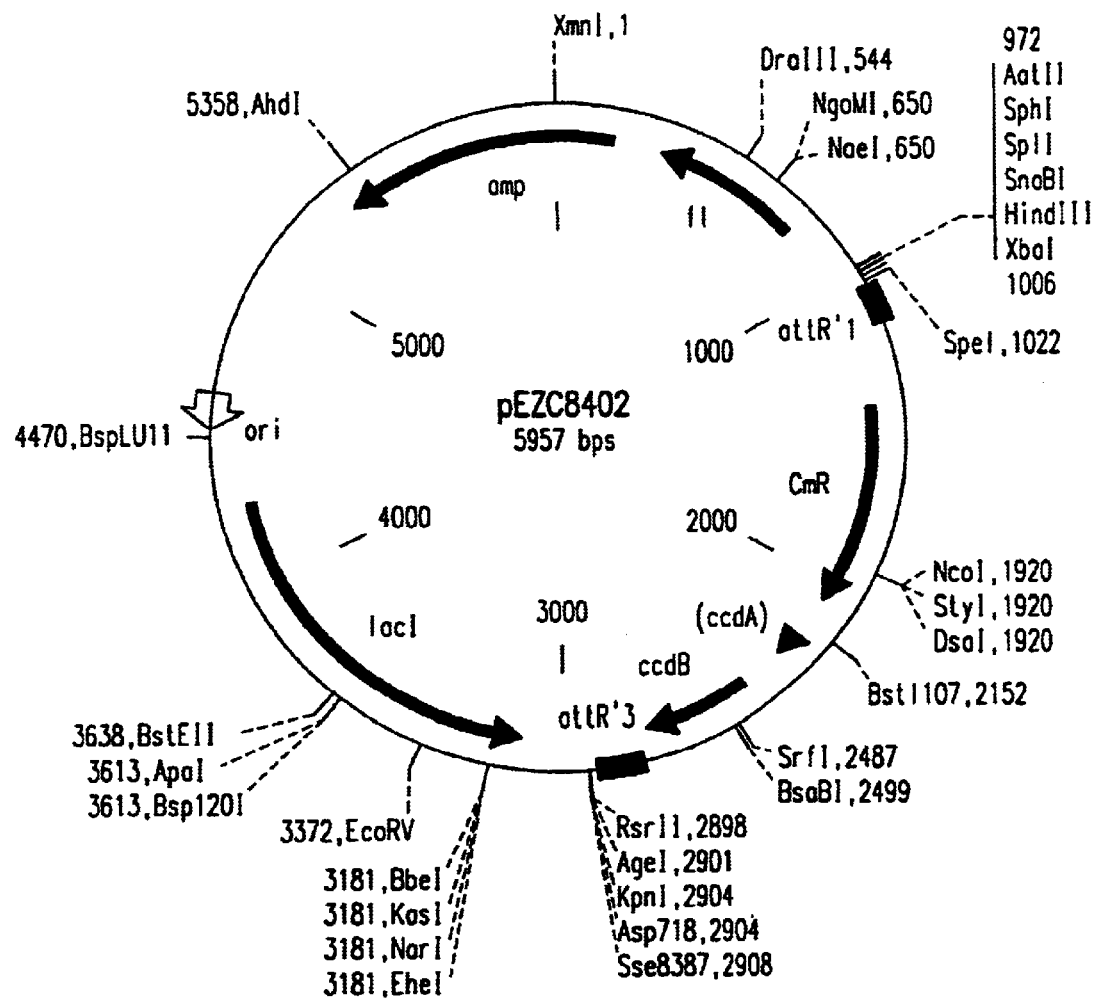
FIG. 9 depicts a restriction map for plasmid pEZC8402. attR'I: modified attR attachment site; attR'3: modified attR attachment site; lac I: lac repressor gene; amp: β-lactamase gene; ori: colE1 origin of replication; CmR: chloramphenicol resistance gene; fl: fl intergenic region; ccdB: death gene.

Plasmid pEZ13835 FIG. 6; attP), pEZC7501 (FIG. 7; attB), pPZ11104 (FIG. 8; attR), and pEZC8402 (FIG. 9; attL) were as shown. pEZC7501 was cut with ScaI and pEZC8402 with NcoI before use. pEZ13935 and pEZC8402 were propagated in *E. coli* DB2 and the other two in *E. coli* DH5α. Cells from a glycerol seed were placed in 25 ml of CIRCLEGROW® brand culture medium (BIO 101) plus 100 mg/ml ampicillin (pEZC7501 and pEZC8402) or plus 100 mg/ml kanamycin (pEZ13835 and pEZ11104) and grown overnight at 37° C. Cells were harvested by centrifugation and stored at –70° C. Plasmid DNAs were purified using Qiagen Midi products and protocols.

SDS PAGE

Tris-Tricine SDS PAGE 16% precast mini gels (Novex) were used to analyze protein samples. The samples were prepared by mixing with an equal volume of 0.9 M Tris-HCl (pH 8.45), 24% (v/v) glycerol, 8% (w/v) SDS, 0.015% (w/v) Coomassie BlueG, 0.005% (w/v) Phenol Red, and 0.05 M dithiothreitol and boiling for 3 to 5 min. Gels were run at 125 volts in 0.1 M Tris-Tricine (pH 8.3)-0.1% (w/v) SDS for 90 min. Gels were stained in 50% (v/v) methanol, 10% (v/v) acetic acid, and 1 mg/ml Coomassie Blue R-250 solution followed by destaining in 20% (v/v) methanol, 10% (v/v) acetic acid solution.

Determination of Protein Concentration

S20, Int, and Xis bind Bradford reagent dye poorly, so that the Bradford procedure was not used to determine protein concentration. Rather, for Int and Xis, protein concentration was estimated by comparison to Coomassie Blue-stained band intensities of a know amount of BenchMark protein standard of a similar size run along with Int or Xis on an SDS gel. For S20, protein concentration was established using an extinction coefficient at 278 nm of $0.140 \times 10^4$ $M^{-1}cm^{-1}$ (*Eur. J. Biochem.* 126: 299–309 (1982)).

PCR

PCR reaction mixtures (50 μl) contained 22 mM Tris-HCl (pH 8.4), 55 mM KCl, 1.65 mM $MgCl_2$, 200 μM each of dATP, dCTP, dTTP, and dGTP, 1 μM of each primer, 300 ng of DNA template, and 1.1 units of Taq DNA polymerase. Initial template denaturation was at 95° C. for 5 minutes.

Purification of IHF

The strain used for overproduction of IHF is described (Nash, H. A. et. al. *J. Bacteriol.* 169: 4121–4127 (1987)). IHF was purified as described (Rice, P. A. et. al. *Cell* 87: 1295–1306 (1996)).

Purification of Native Int

Native Int was purified from *E. coli* strain HN695 (Lange-Gustafson, B. J. and Nash, H. A. *J. Biol. Chem.* 259:12724–12732 (1984)) by a modification of published procedures (Nash, H. A. *Methods Enz.* 100:210–216 (1983)).

Growth of Cells

Cells from a glycerol stock of strain HN695 were inoculated into 50 ml of LB broth containing 25 μg/ml ampicillin in a 250-ml flask. The culture was grown at 31° C. in an air shaker to an $A_{650}$ of 0.6 to 1.4. This seed culture was used to inoculate six 2.8-L flasks containing 500 ml of growth medium each and cells were grown as just stated. These cultures were used to inoculate 360 L of growth medium in a 500-L fermentor. Cells were grown at 31° C. with aeration (190 rpm) and agitation (200 rpm) to an $A_{650}$ of 0.65, and were harvested in a chilled centrifuge. Cell paste (~400 g) was brought to 600 ml by addition of ice-cold 50 mM Tris-HCl (pH 7.5) containing 10% (w/v) sucrose and homogenized in a Waring blender at low speed. The slurry was divided into 40-ml aliquots, frozen in dry ice, and stored at −70° C.

Preparation of Extract

Three tubes of frozen cells (60 g) were thawed at room temperature and placed on ice. To each tube, 2 ml of a 10 mg/ml solution of lysozyme in 250 mM Tris-HCl (pH 7.5) was added, and the tubes were mixed thoroughly. After 35 min on ice, the mixture was centrifuged at 32,600×g for 45 min. The supernatant was retained (57 ml).

Differential Salt Precipitation

The supernatant was diluted with 50 mM Tris-HCl (pH 7.5) to 100 ml and centrifuged at 4° C. and 41,000 rpm (170,000×g) for 200 min in a precooled Sorval T865 rotor. The supernatant was decanted, frozen, and stored at −70° C. The pellet was stored at −70° C. Thawed pellet was resuspended with the aid of a Teflon pestle in Buffer X (50 mM Tris-HCl (pH 7.5), 1 mM EDTA, 1 mM β-mercaptoethanol, and 10% (w/v) glycerol)+0.6 M KCl. After adjusting to a volume of 50 ml with the same buffer, the mixture was stirred at 4° C. for 1 hr and centrifuged in a Sorval T865 rotor as before. The clear, straw-colored supernatant was carefully removed, frozen in dry ice, and stored at −70° C.

Phosphocellulose Chromatography

After thawing, the second supernatant was loaded at 38 cm/hr on a 4.5-ml phosphocellulose column (Whatman P-11) equilibrated in Buffer X+0.6 M KCl and the column was washed with 5 column volumes of Buffer X+0.6 M KCl. The column was developed with a 10-column volume linear gradient of Buffer X+0.6 M KCl to Buffer X+1.7 M KCl at 19 cm/hr. Int-containing fractions eluting between 0.7 and 1.1 M KCl were pooled and stored at −70° C.

Hydroxyapatite Chromatography

The phosphocellulose pool was loaded at 38 cm/hr on a 1.5-ml hydroxyapatite column (Bio-Rad, ceramic, type II) equilibrated in Buffer X+0.6 M KCl. The pool was diluted with Buffer X to match the ionic strength of Buffer X+0.6 M KCl before loading. The column was washed with buffer X+1 M KCl. Int was eluted at 19 cm/hr with a 10-column volume linear gradient of Buffer X+0.6 M KCl to Buffer X+0.6 M KCl+0.025 M $KPO_4$. Int-containing fractions were pooled, BSA was added to 2 mg/ml, and the pool was frozen at −70° C.

Purification of Stimulatory Protein as a Side Fraction of a Native Int Preparation Cells were grown and harvested and cell extract was prepared as described in the Materials and Methods section Purification of Native Int. The clarified cell extract (~60 ml) was diluted to 100 ml with Buffer X (see section: Purification of Native Int) and centrifuged at 4° C. at 41,000 rpm in a Sorval T865 rotor for 200 min. The supernatant was divided into 25 ml aliquots in 50 ml conical tubes and submerged into a boiling water bath for 30 minutes. The heated suspension was centrifuged at 27,000×g for 45 minutes. The supernatant was collected and diluted with Buffer X+1.7 M KCl to match the ionic strength of Buffer X+0.6 M KCl and loaded at 15 cm/hr onto a 18 ml phosphocellulose (Whatman P-11) column (1.6×9 cm) which had been equilibrated in Buffer X+0.6 M KCl. The column was washed with 10 column volumes of Buffer X+0.6 M KCl and developed with a 10-column volume linear gradient of Buffer X+0.6 M KCl to Buffer X+1.7 M KCl. Fractions were stored at −70° C. SDS PAGE analysis of aliquots of the fractions revealed a single protein band migrating with an apparent molecular weight of 11 kDa. The protein eluted at 1.2 M KCl. Fractions containing the 11-KDa protein were pooled and diluted with Buffer X to match the ionic strength of Buffer X+0.2 M KCl. The diluted pool was loaded at 76 cm/hr onto a 1 ml Mono S column (Pharmacia) equilibrated in Buffer X+0.2 M KCl. The protein was eluted with Buffer X+1.0 M KCl. Fractions containing the peak of 11-KDa protein were pooled and stored at −70° C. The protein was subjected to amino-terminal amino acid sequence analysis as described in Materials and Methods section Amino-Terminal Amino Acid Sequence Analysis of Stimulatory Proteins and found to be ribosomal protein S20.

Purification of Stimulatory Proteins from Cells Producing Native Int

Cells were grown and harvested as described in Materials and Methods section Purification of Native Int. Cell slurry (60 g cells) was thawed at room temperature and placed on ice. A 20 mg/ml solution of lysozyme in 250 mM Tris-HCl (pH 7.4) was added in a volume 1/20 the volume of cells. After 40 minutes on ice with occasional mixing, KCl was added to a final concentration of 0.6 M. The slurry was divided into 25 ml aliquots in 50 ml conical tubes and submerged in a 72° C. water bath for 25 minutes. The suspension was spun at 27,000×g for 45 minutes. The supernatant was loaded at 15 cm/hr onto a 10 ml phosphocellulose column (Whatman P-11) (1.6×5 cm) equilibrated in Buffer X+0.6 M KCl. The column was washed with 10 column volumes of Buffer X+0.6 M KCl and developed with a 10-column volume linear gradient of Buffer X+0.6 M KCl to 1.7 M KCl. The fractions were assayed for ability to stimulate λ integrase activity (see Materials and Methods section Integrative Recombination Gel Assay). Two peaks of stimulating activity were found. Two pools were made, from fractions eluting at ~0.8 M KCl (Pool 1) and from fractions eluting at ~1.2 M KCl (Pool 2), and stored at −70° C.

The pools were processed separately on Mono S. Each pool was diluted with Buffer X to match the ionic strength of Buffer X+0.2 M KCl and loaded at 76 cm/hr onto a 1 ml Mono S column (Pharmacia) equilibrated with Buffer X+0.2 M KCl. The column was washed with 10 column volumes of Buffer X+0.2 M KCl and developed with a 20-column volume linear gradient of Buffer X+0.2 M KCl to Buffer X+1.7 M KCl. Fractions were stored at −70° C.

Figure 18:
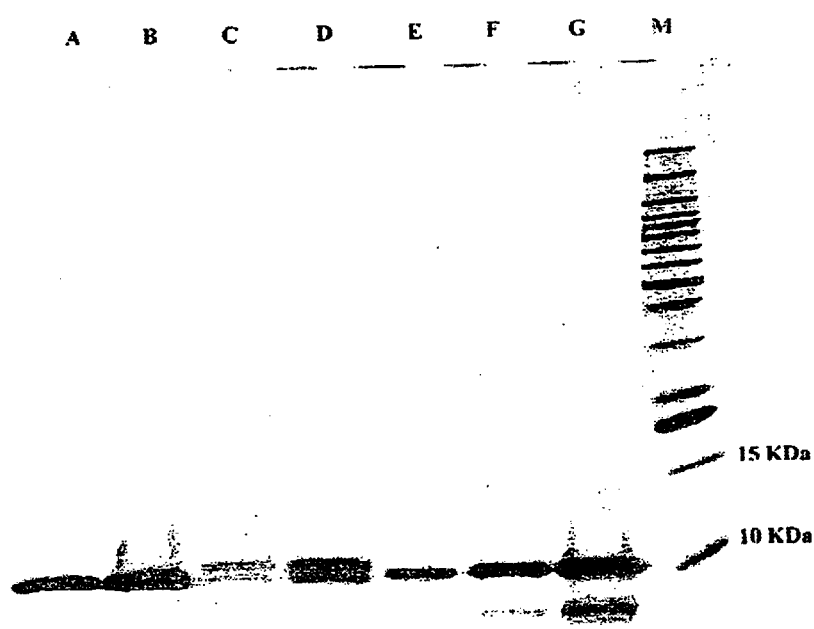
FIG. 18 is a photograph of an SDS-PAGE gel of peak fractions containing integrative recombination stimulatory activity from the Mono S columns described in Materials and Methods section Purification of Stimulatory Proteins from Cells producing Native Int and Results section PART II: Purification and Identification of the Stimulatory Proteins. Phosphocellulose Pool #1 was fractionated on a Mono S column producing two peaks of activity at fraction 18 (1 and 2 μl, lanes A and B) and fraction 22 (1 and 2 μl, lanes C and D). Phosphocellulose Pool #2 was fractionated in a second run on the same Mono S column producing one peak of activity at fraction 24 (1 and 2 μl, lanes F and G). S20 was run in lane E and BenchMark protein standard in lane M.

The fractions from each column were assayed for ability to stimulate λ integrase activity. Pool 1 from phosphocellulose was fractionated into two activity peaks by Mono S. The primary protein band in the first peak (FIG. 18, lanes A and B) was determined by N-terminal amino acid sequence analysis to be ribosomal protein L27 (see Materials and Methods section Amino-Terminal Amino Acid Sequence Analysis of Stimulatory Proteins). The second peak eluting later in the gradient was found to be composed of two major protein bands by SDS PAGE analysis (FIG. 18, lanes C and D). One protein co-migrated with L27 and the other migrated more slowly than L27 and S20 (lane E). Pool 2 from phosphocellulose was fractionated into one peak of activity by Mono S which eluted at a slightly higher salt concentration than the second peak of Pool 1 on Mono S. The main protein in this activity peak co-migrated during SDS-PAGE analysis with S20 protein (FIG. 18, lanes F and G).

Amino-Terminal Amino Acid Sequence Analysis of Stimulatory Proteins

Protein samples were subjected to SDS PAGE as described in Materials and Methods section SDS PAGE. The gel was equilibrated in transfer buffer (0.05 M Tris, 0.04 M boric acid, 0.5 mM EDTA, 20% (v/v) methanol (pH 8.4)). PVDF membrane (Immobilon P from Millipore) was prepared according to manufacturer's instructions and equilibrated in transfer buffer. The protein was transferred to the membrane using a BioRad mini blotting apparatus at 100 volts for 1 hour. The membrane was stained with Coomassie Blue R-250 staining solution and destained in 100% (v/v) methanol. The membrane was air dried and the stained protein band was excised from the membrane and stored in a 1.5-ml microcentrifuge tube.

Amino-terminal amino acid sequence analysis was performed on membrane bound protein samples by automated Edman sequence analysis by the HHMI Biopolymer Laboratory, W.M. Keck Foundation, New Haven, Conn.

Cloning of Int-His$_6$

Figure 10:
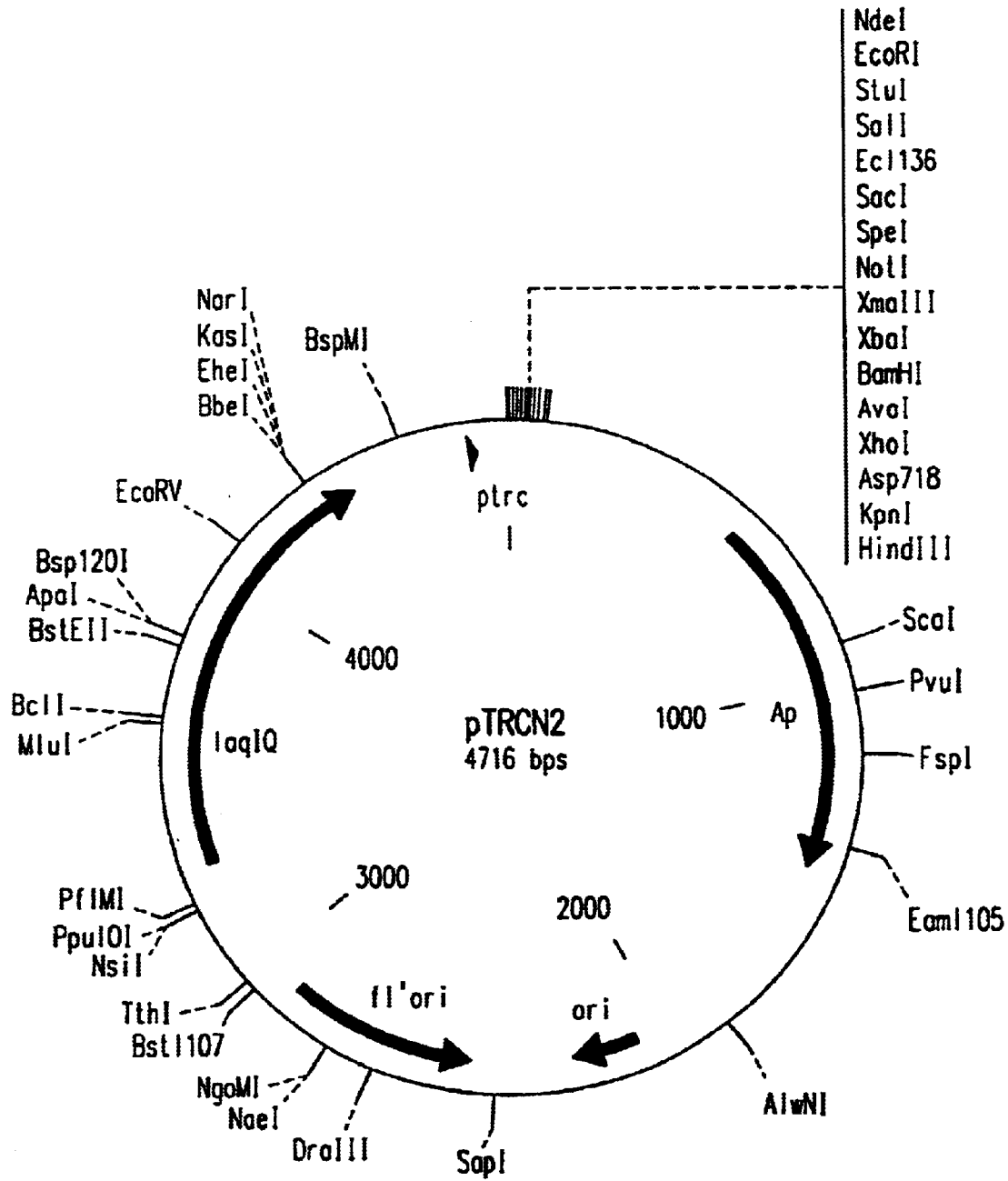
FIG. 10 depicts a restriction map for plasmid pTRCN2. Ap: β-lactamase gene; ptrc: trc promoter; laqI$^Q$: lac repressor gene; fl'ori: fl intergenic region; ori: colE1 origin of replication.
Figure 11:
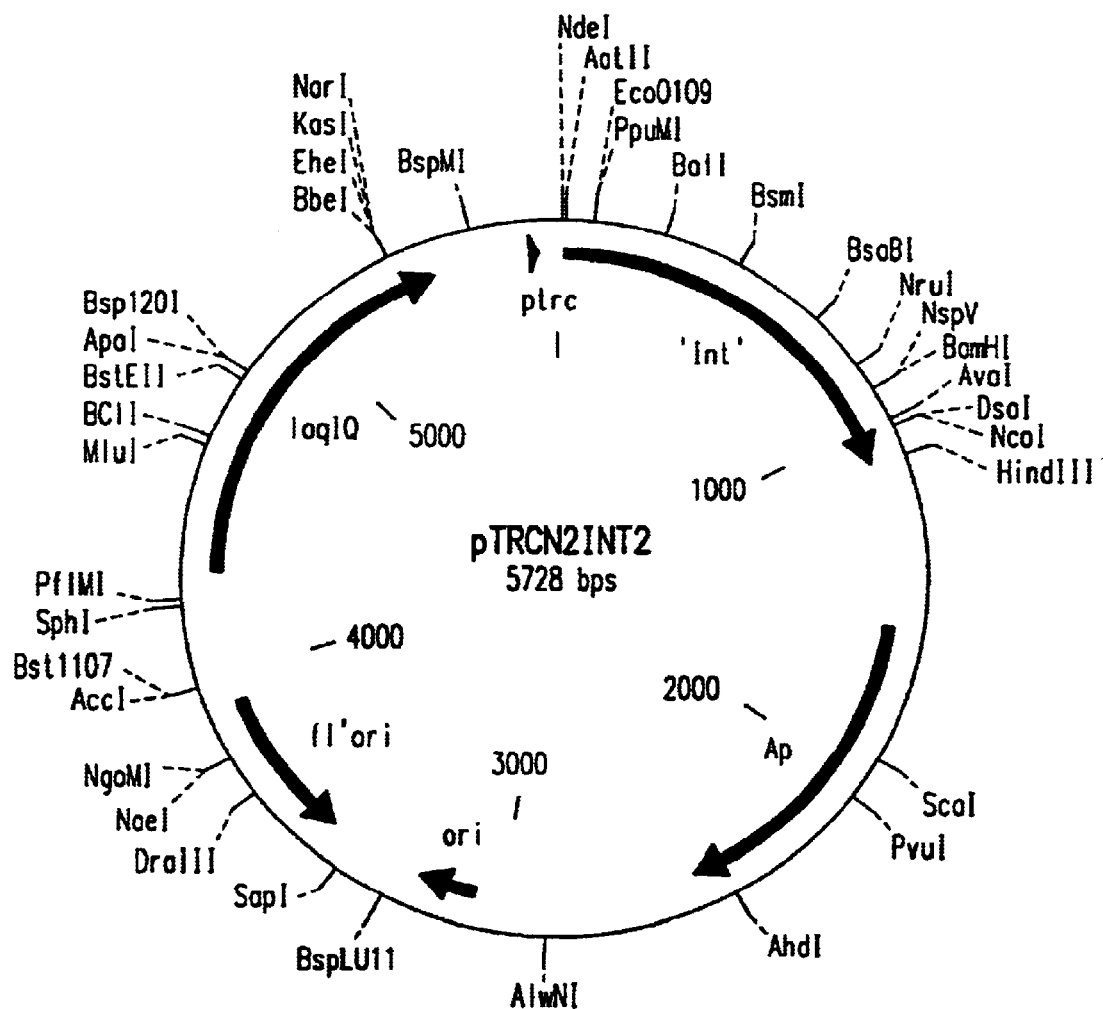
FIG. 11 depicts a restriction map for plasmid pTRCN2INT2. Ap: β-lactamase gene; ptrc: trc promoter; laqI$^Q$: lac repressor gene; fl'ori: fl intergenic region; ori: colE1 origin of replication; Int: λ integrase gene.

The following two oligonucleotides were used to clone the Int gene: TAT TAT TAT CAT ATG GGA CGA CGT CGA AGT CAT GAG CGC CGG GAT (SEQ ID NO:1) and A TTA TTA AGC TTA TTA ATG GTG ATG ATG GTG ATG TTT GAT TTC AAT TTT GTC CCA CTC (SEQ ID NO:2). The oligonucleotides were used to generate a 1,092-bp PCR amplification product using λ DNA as the template. DNA was amplified (Materials and Methods section PCR) during 8 cycles composed of the following steps: 95° C. for 15 seconds, 55° C. for 15 seconds, and 72° C. for 90 seconds. The 1,092-bp PCR product was digested with NdeI and HindIII and cloned into the NdeI and HindIII sites of plasmid pTRCN2 (FIG. 10) in an *E. coli* DH10B host. This construct is called pTRCN2INT2 (FIG. 11). The Int gene is under control of a pTRC promoter and contains a sequence coding for a His$_6$ tag at the carboxy end of the protein. The DNA sequence of the Int gene in pTRCN2INT2 was determined and found to match the published sequence, except as modified below. Arg codons AGA and AGG originally coding for Arg at positions 3 and 4 were changed to CGA and CGT, respectively, which are Arg codons more frequently used in *E. coli*.

Purification of Int-His$_6$

Int-His$_6$ was purified from *E coli* DH10B cells bearing plasmid pTRCN2INT2 (see Materials and Methods section Cloning of Int-His$_6$).

Growth of Cells

To prepare seed stocks, *E. coli* DH10B cells bearing plasmid pTRCN2INT2 were grown at 30° C. in Buffered Rich medium+100 μg/ml ampicillin to an $A_{590}$ ~2. Culture was mixed 1:1 with 50% glycerol. The mixture was aliquoted by 1 ml into cryovials on ice and then stored at −80° C.

For a small scale growth, cells from a frozen glycerol stock were inoculated into 2×50 ml Buffered Rich medium+ 100 μg/ml ampicillin in 2×250-ml bottom-baffled shake flasks. Cells were grown for 16.5 hours at 30° C. and 250 rpm to an $A_{590}$ of ~4.0. Twenty-five ml of the primary shake flask growth was used to inoculate each of 4, 2.8-L bottom-baffled Fernbach flasks containing 1 L of Buffered Rich medium+100 μg/ml ampicillin (for an initial $A_{590}$ of ~0.1). Cultures were grown at 30° C. until an $A_{590}$=1.0 to 1.5 was achieved. The cultures were induced by adding IPTG to 1 mM. Growth was continued for 2 hr at 30° C. The culture was chilled by icing in 4×1 L centrifuge bottles and harvested by centrifugation at 4,500 rpm (5,895×g) and 4° C. for 12 minutes. Each pellet was washed by resuspension in ~7 ml 50 mM Tris-HCl (pH 8.0), 100 mM NaCl at 4° C. and re-spun. The pellets were frozen and stored at −80° C.

For a large scale growth, 50 ml of Buffered Rich medium+ 100 μg/ml ampicillin in a 250 ml bottom baffled shake flask was inoculated with 1 ml of a frozen seed. Cells were grown at 30° C. and 250 rpm to an $A_{590}$ of 0.8 to 1.2. The entire 50 ml was inoculated into 500 ml Buffered Rich medium+100 μg/ml in a 2.8-L bottom-baffled Fernbach. Growth was continued at 30° C. and 250 rpm to an $A_{590}$=0.8 to 1.2.

10 L of Buffered Rich medium+100 μg/ml ampicillin in a 14-L vessel was inoculated with all 500 ml of culture. Temperature was maintained at 30° C. Dissolved oxygen levels were controlled at >30% and pH at 7+/−0.3. At $A_{590}$=1.5 to 2.0 the culture was induced by adding IPTG to 1 mM. Growth was continued for 2 hr at 30° C. The vessel was chilled and harvested by centrifugation in a Sharples centrifuge. Cell paste was frozen and stored at −80 C.

Purification

Frozen cells (20 g) were thawed on ice and suspended in 40 ml of Tris-HCl (pH 8.0)-10% (w/v) sucrose. Cells were disrupted on ice by sonication (4, 30 second bursts at 70% maximum setting), and the extract was centrifuged at 27,000×g for 30 minutes at 4° C. The supernatant was collected. The supernatant was mixed with 20 ml (packed volume) of Chelating Sepharose (Pharmacia) charged with NiSO$_4$ and equilibrated with Buffer A (50 mM Tris-HCl (pH 8.0), 0.3 M NaCl, 10% (v/v) glycerol). The slurry was transferred to 50-ml conical tubes and was gently rocked for 30 minutes at 4° C. The slurry was then packed into a 1.6 cm column and attached to an FPLC system (Pharmacia). The column was washed with 20 column volumes of Buffer A+20 mM Imidazol at 30 cm/hr. The protein was eluted with a 15-column volume linear gradient from Buffer A+20 mM Imidazol to Buffer A+500 mM Imidazol. Fractions were analyzed by SDS PAGE. Fractions containing Int-His$_6$ were pooled and 0.5 M EDTA was added to a final concentration of 1 mM. The pool was then transferred to 10,000 molecular weight cut off (MWCO) dialysis tubing and dialyzed against 50 volumes of Buffer B (50 mM Tris-HCl (pH 7.5), 1 mM EDTA, 10% (v/v) glycerol, and 1 mM β-mercaptoethanol). The dialyzed pool was loaded at 38 cm/hr onto a 2 ml (1×1 cm) EMD-SO$_4$ (EM Separations) column equilibrated in Buffer B+0.2 M NaCl. The column was washed with 10 column volumes of Buffer B+0.2 M NaCl at 76 cm/hr and developed with a 15-column volume linear gradient from Buffer B+0.2 M NaCl to Buffer B+1.6 M NaCl. Int-His$_6$ eluted at approximately 1.1 M NaCl based upon analysis by SDS PAGE. The peak fractions were pooled and the pool was transferred to 10,000 MWCO dialysis tubing and dialyzed against 100 volumes of Buffer C (Buffer B minus EDTA). The dialyzed pool was loaded at 38 cm/hr onto a 1 ml (0.5×1 cm) hydroxyapatite column (Type II, BioRad) equilibrated in Buffer C. The column was washed with 10 column volumes of Buffer C+1 M NaCl and developed with 10 column volumes of Buffer C+0.6 M NaCl+25 mM KPO$_4$ at 19 cm/hr. The fractions were analyzed by SDS PAGE and the peak fractions containing Int-His$_6$ were pooled. The pool was transferred to 10,000 MWCO dialysis tubing and was dialyzed against 200 volumes of 50 mM Tris-HCl (pH 7.5), 50 mM NaCl, 0.05 mM EDTA, 50% (v/v) glycerol, and 1 mM DTT overnight at 4° C. The final sample was stored at −70° C.

Cloning of Xis-His$_6$

Figure 12:
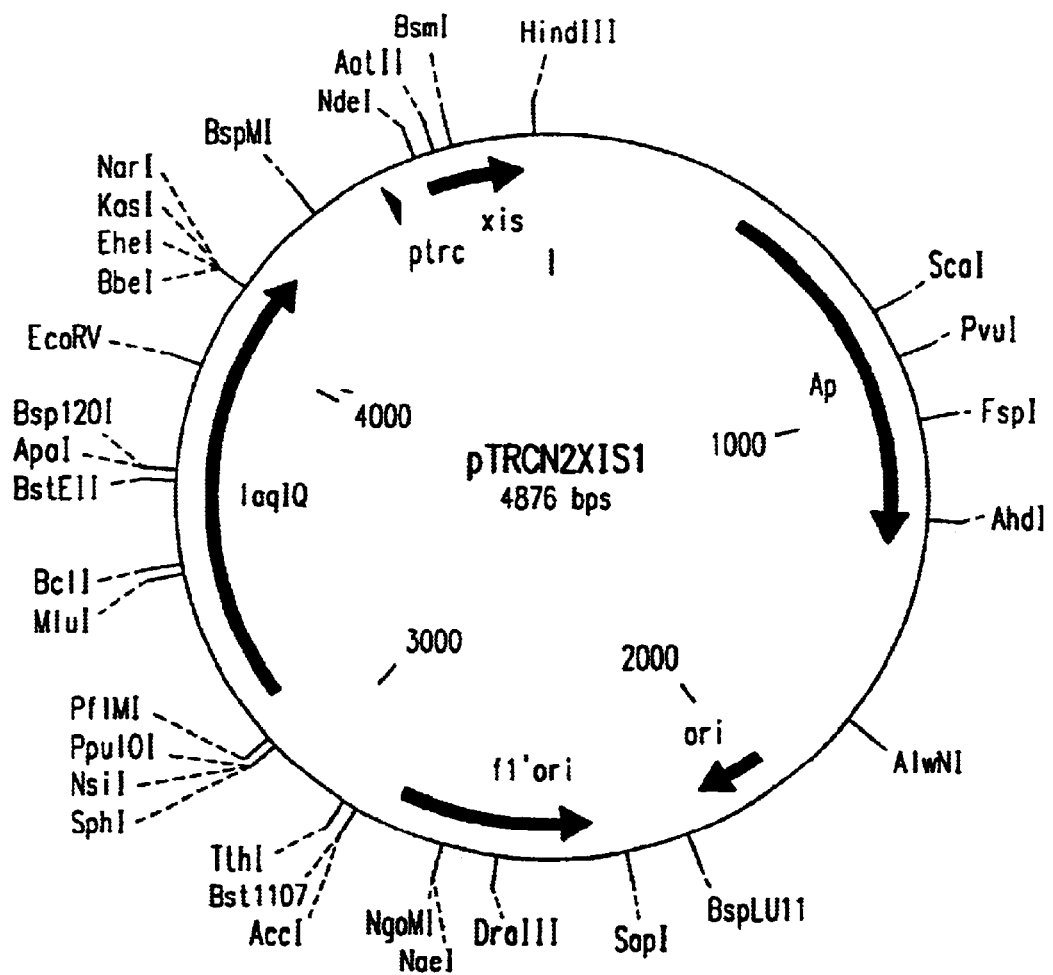
FIG. 12 depicts a restriction map for plasmid pTRCN2XIS1. Ap: β-lactamase gene; ptrc: trc promoter; laqI$^Q$: lac repressor gene; fl'ori: fl intergenic region; ori: colE1 origin of replication; xis: λ xis gene.

The following two oligonucleotides were used to clone the Xis gene: TAT TAT TAT CAT ATG TAC TTG ACA CTT CAG GAG (SEQ ID NO:3) and ATT ATT AAG CTT ATT AAT GGT GAT GAT GGT GAT GTG ACT TCG CCT TCT TCC CAT T (SEQ ID NO:4). The oligonucleotides were used to generate a 219-bp PCR product using λ DNA as the template. DNA was amplified (Materials and Methods section PCR) during 15 cycles composed of the following steps: 95° C. for 15 seconds, 55° C. for 15 seconds, and 72° C. for 60 seconds. The 219-bp PCR product was digested with NdeI and HindIII and cloned into the NdeI and HindIII site of pTRCN2 (FIG. 10). The resulting construct was called pTRCN2XIS1 (FIG. 12). The Xis gene is under control of a pTRC promoter and contains a sequence coding for a His$_6$ tag at the carboxy end of the protein. The DNA sequence of the Xis gene in pTRCN2XIS1 was determined and found to match the published sequence.

Purification of Xis-His$_6$

Xis-His$_6$ was purified from *E. coli* Stbl 2 cells bearing plasmid pTRCN2XIS1 (see Materials and Methods section Cloning of Xis-His$_6$).

Growth of Cells

To prepare seed stocks, *E. coli* Stbl 2 cells bearing plasmid pTRCN2XIS1 were grown at 37° C. in Buffered Rich medium+100 μg/ml ampicillin to an A$_{590}$ ~3. Culture was mixed 1:1 with 50% glycerol. The mixture was aliquoted by 1 ml into cryovials on ice and then stored at −70° C.

For small scale growths, cells from a frozen glycerol stock were inoculated into 50 ml Buffered Rich medium+100 μg/ml ampicillin in a 250-ml bottom-baffled shake flask. Cells were grown for 17 hours at 37° C. and 250 rpm to an A$_{590}$ of ~4.0.

12 ml of the primary shake flask growth was used to inoculate each of 4, 2.8-L bottom-baffled Fernbach flasks containing 1 L of Buffered Rich medium+100 μg/ml ampicillin (for an initial A$_{590}$ of ~0.05). Cultures were grown at 37° C. until an A$_{590}$=1.5 to 2.0 was achieved. The cultures were induced by adding IPTG to 1 mM. Growth was continued for 2 hr at 37° C. The culture was chilled by icing in 4×1 L centrifuge bottles and harvested by centrifugation at 4,500 rpm (5,895×g) and 4° C. for 15 minutes. Each pellet was washed by resuspension in ~20 ml used medium and re-spun. The pellets were frozen and stored at −70° C.

For a large scale growth, a 50 ml culture of Buffered Rich medium+100 μg/ml ampicillin in a 250-ml bottom baffled shake flask was inoculated with 1 ml of a frozen seed. Cells were grown at 37° C. and 250 rpm to an A$_{590}$ of 0.6 to 1.4. The entire 50 ml was inoculated into 500 ml Buffered Rich medium+100 μg/ml ampicillin in a 2.8-L bottom-baffled Fernbach. Growth was continued at 37° C. and 250 rpm to an A$_{590}$=0.6 to 1.4. Ten L of Buffered Rich medium+100 μg/ml ampicillin in a 14-L vessel was inoculated with all 500 ml of culture. Temperature was maintained at 37° C. Dissolved oxygen levels were controlled at >30% and pH at 7+/−0.3. At A$_{590}$=1.5 to 2.0 the culture was induced by adding IPTG to 1 mM. Growth was continued for 2 hr at 37° C. The vessel was chilled and harvested by centrifugation in a Sharples centrifuge. Cell paste was frozen and stored at −70° C.

Purification

Frozen cells (20 g) were thawed on ice and suspended in 20 ml of 50 mM Tris-HCl (pH 8.0), 10% (w/v) sucrose, 0.002 mg/ml leupeptin, 0.002 mg/ml pepstatin A, 0.8 mg/ml benzamide, and 0.05 mg/ml Pefablock. Cells were disrupted by sonication (5 second bursts at 80% of the maximum setting alternated with 5 seconds off for 3 minutes). The extract was centrifuged at 27,000×g for 30 minutes at 4° C. and the supernatant was collected. The supernatant was loaded at 30 cm/hr onto a 20-ml column (1.6×10 cm) of Chelating Sepharose (Pharmacia) charged with NiSO$_4$ and equilibrated with Buffer D (50 mM Tris-HCl (pH 7.5), 0.4 M NaCl, and 10 % (v/v) glycerol)+5 mM Imidazol. The column was washed with 20 column volumes of Buffer D+5 mM Imidazol at 30 cm/hr and developed with a 15-column volume linear gradient from Buffer D+5 mM Imidazol to Buffer D+450 mM Imidazol at 12 cm/hr. Fractions were analyzed by SDS PAGE. Peak fractions containing the Xis-His$_6$ protein were pooled and 0.5 M EDTA and 1 M DTT were added to final concentrations of 1 mM and 4 mM, respectively. The pool was then loaded at 38 cm/hr onto a 5.5 ml (1.0×7.0 cm) EMD-SO$_4$ (EM Separations) column equilibrated in Buffer E (50 mM Tris-HCl (pH 7.5), 1 mM EDTA, 10% (v/v) glycerol, and 4 mM DTT)+0.4 M NaCl. The column was washed with 10 column volumes of Buffer E+0.4 M NaCl at 76 cm/hr and developed with a 10-column volume linear gradient from Buffer E+0.4 M NaCl to Buffer E+2 M NaCl at 15 cm/hr. Fractions were analyzed by SDS PAGE. Xis-His$_6$ elutes in a broad peak at approximately 1.1–1.8 M NaCl. The peak fractions containing Xis-His$_6$ were pooled. The pool was diluted with Buffer E to match the ionic strength of Buffer E+0.2 M NaCl and loaded at 152 cm/hr onto a 1 ml (0.5×5.0 cm) Mono S (Pharmacia) column equilibrated in Buffer E+0.2 M NaCl. The column was washed with 10 column volumes of Buffer E+0.2 M NaCl. Xis-His$_6$ was eluted with 10 column volumes of Buffer E+2.0 M NaCl at 61 cm/hr. Fractions were analyzed by SDS PAGE and the peak fractions containing Xis-His$_6$ were pooled. The pool was transferred to a 2,000 molecular weight cut off dialysis cassette (Pierce) and was dialyzed against 200 volumes of 50 mM Tris-HCl (pH 7.5), 50 mM NaCl, 0.05 mM EDTA, 50% (v/v) glycerol, and 1 mM DTT overnight at 4° C. The final sample was stored at −70° C.

Cloning of S20

Figure 13:
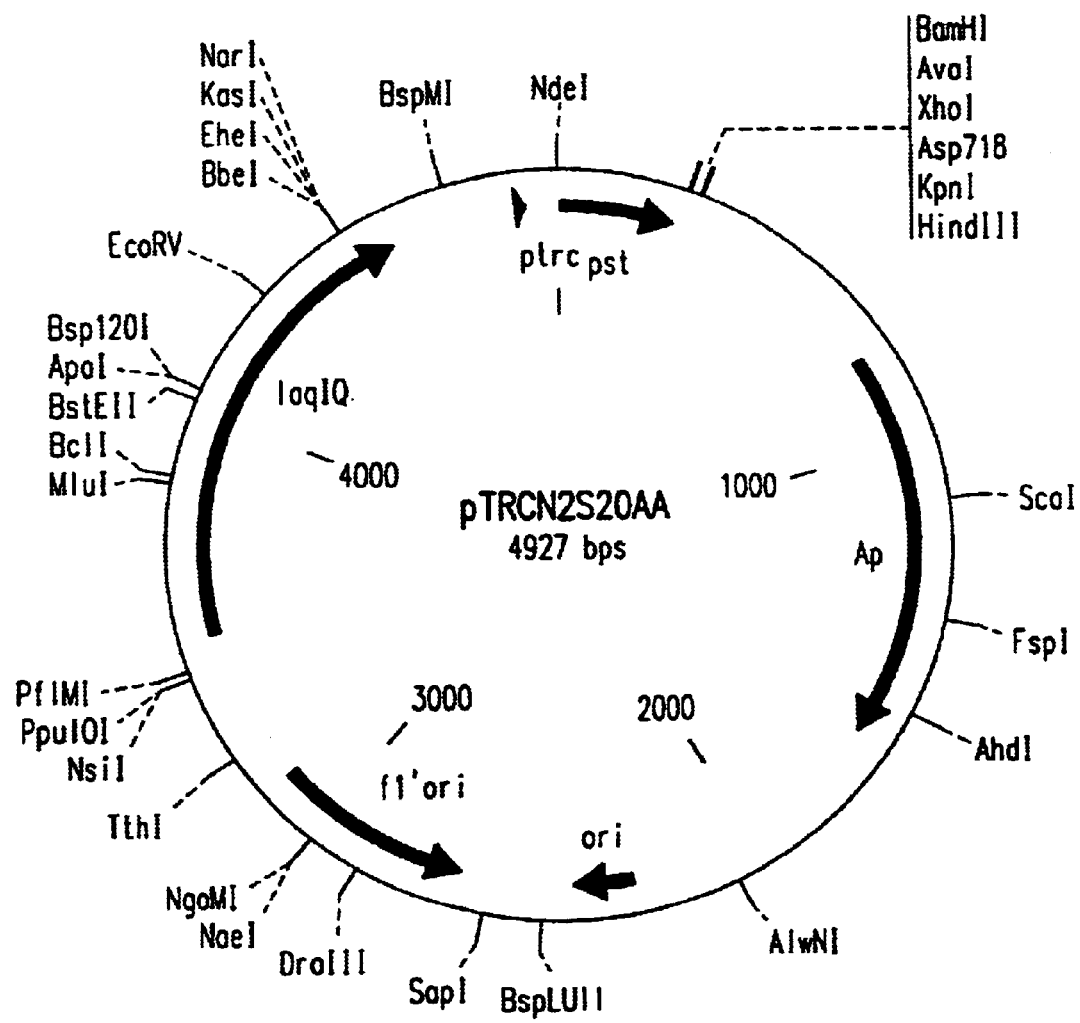
FIG. 13 depicts a restriction map for plasmid pTRCN2S20AA. Ap: β-lactamase gene; ptrc: trc promoter; laqI$^Q$: lac repressor gene; fl'ori: fl intergenic region; ori: colE1 origin of replication; rpsT: S20 gene.
Figure 14:
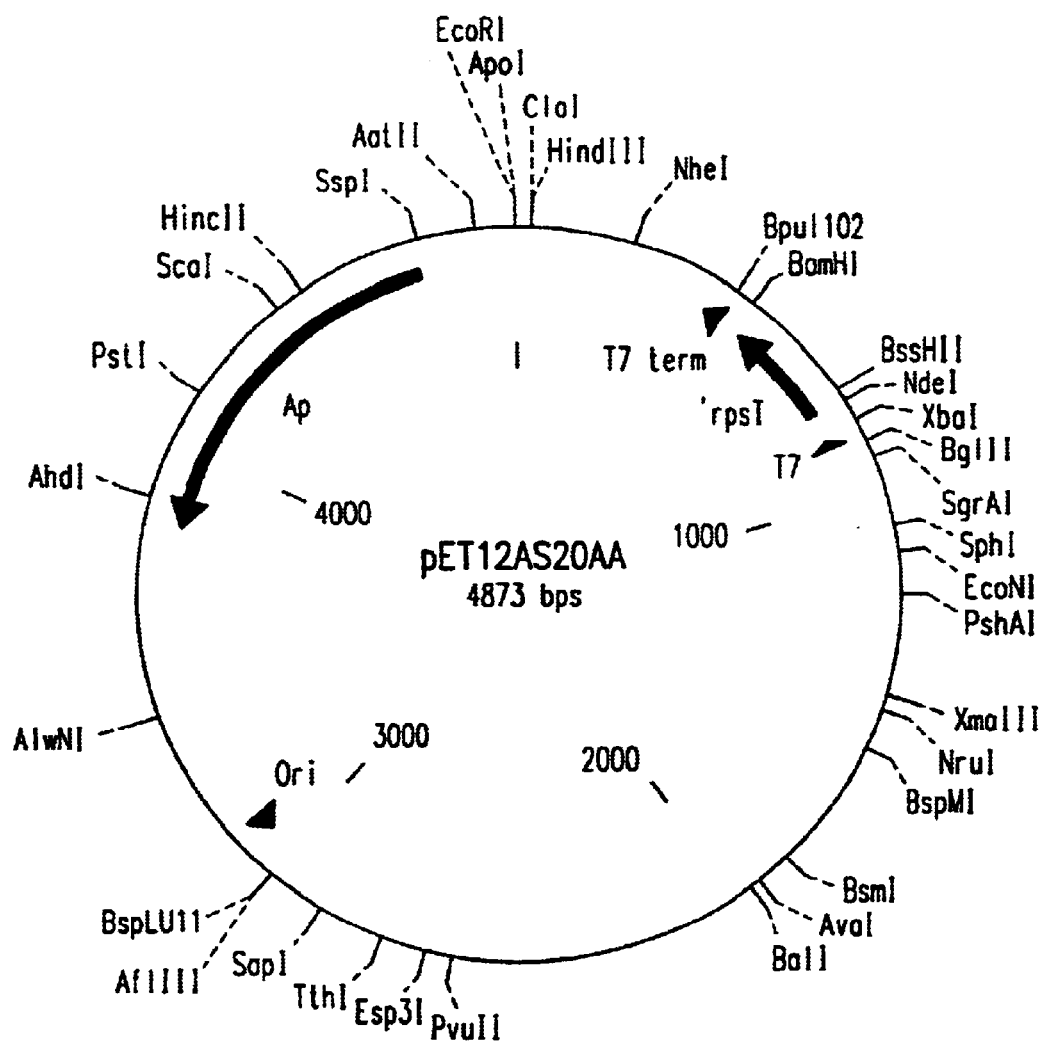
FIG. 14 depicts a restriction map for plasmid pET12AS20AA. Ap: β-lactamase gene; ori: colE1 origin of replication; 'rpsT: S20 gene; T7: T7 promoter; T7 term: T7 transcription termination sequence.

The following two oligonucleotides were used to clone the S20 gene: TAT TAT TAT CAT ATG GCT AAT ATC AAA TCA GCT AAG (SEQ ID NO:5) and ATT ATT GGA TCC ATT AAG CCA GTT TGT TGA TCT (SEQ ID NO:6). The oligonucleotides were used to generate a 267-bp PCR product using *E. coli* chromosomal DNA as template. DNA was amplified (Materials and Methods section PCR) during 15 cycles composed of the following steps: 95° C. for 15 seconds, 50° C. for 15 seconds, and 67° C. for 30 seconds. The 267-bp PCR product was digested with NdeI and BamHI and cloned into the NdeI and BamHI sites of pTRCN2 (FIG. 10) in *E. coli* DH10B. The resulting construct was called pTRCN2S20AA (FIG. 13). The S20 gene is under control of a pTRC promoter. The DNA sequence of the S20 gene in pTRCN2S20AA was determined and found to match the published sequence, except as noted below. The initiation codon was changed from TTG to ATG during cloning to enhance expression. pTRCN2S20AA was digested with NdeI and BamHI to generate a 267-bp fragment that was cloned into the NdeI and BamHI sites of pET12A (Novagen) in *E. coli* strain BL21 DE3. The resulting construct was called pET12AS20AA (FIG. 14). The S20 gene is under control of a T7 promoter.

Purification of Recombinant S20

S20 was purified from *E. coli* BL21DE3 bearing plasmid pET12AS20AA (see Materials and Methods section Cloning of S20).

Growth of Cells

Cells from a glycerol stock of BL21DE3 bearing plasmid pET12AS20AA were inoculated into 3 ml of LB broth containing 100 mg/ml ampicillin. This inoculum was diluted into LB broth+100 mg/ml ampicillin 1:100 and the 300-ml culture was grown overnight at 30° C. The $A_{650}$ of the culture should not exceed 1.0. This culture was used to innoculate 10 flasks containing 500 ml each of CIRCLE-GROW® brand culture medium (BIO 101) plus 100 mg/ml ampicillin plus 1 mM $MgSO_4$. Cells were grown at 37° C. until the $A_{650}$ was 0.5 and expression of S20 was induced by the addition of IPTG to 0.5 mM. After growth at 37° C. for 4 hours, cells were harvested by centrifugation at 4° C. and stored at −70° C.

Purification

Frozen cells (10 g) were thawed on ice and suspended in 25 ml of 50 mM Tris-HCl (pH 7.5), 0.2 mM EDTA, 10% (v/v) glycerol, 0.2 mM DTT, 0.2 μg/ml leupeptin, and 1 mM PMSF. Cells were then disrupted by sonication (5 second bursts at 80% of the maximum setting alternated with 5 seconds off for 1.5 minutes). NaCl (5.0 M) was then added to a final concentration of 0.67 M. The slurry was mixed by inverting the container and then placed on ice for 10 minutes. The mixture was centrifuged at 27,000×g for 30 minutes at 4° C. and the supernatant was collected. The supernatant was diluted with Buffer B (50 mM Tris-HCl (pH 7.5), 1 mM EDTA, 10% (v/v) glycerol, 1 mM β-mercaptoethanol) to match the ionic strength of Buffer B+0.3 M NaCl and then loaded at 30 cm/hr onto a 7.5 ml (1.8×3.7 cm) $EMD-SO_4$ (EM Separations) column equilibrated in Buffer B+0.3 M NaCl. The column was washed with 10 column volumes of Buffer B+0.3 M NaCl at 30 cm/hr and developed with a 15-column volume linear gradient from Buffer E+0.3 M NaCl to Buffer E+1.8 M NaCl at 30 cm/hr. Fractions were analyzed by SDS PAGE. S20 eluted at approximately 0.9 M NaCl. The fractions containing the peak of S20 were pooled. The pool was transferred to a 2,000 molecular weight cut off dialysis cassette (Pierce) and dialyzed against 200 volumes of 50 MM Tris-HCl (pH 7.5), 50 mM NaCl, 0.05 mM EDTA, 50% (v/v) glycerol, and 1 mM DTT overnight at 4° C. The final sample was stored at −70° C.

Integrative Recombination Gel Assay

Reaction mixtures (10 μl final volume) for monitoring integrative recombination (defined as containing linearized attB and supercoiled attP DNA substrates) by agarose gel electrophoresis were incubated at 25° C. for 45 minutes. Reactions were initiated by adding 1 μl of Int or Int-$His_6$ (contained in 50 mM Tris-HCl (pH 7.5), 1 mM EDTA, 600 mM KCl, 2 mg/ml BSA, and 10% (v/v) glycerol) plus or minus potential stimulatory proteins to a mixture containing 20 mM Tris-HCl (pH 8.0), 5 mM spermidine, 50 μg/ml BSA, 125 ng linearized pBB105, 125 ng supercoiled pHN894, and 12.5 ng IHF. Incubation was stopped by raising the temperature to 70° C. for 10 minutes and then adding 2.5 μl of 25% (w/v) Ficoll 400, 0.5% (w/v) SDS, and 0.00625% (w/v) bromophenol blue. In some cases, reaction mixtures were treated with proteinase K (10 to 20 μg at 25° C. for 15 minutes). Samples were analyzed by electrophoresis in a 1% agarose minigel cast in 40 mM Tris-acetate (pH 8.3)-1 mM EDTA (TAE) and 1 μg/ml ethidium bromide and run in TAE at 105 V for 30 minutes. Recombination activity is indicated by the appearance of a DNA band migrating at 10,201 bp. A unit of Int activity was defined as described (Nash, H. A. *Methods Enz.* 100: 210–216 (1983)).

Excisive Recombination Gel Assay

Reaction mixtures (10 μl final volume) for monitoring excisive recombination (defined as containing linearized attL and supercoiled attR DNA substrates) by agarose gel electrophoresis were incubated at 25° C. for 45 minutes. Reactions were initiated by adding 1 μl of Int or Int-$His_6$ (contained in 50 mM Tris-HCl (pH 7.5), 1 mM EDTA, 600 mM KCl, 2 mg/ml BSA, and 10% (v/v) glycerol) plus or minus potential stimulatory proteins to a mixture containing 20 mM Tris-HCl (pH 8.0), 5 mM spermidine, 50 μg/ml BSA, 125 ng linearized pHN872, 125 ng supercoiled pHN868, 12.5 ng IHF, and 28 ng Xis or Xis-$His_6$. Incubation was stopped by raising the temperature to 70° C. for 10 minutes and then adding 2.5 μl of 25% (w/v) Ficoll 400, 0.5% (w/v) SDS, and 0.00625% (w/v) bromophenol blue. In some cases, reaction mixtures were treated with proteinase K (10 to 20 μg at 25° C. for 15 minutes). Samples were analyzed by electrophoresis in a 1% agarose minigel cast in 40 mM Tris-acetate (pH 8.3)-1 mM EDTA (TAE) and 1 μg/ml ethidium bromide and run in TAE at 105 V for 30 minutes. Recombination activity is indicated by the appearance of a DNA band migrating at 9,991 bp.

Integrative Recombination Colony-Forming Assay

Reaction mixtures (20 μl final volume) for monitoring integrative recombination (defined as containing linearized attB and supercoiled attP DNA substrates) by transformation of *E. coli* were incubated at 25° C. for 45 minutes. Reactions were initiated by adding 4 μl of Int or Int-$His_6$ (contained in 50 mM Tris-HCl (pH 7.5), 50 mM NaCl, 1 mM EDTA, 200 μg/ml BSA, and 50% (v/v) glycerol) plus or minus S20 to a mixture containing 50 mM Tris-HCl (pH 7.5), 50 mM NaCl, 2.5 mM spermidine, 0.25 mM EDTA, 200 μg/ml BSA, 100 ng linearized pEZC7501, 100 ng supercoiled pEZ13835, and 10 ng IHF. Incubation was stopped by raising the temperature to 70° C. for 10 minutes. Proteinase K (4 μg in 1 μl) was added and after 10 minutes at 37° C. the mixture was centrifuged (14,000 rpm for 30 seconds). The mixture (1 μl) was used to transform 100 μl of ME DH5α *E. coli* competent cells (LTI) in a sterile polypropylene tube on ice. After 30 minutes on ice, the tube was heat shocked in a 42° C. water bath for 45 seconds. The tube was then placed on ice for 2 minutes. S.O.C. medium (0.9 ml) was added to the tube, and the tube was placed in a shaker for 60 minutes at 37° C. and 225 rpm. Aliquots (10 and 100 μl) of the transformed cells were spread on separate agar plates prepared in LB medium+100 µg/ml kanamycin, and the plates were incubated at 37° C. for 16 to 24 hours. Kanamycin-resistant colonies arise only as the result of an integrative recombination event.

Excisive Recombination Colony-Forming Assay

Reaction mixtures (20 µl final volume) for monitoring excisive recombination (defined as containing linearized attR and supercoiled attL DNA substrates) by transformation of *E. coli* were incubated at 25° C. for 45 minutes. Reactions were initiated by adding 4 µl of Int or Int-His$_6$ (contained in 50 mM Tris-HCl (pH 7.5), 50 mM NaCl, 1 mM EDTA, 200 µg/ml BSA, and 50% (v/v) glycerol) plus or minus S20 to a mixture containing 50 mM Tris-HCl (pH 7.5), 50 mM NaCl, 2.5 mM spermidine, 0.25 mM EDTA, 200 µg/ml BSA, 100 ng linearized pEZC8402, 100 ng supercoiled pEZ11104, 12.5 ng IHF, and 28 ng Xis or Xis-His$_6$. Incubation was stopped by raising the temperature to 70° C. for 10 minutes. Proteinase K (4 µg in 1 µl) was added and after 10 minutes at 37° C. the mixture was centrifuged (14,000 rpm for 30 seconds). A portion of the reaction mixture (10.5 µl) was diluted with 89.5 µl of T$_{10}$E$_1$. The diluted mixture (1 µl) was used to transform 100 µl of ME DH5α *E. coli* competent cells (LTI) in a sterile polypropylene tube on ice. After 30 minutes on ice, the tube was heat shocked in a 42° C. water bath for 45 seconds. The tube was then placed on ice for 2 minutes. S.O.C. medium (0.9 ml) was added to the tube, and the tube was placed in a shaker for 60 minutes at 37° C. and 225 rpm. Aliquots (10 and 100 µl) of the transformed cells were spread on separate agar plates prepared in LB medium+100 µg/ml ampicillin, and the plates were incubated at 37° C. for 16 to 24 hours. Ampicillin-resistant colonies arise only as the result of an excisive recombination event.

RESULTS

Part I
Restoration of Integrase Activity by Mixing with Cell Extract Components

Restoration of Int Activity by Column Fractions

Purification of Int overexpressed in *E. coli* involved differential salt precipitation followed by phosphocellulose and hydroxyapatite chromatography (Materials and Methods). When we attempted to purify native Int by this procedure, we found that Int integrative recombination activity (determined as described in Materials and Methods section, Integrative Recombination Gel Assay) was maintained through the phosphocellulose chromatography step, but was lost during the final hydroxyapatite chromatography step. No activity was found in any hydroxyapatite column fraction. This was not caused by loss of Int protein during chromatography, since SDS-PAGE analysis of the hydroxyapatite fractions revealed the presence of a single protein of molecular weight 40 KDa, consistent with the bound protein being Int. Fractions containing the peak of the 40-KDa protein were pooled and the pool was assayed for integrative recombination activity. As the results shown in Table 2 indicate, no activity was observed.

TABLE 2

SUMMARY OF PURIFICATION OF NATIVE Int

| Purification Step | Total Units | Total Protein (mg) | Specific Activity (U/mg) |
|---|---|---|---|
| Crude Extract | 228,000 | 1,294 | 176 |
| Differential salt precipitation | 67,000 | 153 | 441 |
| Phosphocellulose | 21,000 | 6.7 | 3,134 |

TABLE 2-continued

SUMMARY OF PURIFICATION OF NATIVE Int

| Purification Step | Total Units | Total Protein (mg) | Specific Activity (U/mg) |
|---|---|---|---|
| Hydroxyapatite | 0 | 0.2 | — |
| Hydroxyapatite + stimulatory protein(s) | ~30,000 | 0.2 | ~150,000 |

Figure 15:
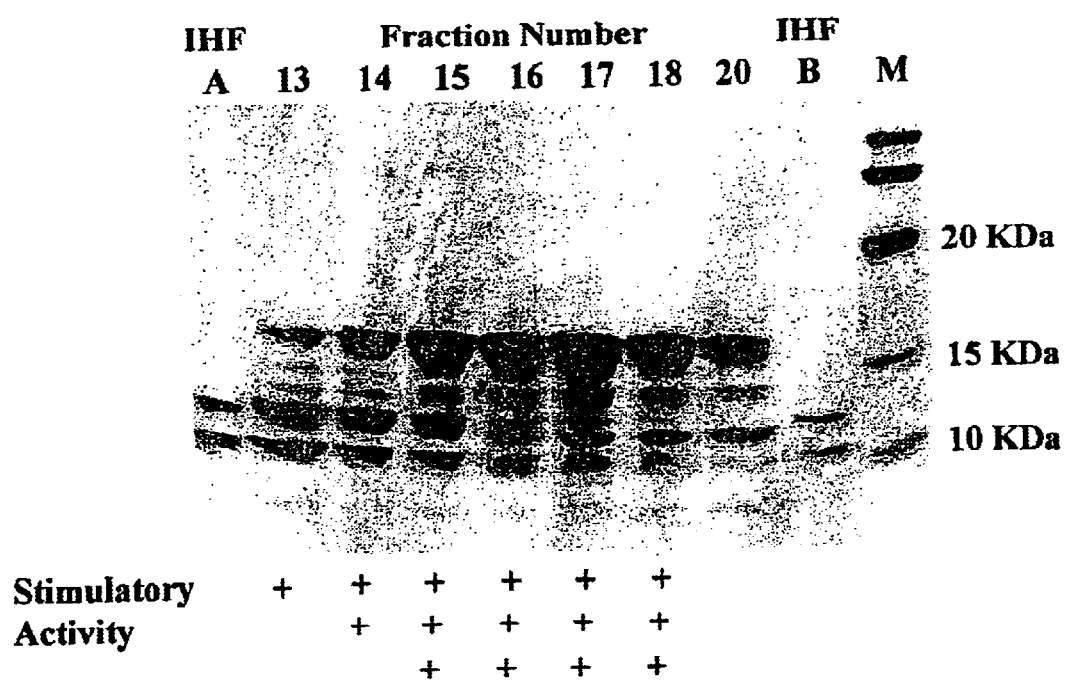
FIG. 15 is a photograph of an SDS-PAGE gel of fractions from phosphocellulose column fractionation of proteins not bound by hydroxyapatite. Aliquots (7.5 μl) from fractions 13 through 20 of the phosphocellulose column of proteins not bound by hydroxyapatite were analyzed by SDS PAGE. IHF ("IHF A": 0.3 μg; "IHF B": 0.5 μg) and BenchMark protein standards ("M") were run as references. The bottom of the figure indicates the relative ability of aliquots from the fractions to stimulate Int in an integrative recombination gel assay (−, no stimulation; +, ++, +++, increasing levels of stimulation).

Examination of the proteins in the phosphocellulose pool by SDS PAGE revealed the presence of Int (40 KDa) and a number of smaller proteins (at least six) in the 5 to 17 KDa range. *E. coli* DNA binding proteins that stimulate Int activity, such as HU, fall in this small size range (Segall, A. M. et. al, *EMBO J.* 13: 4536–4548 (1994)). We therefore hypothesized that this preparation of Int required additional component(s) for activity beyond the IHF already present in recombination reaction mixtures (Materials and Methods). Further, the chromatography results suggested that this component(s) coeluted with Int from phosphocellulose, but was not bound by hydroxyapatite. To test this hypothesis, the material from the original phosphocellulose pool that did not bind to hydroxyapatite was fractionated again on a phosphocellulose column. Samples from fractions from this column were assayed for ability to restore integrative recombination activity to the inactive Int pooled from the hydroxyapatite column. We found that fractions eluting from the phosphocellulose column at around 1.0 M KCl contained a component(s) that restored recombination activity to the inactive Int (FIG. 15). The fractions with the greatest stimulatory activity (Fraction Numbers 15 through 18 in FIG. 15) were used for further characterization. Unit assay of the Int hydroxyapatite pool in the integrative recombination assay in the presence of an optimal amount of this stimulatory material indicated that greater than 100% of the Int activity present in the phosphocellulose pool was present in the hydroxyapatite pool when the stimulatory component(s) was present in the unit assay (Table 2).

Characterization of the Stimulatory Component(s)

SDS PAGE analysis of the stimulatory fractions from the second phosphocellulose column showed multiple small protein bands, two of which appeared similar in size to the subunits of authentic IHF (FIG. 15). On the chance that the concentration of IHF being used in the integrative recombination gel assay was not optimal, a careful titration of IHF was carried out with inactive Int in the presence and absence of stimulatory material from the phosphocellulose column. We found that no amount of IHF alone, from 12.5 to 1,250 ng, stimulated inactive Int. In contrast, the combination of IHF at 12.5 ng and the component(s) from the phosphocellulose column did restore Int activity.

Treatment of the stimulatory component(s) with DNase I or RNase A did not diminish ability to stimulate Int. Placing the component(s) in a boiling water bath for 30 minutes also had no effect. However, treatment with proteinase K eliminated ability to stimulate, indicating the stimulatory component(s) was protein that could withstand high temperature.

Part II
Purification and Identification of the Stimulatory Proteins

Purification from a Side Fraction

We wished to identify the protein(s) in extracts of *E. coli* expressing native Int that stimulate its recombinase activity.

Purification was monitored by detecting the presence of Int stimulatory protein using the integrative recombination gel assay (Materials and Methods) and inactive Int, purified as just described (Materials and Methods section Purification of Native Int and Results section PART I: Restoration of Integrase Activity by Mixing with Cell Extract Components). We took advantage of the fact that extracts could be heated to boiling water temperatures without affecting adversely the stimulatory activity. Heating served several purposes. First, any active Int present during early purification steps would be irreversibly inactivated, eliminating interference in the gel recombination assay. Second, many E. coli proteins in crude extracts precipitate at high temperature; thus heating facilitates purification of those proteins that remain soluble.

Figure 16:
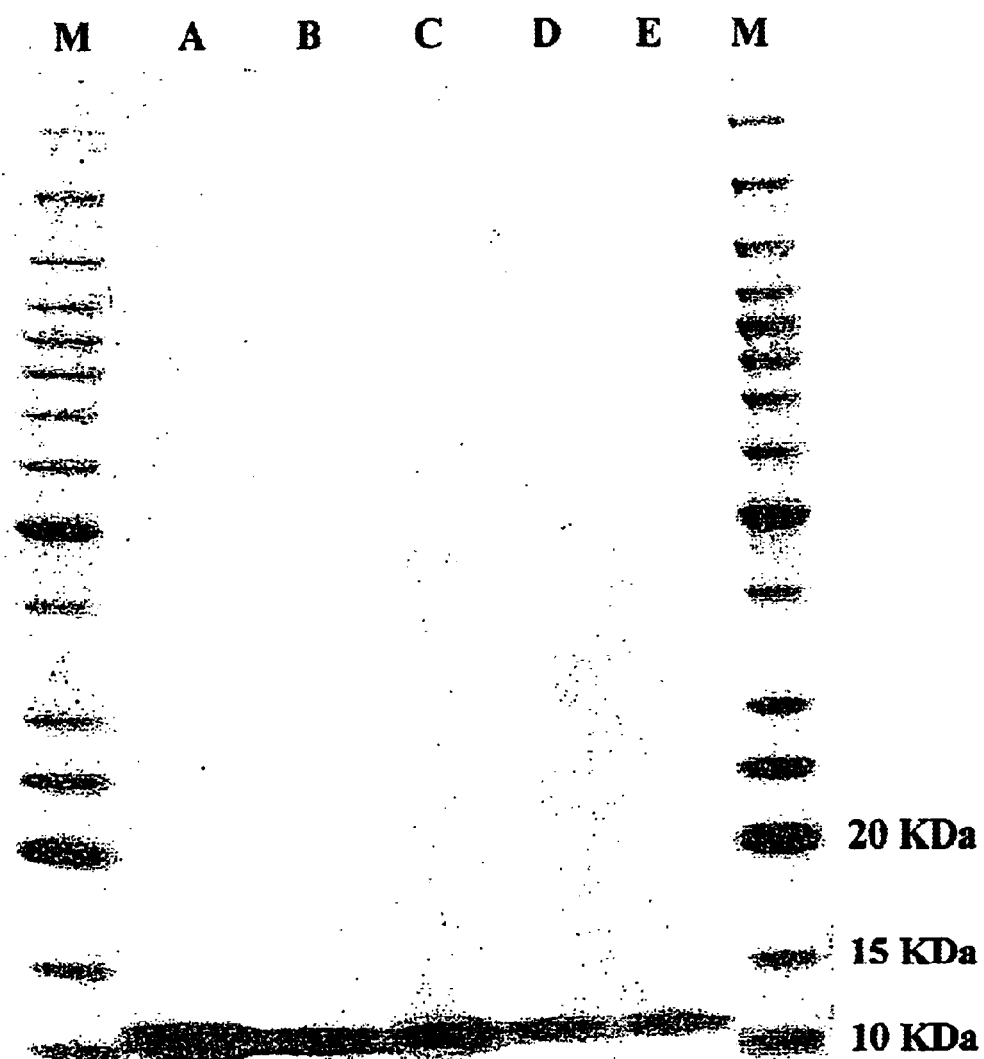
FIG. 16 is a photograph of an SDS-PAGE gel of S20 ribosomal protein purified from a side fraction of a native Int purification. Lanes M: BenchMark protein standards; lanes A through E: 5-, 2-, 2-, 1-, and 1-μl aliquots, respectively, of Mono S pool of S20.
Figure 17:
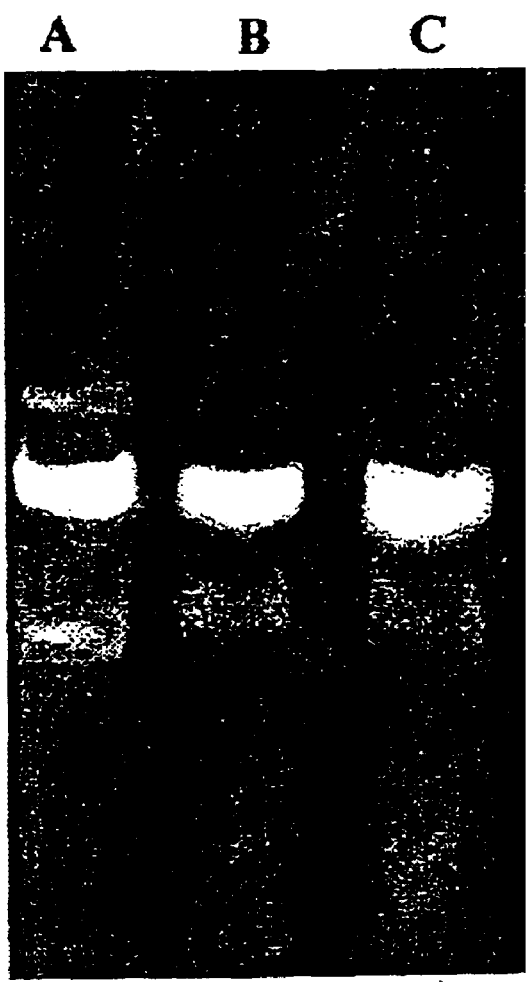
FIG. 17 is a photograph of an ethidium bromide-stained gel in an integrative recombination gel assay (see Materials and Methods) showing the ability of S20 protein in the Mono S pool (see FIG. 16) to stimulate Int activity. Lane A: Int plus S20; lane B: Int alone; lane C: Int dilution buffer alone. The slowest migrating band is the recombinant DNA product.

The side fractions generated early in the native Int purification (Materials and Methods section Purification of Native Int) were heated to 100° C., clarified by centrifugation, and assayed for ability to stimulate inactive Int. The supernatant from the first high speed centrifugation in the differential salt precipitation step was found to have the most stimulatory activity. Using this supernatant as starting material, a stimulatory protein was purified as described in Materials and Methods section Purification of Stimulatory Protein as a Side Fraction of a Native Int Preparation. A near homogeneous 11-KDa protein was purified after two column chromatography steps (FIG. 16) that stimulated inactive Int in the gel recombination assay (FIG. 17).

The 11-KDa protein was sent to the HHMI Biopolymer Laboratory, W.M. Keck Foundation, for amino terminal amino acid sequence analysis (Materials and Methods section Amino-Terminal Amino Acid Sequence Analysis of Stimulatory Proteins). The sequence was found to be Ala-Asn-Ile-Lys-Ser-Ala-Lys-Lys-Arg-Ala-Ile-Gln-Ser-Glu (SEQ ID NO:7). Search of the GenBank sequence data base revealed that this sequence matches amino acids 2 through 15 of E. coli 30S ribosomal protein S20 (Mackie, G. A. J. Biol. Chem. 256:8177–8182 (1981)). S20 is a very basic protein of 86 amino acids. In E. coli, S20 appears to be involved in association of the 30S ribosomal subunit with the 50S subunit and in formation of the 30S subunit translation initiation complex with fMet-tRNA and mRNA (Gotz, F. et. al Biochim. Biophys. Acta 1050: 93–97 (1990)). The gene for S20 was cloned, overexpressed, and purified (see Materials and Methods sections Cloning of S20 and Purification of Recombinant S20). The ability of recombinant S20 to stimulate Int was tested (see Results, PART III).

Purification from Total Cell Extract

Figure 19:
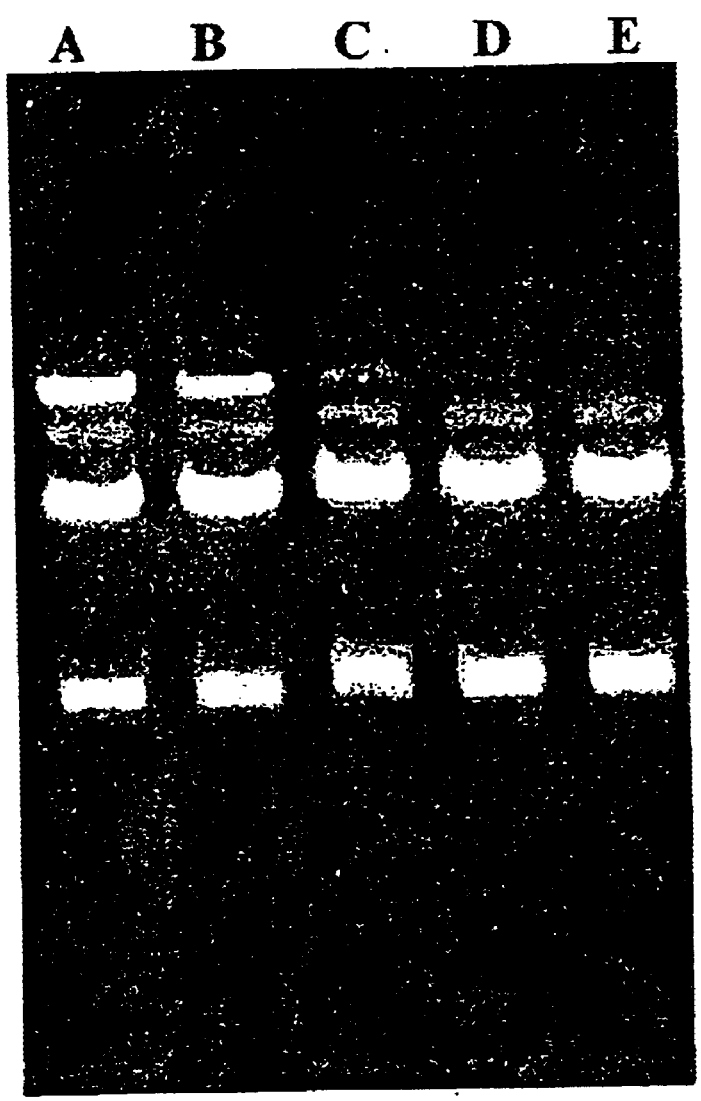
FIG. 19 is a photograph of an ethidium bromide-stained gel in an integrative recombination gel assay (Materials and Methods) showing stimulation of 37 ng of native Int by 900 ng of recombinant S20 (FIG. 19), 900 ng of S20 (see FIG. 16), and 10 μg of L27 (fraction 18 in FIG. 18). Lane A: recombinant S20; lane B: S20; lane C: L27; lane D: Int alone; lane E: no added Int or stimulatory protein.

Since we were able to identify one small, heat resistant, nucleic acid binding protein in extracts of E. coli that stimulates Int activity, we asked if there were others. Using the gel recombination assay with inactive Int to assay for stimulation of Int, and starting with total E. coli cell extract, purification of stimulatory activity was repeated (see Materials and Methods section Purification of Stimulatory Proteins from Cells Producing Native Int). Again, phosphocellulose followed by Mono S chromatography was used to fractionate heated E. coli extract. A second stimulatory protein was identified that migrated on SDS PAGE slightly faster than S20 (FIG. 18). This protein was also sent to the HHMI Biopolymer Laboratory, W.M. Keck Foundation, for sequence analysis. The sequence was found to be Ala-His-Lys-Lys-Ala-Gly-Gly-Ser-Thr-Arg-Asn (SEQ ID NO:8). Search of the GenBank sequence data base revealed that this sequence matches amino acids 2 through 12 of E. coli 50S ribosomal protein L27 (Jeong, J. H. et. al, DNA Seq. 4: 59–67 (1993)). L27 is a very basic protein of 85 amino acids. The proteins in fraction 18 (lanes A and B of FIG. 18), the primary constituent of which was L27, were tested for ability to stimulate Int in the integrative recombination gel assay. FIG. 19 shows that these proteins stimulated Int in the recombination assay. However, 10 times more L27 than S20 was required to produce a discernible recombinant DNA product.

Part III

Cloning of S20 and Demonstration of Activity

Cloning, Overexpression, and Purification of rS20

Figure 20:
FIG. 20 is a photograph of an SDS-PAGE gel of 2 μg of purified recombinant S20.

We cloned the gene for S20 from E. coli DNA under control of a T7 promoter using PCR (see Materials and Methods section Cloning of S20). The recombinant S20 was highly overexpressed and easily purified by EMD-SO$_4$ chromatography (see Materials and Methods section Purification of Recombinant S20). Approximately 110 mg of near homogeneous recombinant S20 (FIG. 20) was purified from 9 g of E. coli.

Characterization of rS20

Figure 21:
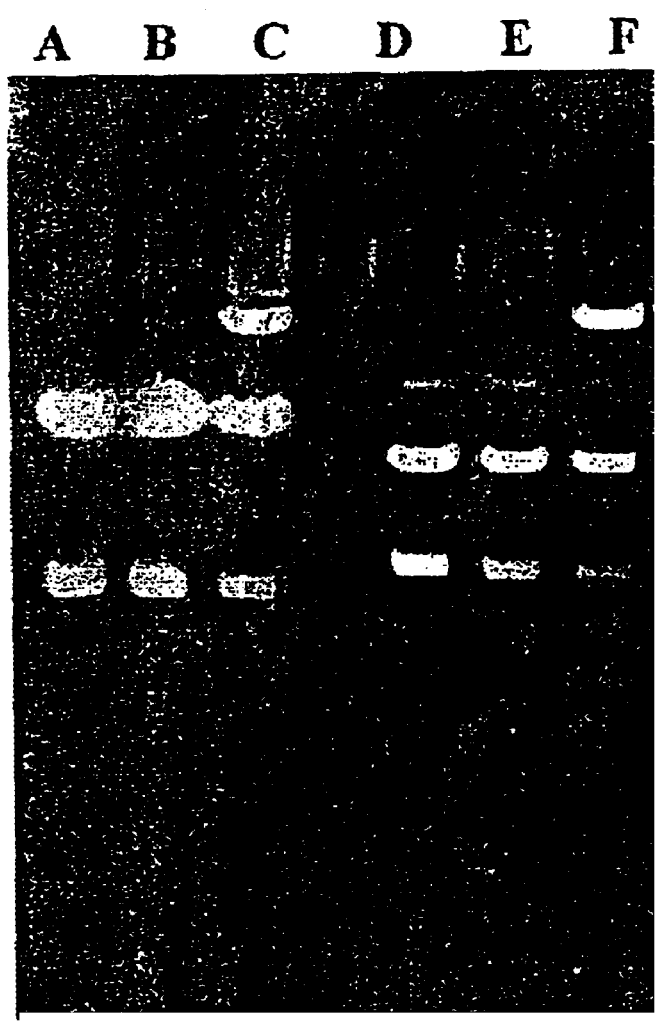
FIG. 21 is a photograph of an ethidium bromide-stained gel in integrative (lanes A to C) and excisive (lanes D to F) recombination gel assays, showing the recombinase activity of 59 ng of Int-His$_6$ in the presence of 0 ng (lanes B and E) and 382 ng (lanes C and F) of recombinant S20. All assays also contained 12.5 ng IHF. Excisive recombination assays contained 42 ng Xis-His$_6$. The assays analyzed in lanes A and D contained no Int-His$_6$ or rS20.

Recombinant S20 stimulated integrative and excisive λ recombination catalyzed by native Int as determined by gel assay (FIG. 19), and recombinant S20 also stimulated both integrative and excisive λ recombination catalyzed by recombinant Int-His$_6$ as determined both by gel assay (FIG. 21) and colony-forming assay (Tables 3 and 4). These results confirmed those obtained with native S20; that is, recombinant S20 stimulates the recombinase activity of Int.

TABLE 3

STIMULATION OF INT-HIS$_6$ BY RECOMBINANT S20 IN AN INTEGRATIVE RECOMBINATION COLONY-FORMING ASSAY*

| Amt. of Recombinant S20 (ng) | Number of Colonies Formed |
| --- | --- |
| 0 | 35 |
| 313 | 82 |
| 625 | 255 |
| 1,250 | 233 |
| 2,500 | 5 |

*See Materials and Methods for details of assay. All reaction mixtures contained 176 ng Int-His$_6$ and 10 ng IHF.

TABLE 4

STIMULATION OF INT-HIS$_6$ BY RECOMBINANT S20 IN AN EXCISIVE RECOMBINATION COLONY-FORMING ASSAY*

| Amt. of Recombinant S20 (ng) | Number of Colonies Formed |
| --- | --- |
| 0 | 9 |
| 158 | 86 |
| 313 | 1,392 |
| 625 | 83 |
| 1,250 | 23 |

*See Materials and Methods for details of assay. All reaction mixtures contained 176 ng Int-His$_6$, 12.5 ng IHF, and 28 ng Xis-His$_6$.

The order of addition of S20 and Int to a reaction appears to be important. Int should be mixed with S20 and the proteins added as a mixture to IHF and DNAs to obtain greatest stimulation of integrative recombination. If S20 is added before Int, or if Int is added before S20, less stimulation is observed. These results suggest S20 might be binding to Int and producing some kind of physical change that enhances its recombinase activity. Gel shift assays show that S20 binds to the DNA substrates in recombination assays. Thus, treatment of recombination assay mixtures containing large amounts of S20 with proteinase K is necessary to avoid trapping of DNA in wells during agarose gel electrophoresis. Titration of the amount of S20 versus number of recombinants obtained in both the integrative (Table 3) and excisive (Table 4) colony-forming recombination assay demonstrated rather sharp optima for amount of S20, particularly in the excisive reaction. The molar ratios of S20 to DNA nucleotides at the optimal amounts of S20 in these assays were 5 to 10 nucleotides per S20 molecule in the integrative reaction and 25 nucleotides per S20 molecule in the excisive reaction. We speculate that the binding footprint for a protein of the size of S20 (10 kDa) functioning as a monomer is in the range of 5 to 10 nucleotides per molecule of protein. The optimum for the integrative reaction falls in this range, suggesting that for optimal stimulation of the integrative recombination sufficient S20 must be present to coat the DNA. Making the same assumptions, it would appear that in the excisive reaction, the presence of sufficient S20 to coat the DNA inhibits the reaction. In any case, binding of S20 to DNA is probably also exerting an effect on the efficiency of the recombination reaction, just as does the binding of other small nonspecific DNA binding proteins (Segall, A. M. et. al, *EMBO J.* 13: 4536–4548 (1994)).

Part IV

Integrative Recombination Activity of Int and Int-His$_6$

We have completed three purifications of native λ Int following a modification (Materials and Methods) of the published purification procedure (Nash, H. A. *Methods Enz.* 100: 210–216 (1983)), and a much larger number of purifications of cloned Int-His$_6$ by a simpler procedure (Materials and Methods). As a result of characterization of the integrative recombinase activity of these preparations using the gel assay (see Materials and Methods section Integrative Recombination Gel Assay), we can draw several general conclusions about the activity of Int in the presence and absence of S20. First, preparations of Int or Int-His$_6$ that are nearly homogeneous and that are kept in a high salt (0.6 M KCl), low glycerol (10%) buffer during the final purification step (as recommended in the published purification procedure), and then are stored in that buffer in the presence or absence of BSA at −70° C., generally have reduced Int recombinase activity. But with all preparations tested, the activity can be increased by mixing Int with S20 before addition to an assay. We have found, however, that the activities of preparations of Int in the high salt buffer which appear lower can be increased to a certain extent by diluting the preparation in a low salt buffer (0.05 M KCl) before assay or more preferably by dialyzing the preparation into a buffer containing low salt (0.05 to 0.1 M KCl) and 50% (v/v) glycerol. Such preparations can then be stored at −20° C. or −70° C. Furthermore, regardless of the level of recombinase activity these preparations have by themselves before or after dialysis, addition of appropriate amounts of S20 stimulates that activity.

Conclusions

Taken together, these results demonstrate that at least two *E. coli* ribosomal proteins, S20 and L27, and possibly a third *E. coli* ribosomal protein, S15, stimulate λ Int-mediated recombination in vitro. In addition, purified preparations of λ Int that appear to be inactive in a λ recombination system can be restored to activity by the addition of S20.

Example 2

Stimulation of Integrase Recombination by other *E. coli* Ribosomal Proteins

In addition to S20 and L27, other *E. coli* ribosomal proteins may stimulate the activity of recombination systems, particularly the 1 Int system. In particular, *E. coli* ribosomal proteins that are basic and are about 14 kilodaltons or less in size are used to stimulate the activity of prokaryotic recombination systems. Such ribosomal proteins that may be used are shown in Table 5:

TABLE 5

Additional Ribosomal Proteins for Use in Stimulating Recombination Activity

| Ribosomal Protein | No. of Basic Residues (% of Total) | No. of Total Residues | Molecular Weight (Daltons) |
|---|---|---|---|
| S10 | 17 (16.5%) | 103 | 11,736 |
| S14 | 23 (23.7%) | 97 | 11,063 |
| S15 | 16 (18.4%) | 87 | 10,001 |
| S16 | 14 (17.1%) | 82 | 9,191 |
| S17 | 16 (19.3%) | 83 | 9,573 |
| S18 | 17 (23.0%) | 74 | 8,896 |
| S19 | 19 (20.9%) | 91 | 10,299 |
| S21 | 23 (32.9%) | 70 | 8,369 |
| L21 | 17 (16.5%) | 103 | 11,565 |
| L23 | 21 (21.2%) | 99 | 11,013 |
| L24 | 22 (21.4%) | 103 | 11,185 |
| L25 | 17 (18.1%) | 94 | 10,694 |
| L28 | 18 (23.4%) | 77 | 8,875 |
| L29 | 12 (19.0%) | 63 | 7,274 |
| L30 | 10 (17.2%) | 58 | 6,411 |
| L31 | 12 (19.4%) | 62 | 6,971 |
| L32 | 11 (19.6%) | 56 | 6,315 |
| L33 | 15 (27.8%) | 54 | 6,255 |
| L34 | 14 (30.4%) | 46 | 5,381 |

These ribosomal proteins are isolated from natural sources as generally described above for S20 and L27 and as discussed in *Ann. Rev. Biochem* 51:155 (1982), *Ann. Rev. Biochem.* 52:35 (1983), *Ann. Rev. Biochem* 53:75 (1984), and *Ann. Rev. Biochem* 66:679 (1997). Alternatively, the ribosomal proteins are prepared by recombinant DNA methodologies as generally outlined above for the production of S20 and Xis. Isolated ribosomal proteins are used to stimulate recombination activity, particularly that of Int, by including one or more of them in the compositions of the invention as described above for S20 and L27, and these compositions are used in integrative and excisive recombination assays, and in the recombinational cloning methods of the invention, as generally outlined in Example 1 for S20. In addition, ribosomal proteins corresponding to those described herein may be used in accordance with the invention. For example, ribosomal proteins from other prokaryotic sources, and from eukaryotic sources (e.g., yeast, fungi, animals (including mammals such as humans), plants, and the like) may be used in the methods and compositions of the invention.

Having now fully described the present invention in some detail by way of illustration and example for purposes of clarity of understanding, it will be obvious to one of ordinary skill in the art that the same can be performed by modifying or changing the invention within a wide and equivalent range of conditions, formulations and other parameters without affecting the scope of the invention or any specific embodiment thereof, and that such modifications or changes are intended to be encompassed within the scope of the appended claims.

All publications, patents and patent applications mentioned in this specification are indicative of the level of skill of those skilled in the art to which this invention pertains, and are herein incorporated by reference to the same extent as if each individual publication, patent or patent application was specifically and individually indicated to be incorporated by reference.

What is claimed is:

1. A method for cloning or subcloning one or more desired nucleic acid molecules comprising
   (a) forming a mixture by combining in vitro
      (i) one or more first nucleic acid molecules comprising one or more desired nucleic acid segments flanked by at least two recombination sites, wherein said recombination sites do not recombine with each other;
      (ii) one or more second nucleic acid molecules each comprising at least two recombination sites, wherein said recombination sites do not recombine with each other;
      (iii) at least one recombination protein; and
      (iv) at least one ribosomal protein that is present in an amount sufficient to enhance recombinational cloning; and
   (b) incubating said mixture under conditions sufficient to transfer one or more of said desired segments into one or more of said second nucleic acid molecules, thereby producing one or more desired third nucleic acid molecules.

2. The method of claim 1, further comprising:
   (c) forming a mixture by combining in vitro
      (i) one or more of said third molecules comprising said desired segments flanked by two or more recombination sites, wherein said recombination sites do not recombine with each other;
      (ii) one or more different fourth nucleic acid molecules each comprising two or more recombination sites, wherein said recombination sites do not recombine with each other;
      (iii) at least one recombination protein; and
      (iv) at least one ribosomal protein that is present in an amount sufficient to enhance recombinational cloning; and
   (d) incubating said mixture under conditions sufficient to transfer one or more of said desired segments into one or more different fourth nucleic acid molecules, thereby producing one or more different fifth nucleic acid molecules.

3. The method of claim 1, wherein said ribosomal protein is a prokaryotic ribosomal protein.

4. The method of claim 2, wherein said ribosomal protein is a prokaryotic ribosomal protein.

5. The method of claim 1, further comprising incubating said different third nucleic acid molecules with one or more different fourth nucleic acid molecules under conditions sufficient to transfer one or more of said desired segments into said different fourth nucleic acid molecules.

6. A method for cloning or subcloning desired nucleic acid molecules comprising:
   (a) forming a mixture by combining in vitro
      (i) one or more first nucleic acid molecules comprising one or more nucleic acid segments flanked by two or more recombination sites, wherein said recombination sites do not recombine with each other;
      (ii) two or more different second nucleic acid molecules each comprising two or more recombination sites, wherein said recombination sites do not recombine with each other;
      (iii) at least one recombination protein; and
      (iv) at least one ribosomal protein that is present in an amount sufficient to enhance recombinational cloning; and
   (b) incubating said mixture under conditions sufficient to transfer one or more of said desired segments into said different second nucleic acid molecules, thereby producing two or more different third nucleic acid molecules.

7. The method of claim 6, wherein said ribosomal protein is a prokaryotic ribosomal protein.

8. The method of claim 1, wherein said ribosomal protein is an *Escherichia coli* ribosomal protein.

9. The method of claim 1, wherein said ribosomal protein is a basic ribosomal protein.

10. The method of claim 1, wherein said ribosomal protein has a molecular weight of less than about 14 kilodaltons.

11. The method of claim 8, wherein said *E. coli* ribosomal protein is selected from the group of *E. coli* ribosomal proteins consisting of S10, S14, S15, S16, S17, S18, S19, S20, S21, L21, L23, L24, L25, L27, L28, L29, L30, L31, L32, L33 and L34.

12. The method of claim 8, wherein said ribosomal protein is S20.

13. The method of claim 8, wherein said ribosomal protein is L27.

14. The method of claim 8, wherein said ribosomal protein is S15.

15. The method of claim 6, wherein said recombination protein is a prokaryotic recombination protein.

16. The method of claim 1, wherein said recombination protein is selected from the group consisting of Int, Cre, FLP, Xis, IHF, FIS and HU, and combinations thereof.

17. The method of claim 1, wherein said recombination protein is Int.

18. A method for enhancement of recombinational cloning of one or more desired nucleic acid molecules comprising:
(a) forming a mixture by mixing in vitro one or more desired first nucleic acid molecules with one or more second nucleic acid molecules and with at least one ribosomal protein that is present in an amount sufficient to enhance recombinational cloning and an effective amount of at least one recombination protein; and
(b) incubating said mixture under conditions sufficient to transfer said one or more desired first nucleic acid molecules into one or more of said second nucleic acid molecules.

19. The method of claim 18, wherein said desired nucleic acid molecules are obtained from genomic DNA.

20. The method of claim 18, wherein said desired nucleic acid molecules are obtained from cDNA.

21. The method of claim 18, wherein said desired nucleic acid molecules are produced by chemical synthesis.

22. The method of claim 18, wherein said desired nucleic acid molecules are produced by amplification.

23. The method of claim 18, wherein said vector is a prokaryotic or eukaryotic vector.

24. The method of claim 23, wherein said eukaryotic vector replicates in yeast cells, plant cells, fish cells, eukaryotic cells, mammalian cells, or insect cells.

25. The method of claim 18, wherein said prokaryotic vector replicates in bacteria of the genera *Escherichia, Salmonella, Bacillus, Streptomyces* or *Pseudomonas*.

26. The method of claim 25, wherein said prokaryotic vector replicates in *E. coli*.

27. A method for enhancement of recombinational cloning, comprising contacting at least a first nucleic acid molecule and at least a second nucleic acid molecule, each comprising at least one recombination site, in vitro with one or more ribosomal proteins that are present in an amount sufficient to enhance recombinational cloning and with one or more recombination proteins to form a mixture, and incubating said mixture under conditions favoring the production of at least one product nucleic acid molecule.

28. The method of claim 27, wherein said ribosomal protein is a prokaryotic ribosomal protein.

29. The method of claim 27, wherein said ribosomal protein is an *Escherichia coli* ribosomal protein.

30. The method of claim 27, wherein said ribosomal protein is a basic ribosomal protein.

31. The method of claim 27, wherein said ribosomal protein has a molecular weight of less than about 14 kilodaltons.

32. The method of claim 29, wherein said *E. coli* ribosomal protein is selected from the group of *E. coli* ribosomal proteins consisting of S10, S14, S15, S16, S17, S18, S19, S20, S21, L21, L23, L24, L25, L27, L28, L29, L30, L31, L32, L33 and L34.

33. The method of claim 29, wherein said ribosomal protein is S20.

34. The method of claim 29, wherein said ribosomal protein is L27.

35. The method of claim 29, wherein said ribosomal protein is S15.

36. The method of claim 27, wherein said recombination protein is a prokaryotic recombination protein.

37. The method of claim 27, wherein said recombination protein is selected from the group consisting of Int, Cre, FLP, Xis, IHF, FIS and HU, and combinations thereof.

38. The method of claim 27, wherein said recombination protein is Int.

39. The method of claim 18, wherein said ribosomal protein is a prokaryotic ribosomal protein.

40. The method of claim 18, wherein said ribosomal protein is an *Escherichia coli* ribosomal protein.

41. The method of claim 18, wherein said ribosomal protein is a basic ribosomal protein.

42. The method of claim 18, wherein said ribosomal protein has a molecular weight of less than about 14 kilodaltons.

43. The method of claim 40, wherein said *E. coli* ribosomal protein is selected from the group of *E. coli* ribosomal proteins consisting of S10, S14, S15, S16, S17, S18, S19, S20, S21, L21, L23, L24, L25, L27, L28, L29, L30, L31, L32, L33 and L34.

44. The method of claim 40, wherein said *E. coli* ribosomal protein is S20.

45. The method of claim 40, wherein said *E. coli* ribosomal protein is L27.

46. The method of claim 40, wherein said *E. coli* ribosomal protein is S15.

47. The method of claim 18, wherein said recombination protein is a eukaryotic recombination protein.

48. The method of claim 18, wherein said recombination protein is selected from the group consisting of Int, Cre, FLP, Xis, IHF and HU, and combinations thereof.

49. The method of claim 18, wherein said recombination protein is Int.

50. The method of claim 18, wherein said composition further comprises one or more nucleic acid molecules selected from the group consisting of one or more Insert Donor molecules, one or more Vector Donor molecules, one or more Cointegrate molecules, one or more Product molecules and one or more Byproduct molecules.

51. The method of claim 1, wherein said ribosomal protein is a recombinant ribosomal protein.

52. The method of claim 6, wherein said ribosomal protein is a recombinant ribosomal protein.

53. The method of claim 18, wherein said ribosomal protein is a recombinant ribosomal protein.

54. The method of claim 27, wherein said ribosomal protein is a recombinant ribosomal protein.

55. The method of claim 1, wherein said recombination protein is a recombinant recombination protein.

56. The method of claim 6, wherein said recombination protein is a recombinant recombination protein.

57. The method of claim 18, wherein said recombination protein is a recombinant recombination protein.

58. The method of claim 27, wherein said recombination protein is a recombinant recombination protein.

59. The method of any one of claims 1, 2, 6, 18 and 27, wherein said at least one recombination protein is at least one isolated Int protein and at least one isolated IHF protein.

60. The method of any one of claims 1, 2, 6, 18 and 27, wherein said at least one recombination protein is at least one isolated Int protein, at least one isolated IHF protein and at least one isolated Xis protein.

61. The method of any one of claims 1, 2, 6, 18 and 27, wherein said mixture further comprises at least one isolated FIS protein.

62. The method of any one of claims 1, 2, 6, 18 and 27, wherein said mixture further comprises spermidine.

63. The method of any one of claims 1, 2, 6, 18 and 27, wherein said mixture further comprises Tris-HCl.

64. The method of any one of claims 1, 2, 6, 18 and 27, wherein said mixture further comprises ethylenediamine tetracetic acid (EDTA).

65. The method of any one of claims 1, 2, 6, 18 and 27, wherein said mixture further comprises bovine serum albumin (BSA).

66. The method of any one of claims 1, 2, 6, 18 and 27, wherein said mixture further comprises at least one additional isolated recombination protein selected from the group consisting of a Cre protein, an FLP protein, a γδ protein, a Tn3 resolvase protein, a Hin protein, a Gin protein, and a Cin protein.

67. The method of any one of claims 1, 2, 6, 18 and 27, wherein said recombination protein is at least one isolated Cre protein.

68. The method of any one of claims 1, 2, 6, 18 and 27, wherein said mixture comprises at least one isolated Int protein, at least one isolated IHF protein, spermidine, Tris-HCl, EDTA and BSA.

69. The method of any one of claims 1, 2, 6, 18 and 27, wherein said mixture comprises at least one isolated Int protein, at least one isolated IHF protein, at least one isolated Xis protein, spermidine, Tris-HCl, EDTA and BSA.

70. The method of any one of claims 1, 2, 6, 18 and 27, wherein said mixture comprises at least one isolated Int protein, at least one isolated IHF protein and spermidine.

71. The method of any one of claims 1, 2, 6, 18 and 27, wherein said mixture comprises at least one isolated Int protein, at least one isolated IHF protein, at least one isolated Xis protein and spermidine.

72. The method of any one of claims 1, 2, 6, 18 and 27, wherein said first or second nucleic acid molecule is an Insert Donor nucleic acid molecule.

73. The method of any one of claims 1, 2, 6, 18 and 27, wherein said first or second nucleic acid molecule is a Vector Donor nucleic acid molecule.

74. The method of claim 2, wherein said fourth nucleic acid molecule is a Vector Donor nucleic acid molecule.

\* \* \* \* \*

UNITED STATES PATENT AND TRADEMARK OFFICE
CERTIFICATE OF CORRECTION

PATENT NO. : 6,964,861 B1
APPLICATION NO. : 09/438358
DATED : November 15, 2005
INVENTOR(S) : Gerard et al.

It is certified that error appears in the above-identified patent and that said Letters Patent is hereby corrected as shown below:

On the Title Page:
In column 1 of the face page, at item (54), please delete the word "of" from the title of the invention.

Signed and Sealed this

Eighteenth Day of July, 2006

JON W. DUDAS
*Director of the United States Patent and Trademark Office*

SEQUENCE LISTING

<160> NUMBER OF SEQ ID NOS: 8

<210> SEQ ID NO 1
<211> LENGTH: 45
<212> TYPE: DNA
<213> ORGANISM: Artificial sequence
<220> FEATURE:
<223> OTHER INFORMATION: Description of artificial sequence: synthetic
      oligonucleotide

<400> SEQUENCE: 1
tattattatc atatgggacg acgtcgaagt catgagcgcc gggat               45

<210> SEQ ID NO 2
<211> LENGTH: 58
<212> TYPE: DNA
<213> ORGANISM: Artificial sequence
<220> FEATURE:
<223> OTHER INFORMATION: Description of artificial sequence: synthetic
      oligonucleotide

<400> SEQUENCE: 2
attattaagc ttattaatgg tgatgatggt gatgtttgat ttcaattttg tcccactc     58

<210> SEQ ID NO 3
<211> LENGTH: 33
<212> TYPE: DNA
<213> ORGANISM: Artificial sequence
<220> FEATURE:
<223> OTHER INFORMATION: Description of artificial sequence: synthetic
      oligonucleotide

<400> SEQUENCE: 3
tattattatc atatgtactt gacacttcag gag                 33

<210> SEQ ID NO 4
<211> LENGTH: 55
<212> TYPE: DNA
<213> ORGANISM: Artificial sequence
<220> FEATURE:
<223> OTHER INFORMATION: Description of artificial sequence: synthetic
      oligonucleotide

<400> SEQUENCE: 4
attattaagc ttattaatgg tgatgatggt gatgtgactt cgccttcttc ccatt        55

<210> SEQ ID NO 5
<211> LENGTH: 36
<212> TYPE: DNA
<213> ORGANISM: Artificial sequence
<220> FEATURE:
<223> OTHER INFORMATION: Description of artificial sequence: synthetic
      oligonucleotide

<400> SEQUENCE: 5
tattattatc atatggctaa tatcaaatca gctaag              36

<210> SEQ ID NO 6
<211> LENGTH: 33
<212> TYPE: DNA
<213> ORGANISM: Artificial sequence
<220> FEATURE:
<223> OTHER INFORMATION: Description of artificial sequence: synthetic
      oligonucleotide

<400> SEQUENCE: 6

```
-continued attattggat ccattaagcc agtttgttga tct                               33

<210> SEQ ID NO 7
<211> LENGTH: 14
<212> TYPE: PRT
<213> ORGANISM: Escherichia coli

<400> SEQUENCE: 7

Ala Asn Ile Lys Ser Ala Lys Lys Arg Ala Ile Gln Ser Glu
 1               5                  10

<210> SEQ ID NO 8
<211> LENGTH: 11
<212> TYPE: PRT
<213> ORGANISM: Escherichia coli

<400> SEQUENCE: 8

Ala His Lys Lys Ala Gly Gly Ser Thr Arg Asn
 1               5                  10
```